United States Patent [19]

Takaya et al.

[11] 4,405,617
[45] Sep. 20, 1983

[54] 3-(PROPYNYLTETRAZOL)THIOMETHYL-3-CEPHEMS

[75] Inventors: Takao Takaya, Kawanishi; Yoshikazu Inoue, Amagasaki; Masayoshi Murata, Mino; Hisashi Takasugi, Kohamanishi, all of Japan

[73] Assignee: Fujisawa Pharmaceutical Co., Ltd., Osaka, Japan

[21] Appl. No.: 230,675

[22] Filed: Feb. 2, 1981

[30] Foreign Application Priority Data

Feb. 11, 1980 [GB] United Kingdom ................ 8004477
Jun. 13, 1980 [GB] United Kingdom ................ 8019376

[51] Int. Cl.³ .................... A61K 31/545; C07D 501/56
[52] U.S. Cl. ....................................... 424/246; 544/26; 544/27; 548/251
[58] Field of Search ..................... 544/26, 27; 424/246

[56] References Cited

U.S. PATENT DOCUMENTS 4,172,892 10/1979 Nannini et al. ....................... 544/26
4,268,509 5/1981 Teraji et al. ........................... 544/27
4,278,793 7/1981 Durckheimer et al. .............. 544/27

*Primary Examiner*—Paul M. Coughlan, Jr.

*Attorney, Agent, or Firm*—Oblon, Fisher, Spivak, McClelland & Maier

[57] ABSTRACT

This invention relates to a new cephem compound of the formula:

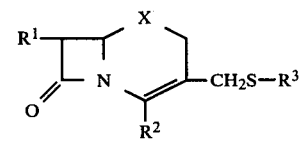

wherein
$R^1$ is amino or a substituted amino group;
$R^2$ is carboxy or a protected carboxy group;
$R^3$ is a tetrazolyl group having a lower alkynyl group; and
X is —S— or

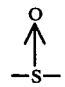

and pharmaceutically acceptable salts thereof, of high antimicrobial activity.

12 Claims, No Drawings

3-(PROPYNYLTETRAZOL)THIOMETHYL-3-CEPHEMS

The present invention relates to new cephem compounds and pharmaceutically acceptable salts thereof. More particularly, it relates to new cephem compounds and pharmaceutically acceptable salts thereof, which have antimicrobial activities and to processes for preparation thereof, to pharmaceutical composition comprising the same, and to a method of using the same therapeutically in treatment of infectious diseases in human being and animals.

Accordingly, it is one object of the present invention to provide new cephem compounds and pharmaceutically acceptable salts thereof, which are active against a number of pathogenic microorganisms.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula (I).

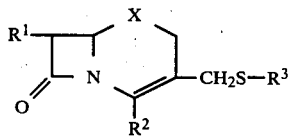

(I)

wherein
  $R^1$ is amino or a substituted amino group;
  $R^2$ is carboxy or a protected carboxy group;
  $R^3$ is a tetrazolyl group having a lower alkynyl group; and
  X is —S— or

As to the object compounds (I) and the starting compounds of the present invention, it is to be understood that there may be one or more stereoisomeric pair(s) such as optical and/or geometrical isomers due to asymmetric carbon atom(s) and/or double bond(s), in the molecule, and these isomers are also included within the scope of the present invention.

According to the present invention, the object compounds (I) can be prepared by the following processes which are illustrated in the following scheme.

Process 1

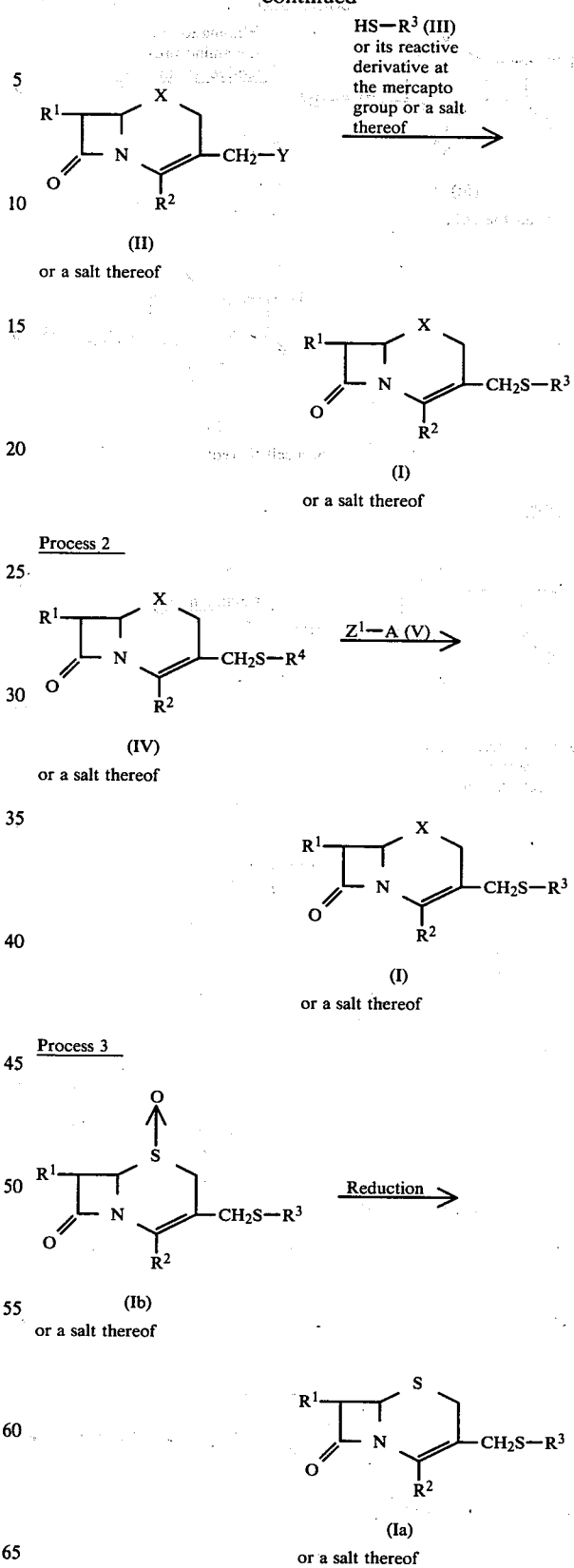

-continued

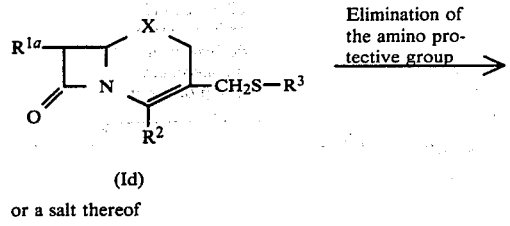

(Id)
or a salt thereof

Elimination of the amino protective group →

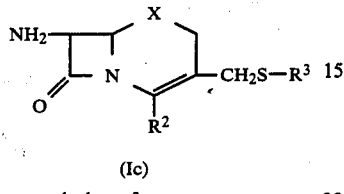

(Ic)
or a salt thereof

Process 5

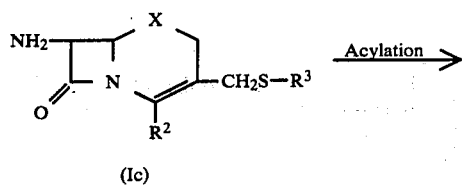

(Ic)
or its reactive derivatives
at the amino group
or a salt thereof

Acylation →

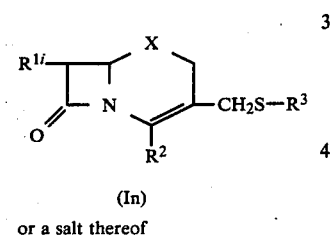

(In)
or a salt thereof

Process 6

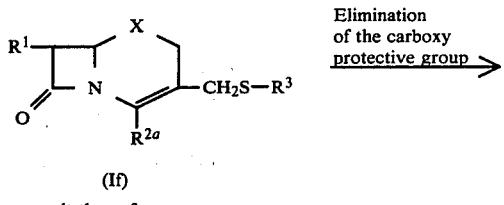

(If)
or a salt thereof

Elimination of the carboxy protective group →

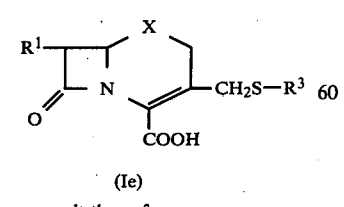

(Ie)
or a salt thereof

Process 7

-continued

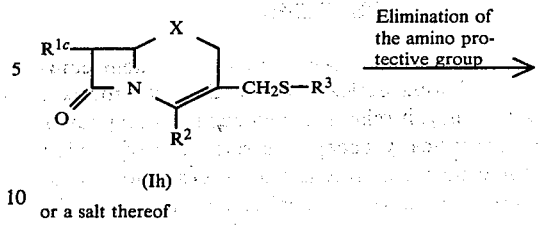

(Ih)
or a salt thereof

Elimination of the amino protective group →

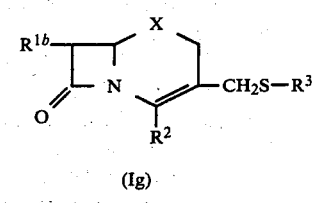

(Ig)
or a salt thereof

Process 8

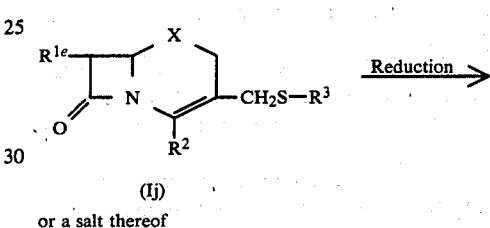

(Ij)
or a salt thereof

Reduction →

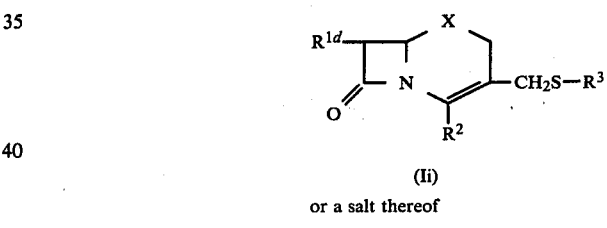

(Ii)
or a salt thereof

Process 9

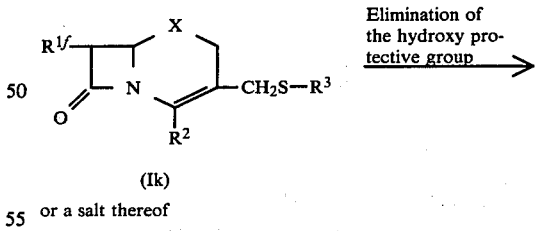

(Ik)
or a salt thereof

Elimination of the hydroxy protective group →

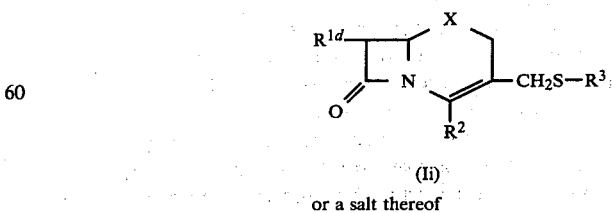

(Ii)
or a salt thereof

Process 10

-continued

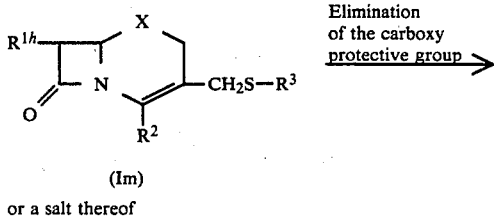

(Im)
or a salt thereof

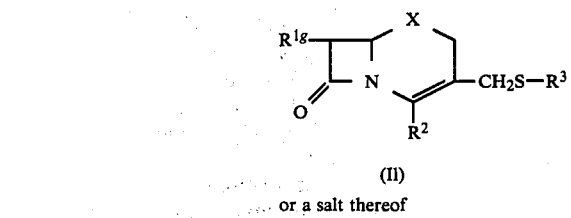

(II)
or a salt thereof wherein
R¹, R², R³ and X are each as defined above;
Y is a group which can be substituted by a group of the formula: —S—R³, (wherein R³ is as defined above);
A is lower alkynyl;
$Z^1$ is an acid residue;
$R^4$ is tetrazolyl;
$R^{1a}$ is a protected amino;
$R^{1i}$ is an acylamino;
$R^{2a}$ is protected carboxy;
$R^{1b}$ is acylamino having an amino group;
$R^{1c}$ is acylamino having a protected amino group;
$R^{1d}$ is acylamino having a hydroxy group;
$R^{1e}$ is acylamino having an oxo group;
$R^{1f}$ is acylamino having a protected hydroxy group;
$R^{1g}$ is acylamino having a carboxy group; and
$R^{1h}$ is acylamino having a protected carboxy group.

Among the starting compounds of the present invention, the compounds (III) and some of the compounds (IV) are novel and can be prepared by the processes which are illustrated in the following schemes.

Process A

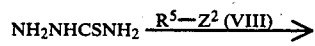

(IX)
or a salt thereof

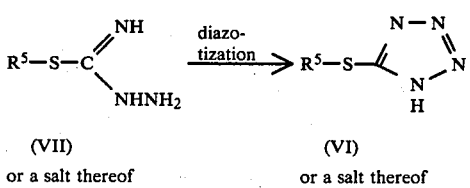

(VII)                           (VI)
or a salt thereof           or a salt thereof Process B

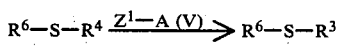

(XI)                    (X)

Process C

-continued (1) $R^5-S-R^4$ $\xrightarrow{\text{Elimination of the aralkyl group}}$ $HS-R^4$ (XIII)                                                 (XII)
or a salt thereof                              or a salt thereof (2) $R^6-S-R^3$ $\xrightarrow{\text{Elimination of the mercapto protective group}}$ $HS-R^3$ (X)                                                     (III)
                                                 or a salt thereof Process D (1) $HS-R^4$ $\xrightarrow{R^5-Z^2 \text{ (VIII)}}$ $R^5-S-R^4$ (XII)                                       (XIII)
or a salt thereof                 or a salt thereof (2) $HS-R^3$ $\xrightarrow{R^6-Z^3 \text{ (XIV)}}$ $R^6-S-R^3$ (III)                                       (X)
or a salt thereof Process E

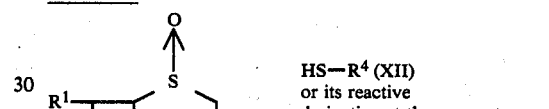

(XV)
or a salt thereof

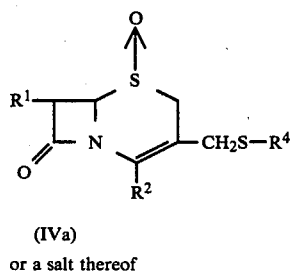

(IVa)
or a salt thereof wherein
R¹, R², R³, R⁴, Y, A and $Z^1$ are each as defined above;
$R^5$ is ar(lower)alkyl;
$R^6$ is a mercapto protective group; and
$Z^2$ and $Z^3$ are each an acid residue.

Suitable pharmaceutically acceptable salts of the object compounds (I) are conventional non-toxic salts and may include a metal salt such as an alkali metal salt (e.g. sodium salt, potassium salt, etc.) and alkaline earth metal salt (e.g. calcium salt, magnesium salt, etc.), ammonium salt, an organic amine salt (e.g. trimethylamine salt, triethylamine salt, pyridine salt, picoline salt, etc.), an organic acid salt (e.g. formate, trifluoroacetate, maleate, tartrate, methanesulfonate, benzenesulfonate, toluenesulfonate etc.), an inorganic acid salt (e.g. hydrochloride, hydrobromide, sulfate, phosphate, etc.), or a salt with an amino acid (e.g. arginine, aspartic acid, lysine, glutamic acid, etc.), and the like.

In the above and subsequent description of the present specification, suitable examples and illustrations for the various definitions to be included within the scope of the present invention are explained in details as follows.

The term "lower" is intended to mean 1 to 6 carbon atoms and the term "higher" is intended to mean 7 to 18 carbon atoms, unless otherwise indicated.

Suitable "substituted amino group" for $R^1$ may include an amino group substituted by a conventional substituent used in Cephalosporin and Penicillin compounds such as acyl as mentioned below, ar(lower)alkyl (e.g. benzyl, phenethyl, trityl, etc.) or the like.

Suitable "acyl" and "acyl moiety" in the terms "acylamino" and "acyloxy" may include carbamoyl, an aliphatic acyl group, an acyl group containing an aromatic ring (hereinafter referred to as aromatic acyl) and an acyl group containing a heterocyclic ring (hereinafter referred to as heterocyclic acyl).

Suitable example of said acyl may be illustrated as follows:

Aliphatic acyl such as lower or higher alkanoyl (e.g. formyl, acetyl, succinyl, hexanoyl, heptanoyl, stearoyl, etc.);
lower or higher alkoxycarbonyl (e.g. methoxycarbonyl, ethoxycarbonyl, tert-butoxycarbonyl, tert-pentyloxycarbonyl, heptyloxycarbonyl, etc.);
lower or higher alkanesulfonyl (e.g. methanesulfonyl, ethanesulfonyl, etc.);
lower alkenylthio(lower)alkanoyl (e.g. vinylthioacetyl, allylthioacetyl, allylthiopropionyl, butenylthioacetyl etc.); or the like;
Aromatic acyl such as aroyl (e.g. benzoyl, toluoyl, naphthoyl, phthaloyl etc.);
ar(lower)alkanoyl (e.g. phenylacetyl, phenylpropionyl, etc.);
aryloxycarbonyl (e.g. phenoxycarbonyl, naphthyloxycarbonyl, etc.);
ar(lower)alkoxycarbonyl (e.g. benzyloxycarbonyl, phenethyloxycarbonyl, etc.);
aryloxy(lower)alkanoyl (e.g. phenoxyacetyl, phenoxypropionyl, etc.);
arylglyoxyloyl (e.g. phenylglyoxyloyl, naphthylglyoxyloyl, etc.);
arenesulfonyl (e.g. benzenesulfonyl, p-toluenesulfonyl, etc.); or the like;
Heterocyclic acyl such as:
heterocycliccarbonyl (e.g. thenoyl, furoyl, nicotinoyl, etc.);
heterocyclic(lower)alkanoyl (e.g. thienylacetyl, thiazolylacetyl, dithiinylacetyl, pyridylacetyl, pyrimidinylacetyl, thiadiazolylacetyl, triazolylacetyl, tetrazolylacetyl, furylacetyl, oxazolylacetyl, thiazolylpropionyl, etc.);
heterocyclicglyoxyloyl (e.g. thiazolylglyoxyloyl, thienylglyoxyloyl, etc.); or the like.

The acyl and acyl moiety as stated above may have one or more, same or different, suitable substituent(s) such as lower alkyl (e.g. methyl, ethyl, propyl, etc.); lower alkoxy (e.g. methoxy, ethoxy, propoxy, etc.); lower alkylthio (e.g. methylthio, ethylthio, etc.); lower alkylamino (e.g. methylamino, etc.); halogen (e.g. chlorine, bromine, fluorine or iodine); carboxy; protected carboxy group as mentioned below; amino; protected amino group as mentioned below; hydroxy; protected hydroxy as mentioned below; imino; oxo;

a group of the formula: $=N-OR^7$ (wherein $R^7$ is organic residue which may have suitable substituent(s)) or the like.

Suitable "organic residue which may have suitable substituent(s)" for $R^7$ may include an aliphatic and aromatic, for example,
lower alkyl (e.g. methyl, ethyl, propyl, isopropyl, butyl, isobutyl, tert-butyl, pentyl, neopentyl, tert-pentyl, hexyl, etc.);
lower alkenyl (e.g. vinyl, 1-propenyl, allyl, 1-methylallyl, 1 or 2 or 3-butenyl, 1 or 2 or 3 or 4-pentenyl, 1 or 2 or 3 or 4 or 5-hexenyl, etc.);
lower alkynyl (e.g. ethynyl, 1-propynyl, 2-propynyl, 1-methyl-2-propynyl, 1 or 2 or 3-butynyl, 1 or 2 or 3 or 4-pentynyl, 1 or 2 or 3 or 4 or 5-hexynyl, etc.);
cycloalkyl (e.g. cyclopropyl, cyclobutyl, cyclopentyl, cyclohexyl, cycloheptyl, etc.);
cyclo(lower)alkenyl (e.g. cyclopropenyl, cyclobutenyl, cyclopentenyl, cyclohexenyl, etc.);
aryl (e.g. phenyl, tolyl, xylyl, cumenyl, naphthyl, etc.);
ar(lower)alkyl such as phenyl(lower)alkyl (e.g. benzyl, phenethyl, phenylpropyl, etc.);
ar(lower)alkyl having at least one suitable substituent(s) such as halogen as mentioned below (e.g. chlorobenzyl, dichlorobenzyl, trichlorobenzyl, fluorobenzyl, fluorophenethyl, fluorophenylpropyl, etc.); carboxy(lower)alkyl (eg. carboxymethyl, carboxyethyl, carboxypropyl, etc.);
protected carboxy(lower)alkyl wherein a protected carboxy group is as mentioned below (e.g. protected carboxymethyl protected carboxyethyl, protected carboxypropyl, etc.) or the like.

In this connection, when the acyl and acyl moiety have a group of the formula: $=N-OR^7$ (wherein $R^7$ is as defined above) as substituent(s), there are geometrical isomers (syn and anti isomers) due to the presence of double bond. And, for example, the syn isomer means one geometrical isomer having the group of the formula:

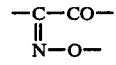

and the corresponding anti isomer means the other geometrical isomer having the group of the formula:

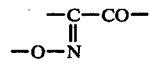

Suitable "protected carboxy group" for $R^2$ and $R^{2a}$ and "protected carboxy" moiety in the terms "acylamino having a protected carboxy group" for $R^{1h}$ and "protected carboxy(lower)alkyl" may include an esterified carboxy and the like, and suitable examples of the ester moiety in said esterified carboxy may be the ones such as lower alkyl ester (e.g. methyl ester, ethyl ester, propylester, isopropyl ester, butyl ester, tert-butyl ester, isobutyl ester, pentyl ester, hexyl ester, 1-cyclopropyl ethyl ester, etc.) which may have at least one suitable substituent(s), for example, lower alkanoyloxy(lower)alkyl ester (e.g. acetoxymethyl ester, propionyloxymethyl ester, butyryloxymethyl ester, valeryloxymethyl ester, pivaloyloxymethyl ester, 2-acetoxyethyl ester, 2-propionyloxyethyl ester, hexanoyloxymethyl ester, etc.), lower alkanesulfonyl(lower)alkyl ester (e.g. 2-mesylethyl ester, etc.) or mono (or di or tri)-halo(lower)alkyl ester (e.g. 2-iodoethyl ester, 2,2,2-trichloroethyl ester, etc.); lower alkenyl ester (e.g. vinyl ester, allyl ester, etc.);

lower alkynyl ester (e.g. ethynyl ester, propynyl ester, etc.);

ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis-(methoxyphenyl)methyl ester, 3,4-dimethoxybenzyl ester, 4-hydroxy-3,5-ditertiarybutylbenzyl ester, etc.);

aryl ester which may have at least one suitable substituent(s) (e.g. phenyl ester, 4-chlorophenyl ester, tolyl ester, tertiarybutylphenyl ester, xylyl ester, mesityl ester, cumenyl ester, etc.), and the like.

Suitable "tetrazolyl" for $R^4$ and "tetrazolyl moiety" in the term "tetrazolyl group having a lower alkynyl group" for $R^3$ may include 1H-tetrazol-5-yl, 2H-tetrazol-5-yl and the like.

Suitable "lower alkynyl" for A and "lower alkynyl moiety" in the term "tetrazolyl group having a lower alkynyl group" for $R^3$ are ones having 2 to 6 carbon atoms and may include ethynyl, 2-propynyl, 1-methyl-2-propynyl, 1 or 2 or 3-butynyl, 1 or 2 or 3 or 4-pentynyl, 1 or 2 or 3 or 4 or 5-hexynyl and the like, and preferably ones having 2 to 4 carbon atoms.

Suitable example of Y may include an acid residue (e.g., azido, halogen as mentioned above, acyloxy as mentioned above, etc.) and the like.

Suitable "acid residue" for $Z^1$, $Z^2$ and $Z^3$ may include halogen (e.g. chlorine, bromine, iodine etc.), azido, and the like.

Suitable "protected amino group" and "protected amino moiety" in the term "acylamino having a protected amino group" for $R^{1c}$ may include an acylamino, wherein an acyl moiety is as mentioned above, and an amino group substituted by a conventional protecting group such as ar(lower)alkyl (e.g. benzyl, trityl, etc.) and the like.

Suitable "protected hydroxy" in the term "acylamino having a protected hydroxy group" for $R^{1f}$ may include an acyloxy, wherein an acyl moiety is as mentioned above, and a hydroxy group substituted with a conventional protecting group such as tetrahydropyranyl, ar(lower)alkyl as aforementioned and the like.

Suitable "ar(lower)alkyl" for $R^5$ may include mono-(or di or tri)-phenyl(lower)alkyl such as benzyl, phenethyl, phenylpropyl, benzhydryl, trityl and the like.

Suitable "mercapto-protective group" for $R^6$ may include a conventional protective group such as lower alkyl (e.g., methyl, ethyl, propyl, isopropyl, butyl, isobutyl, tert-butyl, pentyl, neopentyl, tert-pentyl, hexyl, etc.), ar(lower)alkyl as mentioned above and the like.

The preferable examples of the object compound (I) are exemplified as follows:

Preferable example of $R^1$ is amino or acylamino wherein acyl moiety is, for example,
ar(lower)alkanoyl, more preferably phenyl(lower)alkanoyl (e.g., phenylacetyl, phenylpropionyl, etc.);
arylglycoloyl, more preferably phenylglycoloyl;
ar(lower)alkanoyl having a protected hydroxy group, preferably phenyl(lower)alkanoyl having an acyloxy group, more preferably phenyl(lower)alkanoyl having a lower alkanoyloxy group [e.g., 2-formyloxy-2-phenylacetamido, etc.];

tetrazolyl(lower)alkanoyl [e.g., 2-(1H-tetrazol-1-yl)acetyl, 3-(1H-tetrazol-1-yl)propionyl, etc.];
aminothiazolylglyoxyloyl [e.g., 2-(2-aminothiazol-4-yl)glyoxyloyl, etc.];
protected aminothiazolylglyoxyloyl, preferably acylaminothiazolylglyoxyloyl, more preferably lower alkanoylaminothiazolylglyoxyloyl [e.g., 2-(2-formamidothiazol-4-yl)glyoxyloyl, etc.];
aminothiazolylglycoloyl [e.g., 2-(2-aminothiazol-4-yl)glycoloyl, etc.];
protected aminothiazolylglycoloyl, preferably acylaminothiazolylglycoloyl, more preferably lower alkanoylaminothiazolylglycoloyl [e.g., 2-(2-formaminothiazol-4-yl)glycoloyl, etc.];
thiazolyl(lower)alkanoyl having a lower alkoxyimino group, more preferably 2-lower alkoxyimino-2-thiazolyl acetyl [e.g., 2-methoxyimino-2-thiazolylacetyl, 2-ethoxyimino-2-thiazolylacetyl, 2-propoxyimino-2-thiazolylacetyl, etc.];
aminothiazolyl(lower)alkanoyl having a lower alkoxyimino group, more preferably 2-lower alkoxyimino-2-aminothiazolylacetyl [e.g. 2-methoxyimino-2-(2-aminothiazol-4-yl)acetyl, 2-ethoxyimino-2-(2-aminothiazol-4-yl)acetyl, 2-propoxyimino-2-(2-aminothiazol-4-yl)acetyl, 2-isopropoxyimino-2-(2-aminothiazol-4-yl)acetyl, 2-butoxyimino-2-(2-aminothiazol-4-yl)acetyl, 2-pentyloxyimino-2-(2-aminothiazol-4-yl)acetyl, 2-hexyloxyimino-2-(2-aminothiazol-4-yl)acetyl, etc.];
protected aminothiazolyl(lower)alkanoyl having a lower alkoxyimino group, preferably acylaminothiazolyl(lower)alkanoyl having a lower alkoxyimino group, more preferably 2-lower alkoxyimino-2-lower alkanoylaminothiazolylacetyl [e.g., 2-methoxyimino-2-(2-formamidothiazol-4-yl)acetyl, 2-ethoxyimino-2-(2-formamidothiazol-4-yl)acetyl, 2-propoxyimino-2-(2-formamidothiazol-4-yl)acetyl, 2-isopropoxyimino-2-(2-formamidothiazol-4-yl)acetyl, 2-butoxyimino-2-(2-formamidothiazol-4-yl)acetyl, 2-pentyloxyimino-2-(2-formamidothiazol-4-yl)acetyl, 2-hexyloxyimino-2-(2-formamidothiazol-4-yl)acetyl, etc.];
aminothiazolyl(lower)alkanoyl having a lower alkenyloxyimino group, more preferably 2-lower alkenyloxyimino-2-aminothiazolylacetyl [e.g. 2-vinyloxyimino-2-(2-aminothiazol-4-yl)acetyl, 2-allyloxyimino-2-(2-aminothiazol-4-yl)acetyl, etc.];
protected aminothiazolyl(lower)alkanoyl having a lower alkenyloxyimino group, preferably acylaminothiazolyl(lower)alkanoyl having a lower alkenyloxyimino group, more preferably 2-lower alkenyloxyimino-2-lower alkanoylaminothiazolylacetyl [e.g., 2-allyloxyimino-2-(2-formamidothiazol-4-yl)acetyl, etc.];
aminothiazolyl(lower)alkanoyl having a lower alkynyloxyimino group, more preferably 2-lower alkynyloxyimino-2-aminothiazolylacetyl [e.g., 2-ethynyloxyimino-2-(2-aminothiazol-4-yl)acetyl, 2-(2-propynyloxyimino)-2-(2-aminothiazol-4-yl)acetyl, etc.];
protected aminothiazolyl(lower)alkanoyl having a lower alkynyloxyimino group, preferably acylaminothiazolyl(lower)alkanoyl having a lower alkynyloxyimino group, more preferably 2-lower alkynyloxyimino-2-lower alkanoylaminothiazolylacetyl [e.g., 2-(2-propynyloxyimino)-2-(2-formamidothiazol-4-yl)acetyl, etc.];

aminothiazolyl(lower)alkanoyl having a cycloalkoxyimino group, more preferably 2-cycloalkoxyimino-2-aminothiazolylacetyl [e.g., 2-cyclopentyloxyimino-2-(2-aminothiazol-4-yl)acetyl, 2-cyclohexyloxyimino-2-(2-aminothiazol-4-yl)acetyl, 2-cycloheptyloxyimino-2-(2-aminothiazol-4-yl)acetyl, etc.];

protected aminothiazolyl(lower)alkanoyl having a cycloalkoxyimino group, preferably acylaminothiazolyl(lower)alkanoyl having a cycloalkoxyimino group, more preferably 2-cycloalkoxyimino-2-lower alkanoylaminothiazolyl acetyl [e.g., 2-cyclopentyloxyimino-2-(2-formamidothiazol-4-yl)acetyl, 2-cyclohexyloxyimino-2-(2-formamidothiazol-4-yl)acetyl, 2-cycloheptyloxyimino-2-(2-formamidothiazol-4-yl)acetyl, etc.];

aminothiazolyl(lower)alkanoyl having a cyclo(lower)-alkenyloxyimino, more preferably 2-cyclo(lower)-alkenyloxyimino-2-aminothiazolylacetyl [e.g., 2-(2-cyclopenten-1-yl)oxyimino-2-(2-aminothiazol-4-yl)acetyl, 2-(2-cyclohexen-1-yl)oxyimino-2-(2-aminothiazol-4-yl)-acetyl, etc.];

protected aminothiazolyl(lower)alkanoyl having a cyclo(lower)alkenyloxyimino, preferably acylaminothiazolyl(lower)alkanoyl having a cyclo(lower)alkenyloxyimino, more preferably 2-cyclo(lower)alkenyloxyimino-2-lower alkanoylaminothiazolylacetyl [e.g., 2-(2-cyclopenten-1-yl)oxyimino-2-(2-formamidothiazol-4-yl)-acetyl, 2-(2-cyclohexen-1-yl)oxyimino-2-(2-formamidothiazol-4-yl)acetyl, etc.];

aminothiadiazolyl(lower)alkanoyl having a lower alkoxyimino group, more preferably 2-lower alkoxyimino-2-aminothiadiazolylacetyl [e.g., 2-methoxyimino-2-(5-amino-1,2,4-thiadiazol-3-yl)acetyl, 2-ethoxyimino-2-(5-amino-1,2,4-thiadiazol-3-yl)acetyl, 2-propoxyimino-2-(5-amino-1,2,4-thiadiazol-3-yl)acetyl, 2-hexyloxyimino-2-(5-amino-1,2,4-thiadiazol-3-yl)acetyl, etc.];

protected aminothiadiazolyl(lower)alkanoyl having a lower alkoxyimino group, preferably acylaminothiadiazolyl(lower)alkanoyl having a lower alkoxyimino group, more preferably 2-lower alkoxyimino-2-lower alkanoylaminothiadiazolylacetyl [e.g., 2-methoxyimino-2-(5-formamido-1,2,4-thiadiazol-3-yl)-acetyl, etc.];

aminothiazolyl(lower)alkanoyl having an ar(lower)alkoxyimino group, more preferably 2-phenyl(lower)-alkoxyimino-2-aminothiazolylacetyl [e.g., 2-benzyloxyimino-2-(2-aminothiazol-4-yl)acetyl, etc.];

protected aminothiazolyl(lower)alkanoyl having an ar(lower)alkoxyimino group, preferably acylaminothiazolyl(lower)alkanoyl having a phenyl(lower)alkoxyimino group, more preferably 2-phenyl(lower)alkoxyimino-2-lower alkanoylaminothiazolylacetyl [e.g., 2-benzyloxyimino-2-(2-formamidothiazol-4-yl)acetyl, etc.];

aminothiazolyl(lower)alkanoyl having a carboxy(lower)alkoxyimino group, more preferably 2-carboxy(lower)alkoxyimino-2-aminothiazolylacetyl [e.g., 2-carboxymethoxyimino-2-(2-aminothiazol-4-yl)acetyl, 2-(2-carboxyethoxyimino)-2-(2-aminothiazol-4-yl)acetyl, 2-(3-carboxypropoxyimino)-2-(2-aminothiazol-4-yl)acetyl, etc.];

aminothiazolyl(lower)alkanoyl having a protected carboxy(lower)alkoxyimino group, preferably aminothiazolyl(lower)alkanoyl having a lower alkoxycarbonyl(lower)alkoxyimino group, more preferably 2-lower alkoxycarbonyl(lower)alkoxyimino-2-aminothiazolylacetyl [e.g., 2-methoxycarbonylmethoxyimino-2-(2-aminothiazol-4-yl)acetyl, 2-t-butoxycarbonylmethoxyimino-2-(2-aminothiazol-4-yl)acetyl, etc.];

protected aminothiazolyl(lower)alkanoyl having a carboxy(lower)alkoxyimino group, preferably acylaminothiazolyl(lower)alkanoyl having a carboxy(lower)-alkoxyimino group, more preferably 2-carboxy(lower)alkoxyimino-2-lower alkanoylaminothiazolylacetyl [e.g., 2-carboxymethoxyimino-2-(2-formamidothiazol-4-yl)-acetyl, 2-(2-carboxyethoxyimino)-2-(2-formanidothiazol-4-yl)acetyl, 2-(3-carboxypropoxyimino)-2-(2-formamidothiazol-4-yl)acetyl, etc.]; and protected aminothiazolyl(lower)alkanol having a protected carboxy(lower)alkoxyimino group, preferably acylaminothiazolyl(lower)alkanoyl having a lower alkoxycarbonyl(lower)alkoxyimino group, more preferably 2-lower alkoxycarbonyl(lower)alkoxyimino-2-lower alkanoylaminothiazolylacetyl [e.g., 2-methoxycarbonylmethoxyimino-2-(2-formamidothiazol-4-yl)acetyl, 2-t-butoxycarbonylmethoxyimino-2-(2-formamidothiazol-4-yl)acetyl, etc.].

amino thiadiazolyl(lower)alkanoyl having a cycloalkoxyimino group, more preferably 2-cycloalkoxyimino-2-aminothiadiazolylacetyl [e.g., 2-cyclopentyloxyimino-2-(5-amino-1,2,4-thiadiazol-3-yl)acetyl, 2-cyclohexyloxyimino-2-(5-amino-1,2,4-thiadiazol-3-yl)acetyl, 2-cycloheptyloxyimino-2-(5-amino-1,2,4-thiadiazol-3-yl)-acetyl, etc.];

protected aminothiadiazolyl(lower)alkanoyl having a cycloalkoxyimino group, preferably acylaminothiadiazolyl(lower)alkanoyl having a cycloalkoxyimino group, more preferably 2-cycloalkoxyimino-2-lower alkanoylaminothiadiazolyl acetyl [e.g., 2-cyclopentyloxyimino-2-(5-formamido-1,2,4-thiadiazol-3-yl)acetyl, 2-cyclohexyloxyimino-2-(5-formamido-1,2,4-thiadiazol-3-yl)acetyl, 2-cycloheptyloxyimino-2-(5-formamido-1,2,4-thiadiazol-3-yl)acetyl, etc.];

aminothiadiazolyl(lower)alkanoyl having a cyclo(lower)alkenyloxyimino, more preferably 2-cyclo(lower)-alkenyloxyimino-2-aminothiadiazolylacetyl [e.g., 2-(2-cyclopenten-1-yl)oxyimino-2-(5-amino-1,2,4-thiadiazol-3-yl)acetyl, 2-(2-cyclohexen-1-yl)oxyimino-2-(5-amino-1,2,4-thiadiazol-3-yl)acetyl, etc.];

protected aminothiadiazolyl(lower)alkanoyl having a cyclo(lower)alkenyloxyimino, preferably acylaminothiadiazolyl(lower)alkanoyl having a cyclo(lower)alkenyloxyimino, more preferably 2-cyclo(lower)alkenyloxyimino-2-lower alkanoylaminothiadiazolylacetyl [e.g., 2-(2-cyclopenten-1-yl)oxyimino-2-(5-formamido-1,2,4-thiadiazol-3-yl)acetyl, 2-(2-cyclohexen-1-yl)oxyimino-2-(5-formamido-1,2,4-thiadiazol-3-yl)acetyl, etc.];

aminothiadiazolyl(lower)alkanoyl having a carboxy(lower)alkoxyimino group, more preferably 2-carboxy(lower)alkoxyimino-2-aminothiadiazolylacetyl [e.g., 2-carboxymethoxyimino-2-(5-amino-1,2,4-thiadiazol-3-yl)acetyl, 2-(2-carboxyethoxyimino)-2-(5-amino-1,2,4-thiadiazol-3-yl)acetyl, 2-(3-carboxypropoxyimino)-2-(5-amino-1,2,4-thiadiazol-3-yl)acetyl, etc.];

aminothiadiazolyl(lower)alkanoyl having a protected carboxy(lower)alkoxyimino group, preferably aminothiadiazolyl(lower)alkanoyl having a lower alkoxycarbonyl(lower)alkoxyimino group, more preferably 2-lower alkoxycarbonyl(lower)alkoxyimino-2-aminothiadiazolylacetyl [e.g., 2-methoxycarbonylmethoxyimino-2-(5-amino-1,2,4-thiadiazol-3-yl)acetyl, 2-t-butoxycarbonylmethoxyimino-2-(5-amino-1,2,4-thiadiazol-3-yl)acetyl, etc.];

protected aminothiadiazolyl(lower)alkanoyl having a carboxy(lower)alkoxyimino group, preferably acylaminothiadiazolyl(lower)alkanoyl having a carboxy(lower)-alkoxyimino group, more preferably 2-carboxy(lower)-alkoxyimino-2-lower alkanoylaminothiadiazolylacetyl [e.g., 2-carboxymethoxyimino-2-(5-formamido-1,2,4-thiadiazol-3-yl)acetyl, 2-(2-carboxyethoxyimino)-2-(5-formamido-1,2,4-thiadiazol-3-yl)acetyl, 2-(3-carboxypropoxyimino-2-(5-formamido-1,2,4-thiadiazol-3-yl)-acetyl, etc.];

protected aminothiadiazolyl(lower)alkanoyl having a protected carboxy(lower)alkoxyimino group, preferably acylaminothiadiazolyl(lower)alkanoyl having a lower alkoxycarbonyl(lower)alkoxyimino group, more preferably 2-lower alkoxycarbonyl(lower)alkoxyimino-2-loweralkanoylaminothiadiazolylacetyl [e.g. 2-methoxycarbonylmethoxyimino-2-(5-formamido-1,2,4-thiadiazol-3-yl)acetyl, 2-t-butoxycarbonylmethoxyimino-2-(5-formamido-1,2,4-thiadiazol-3-yl)acetyl, etc.];

arylglycyl, more preferably phenylglycyl;

ar(lower)alkanoyl having a protected amino group, preferably phenyl(lower)alkanoyl having an acylamino group, more preferably phenyl(lower)alkanoyl having lower alkoxycarbonylamino group (e.g. 2-tert-butoxycarbonylamino-2-phenylacetamide, etc.);

lower alkenylthio(lower)alkanoyl (e.g. vinylthioacetyl, allylthioacetyl, allylthiopropionyl, butenylthioacetyl, etc.).

$R^2$ is carboxy or ar(lower)alkoxycarbonyl, more preferably mono(or di)-phenyl(lower)alkoxycarbonyl (e.g. benzyloxycarbonyl, benzhydryloxycarbonyl, etc.);

$R^3$ is 1-(lower alkynyl)-1H-tetrazol-5-yl [e.g. 1-(2-propynyl)-1H-tetrazol-5-yl, 1-(1-methyl-2-propynyl)-1H-tetrazol-5-yl, 1-(1 or 2 or 3-butynyl)-1H-tetrazol-5-yl, etc.] or 2-(lower alkynyl)-2H-tetrazol-5-yl [e.g. 2-(2-propynyl)-2H-tetrazol-5-yl, 2-(1-methyl-2-propynyl)-2H-tetrazol-5-yl, 2-(1 or 2 or 3-butynyl)-2H-tetrazol-5-yl, etc.];

X is —S— or

The processes for preparing the object compounds of the present invention are explained in detail in the following.

Process 1

The object compound (I) or a salt thereof can be prepared by reacting the compound (II) or a salt thereof with the compound (III) or its reactive derivative at the mercapto group or a salt thereof.

Suitable salts of the compound (II) and (III) are each referred to the ones exemplified for the compound (I).

Suitable reactive derivative at the mercapto group in the compound (III) may include a metal salt such as an alkali metal salt (e.g. sodium salt, potassium salt, etc.), an alkaline earth metal salt (e.g., magnesium salt, etc.) or the like.

The reaction is usually carried out in a solvent such as water, acetone, chloroform, nitrobenzene, methylene chloride, ethylene chloride, dimethylformamide, methanol, ethanol, ether, tetrahydrofuran or any other conventional solvents which do not adversely influence the reaction, preferably in ones having strong polarity, which may be used as a mixture with water.

When the compound (II) and/or the compound (III) are used in free form in the reactions, the reaction is preferably carried out in the presence of a base such as alkali metal hydroxide, alkali metal carbonate, alkali metal bicarbonate, trialkylamine, pyridine, or a Lewis acid such as boron trifluoride or the like, and preferably carried out around neutral conditions. The reaction temperature is not critical and the reaction is usually carried out at ambient temperature or under warming.

The present invention includes, within its scope, the cases that a protected amino and/or a protected carboxy group are converted into the corresponding free amino and/or the free carboxy group during the reaction or the post-treating step of the present process.

Process 2

The compound (I) or a salt thereof can be prepared by reacting the compound (IV) or a salt thereof with the compound (V).

Suitable salts of the compound (IV) can be referred to the ones as exemplified for the compound (I).

The present reaction may be carried out in the presence of an organic or inorganic base such as alkali metal bicarbonate, alkali metal carbonate, alkaline earth metal bicarbonate, alkaline earth metal carbonate, alkali metal hydroxide, alkaline earth metal hydroxide, tri(lower)alkylamine, N,N-di(lower)alkyl arylamine, pyridine or the like. In case that there are obtained a mixture of isomers wherein lower alkynyl groups are introduced in the different positions of the tetrazolyl ring, the respective isomers can be separated from the reaction mixture by conventional procedures such as chromatography or the like. The present reaction is usually carried out in a solvent such as N,N-dimethylformamide, tetrahydrofuran or any other solvents which do not adversely affect the reaction. The reaction temperature is not critical and the reaction is preferably carried out under cooling to warming.

Process 3

The compound (Ia) or a salt thereof can be prepared by reducing the compound (Ib) or a salt thereof.

Suitable salts of the compound (Ib) can be referred to the ones as exemplified for the compound (I).

The present reduction can be carried out by a conventional method which is applied to the transformation of

into —S—, for example, by using phosphorus trichloride, a combination of stannous chloride and acetyl chloride, a combination of an alkali metal iodide (e.g. sodium iodide, etc.) and trihaloacetic anhydride (e.g., trifluoroacetic anhydride, etc.), and the like.

The present reduction is usually carried out in a solvent such as acetone, dioxane, acetonitrile, benzene, hexane, chloroform, methylene chloride, ethylene chloride, tetrahydrofuran, ethyl acetate, N,N-dimethylformamide or any other solvents which do not adversely affect the reaction.

The reaction temperature is not critical and the reaction is usually carried out under cooling or at ambient temperature.

Process 4

The object compound (Ic) or a salt thereof can be prepared by subjecting the compound (Id) or a salt thereof to elimination reaction of the amino protective group.

The present elimination reaction is carried out in accordance with a conventional method such as hydrolysis; reduction; deacylation using Lewis acid; deacylation method by reacting the compound (Id) with iminohalogenating agent and then with iminoetherifying agent, and, if necessary, subjecting the resulting compound to hydrolysis; or the like.

Among these methods, "the deacylation method by reacting the compound (Id) with iminohalogenating agent and then with iminoetherifying agent, and, if necessary, subjecting the resulting compound to hydrolysis" is preferable method.

Suitable iminohalogenating agent may include phosphorus halide (e.g. phosphorus trichloride, phosphorus pentachloride, phosphorus tribromide, phosphorus pentabromide, etc.), phosphorus oxychloride, thionyl chloride, phosgene and the like. The reaction temperature is not critical, and the reaction is usually carried out at ambient temperature or under cooling.

In case that the compound (Id) has a free carboxy group at the 4-position, this reaction is preferably carried out by protecting the free carboxy group with a silylating agent (e.g., trimethylsilyl chloride, trimethylsilylacetamide, bis(trimethylsilyl)acetamide, etc.) before this reaction.

Suitable iminoetherifying agent reacted with thus obtained reaction product may include an alcohol, metal alkoxide and the like. Suitable alcohol may include alkanol (e.g. methanol, ethanol, propanol, isopropanol, butanol, t-butanol, etc.) which may be substituted with alkoxy (e.g. methoxy, ethoxy, propoxy, isopropoxy, butoxy, etc.). Suitable metal alkoxide may include alkali metal alkoxide (e.g., sodium alkoxide, potassium alkoxide, etc.), alkaline earth metal alkoxide (e.g., calcium alkoxide, barium alkoxide, etc.), and the like. The reaction temperature is not critical, and the reaction is usually carried out under cooling or at ambient temperature.

Thus obtained product is, if necessary, subjected to hydrolysis. The hydrolysis can readily be carried out by pouring the reaction mixture obtained above into water, but there may be previously added a hydrophilic solvent (e.g., methanol, ethanol, etc.), a base (e.g., alkali metal bicarbonate, trialkylamine, etc.) or an acid (e.g., diluted hydrochloric acid, acetic acid, etc.) to the water.

The reaction temperature is not critical and may be suitably selected in accordance with the kind of the protective group of the amino group and the elimination method as mentioned above, and the present reaction is preferably carried out under a mild condition such as under cooling, at ambient temperature or slightly elevated temperature.

The present invention includes, within its scope, the case that the protected carboxy is transformed into the free carboxy group according to reaction conditions and kinds of the protective groups in the course of the reaction or in post-treatment. The hydrolysis may include a method using an acid or base and the like. These methods may be selected depending on the kind of the amino protective groups to be eliminated.

Suitable acid may include an organic or an inorganic acid, for example, formic acid, trifluoroacetic acid, benzenesulfonic acid, p-toluenesulfonic acid, hydrochloric acid and the like. The acid suitable for the reaction can be selected according to the kind of amino protective group to be eliminated. When the elimination reaction is conducted with the acid, it can be carried out in the presence or absence of a solvent. Suitable solvent may include an organic solvent, water or a mixed solvent thereof. When trifluoroacetic acid is used, the deacylation reaction may be preferably carried out in the presence of anisole.

Suitable base may include, for example, an inorganic base such as alkali metal hydroxide (e.g., sodium hydroxide, potassium hydroxide, etc.), alkaline earth metal hydroxide (e.g., magnesium hydroxide, calcium hydroxide, etc.), alkali metal carbonate (e.g., sodium carbonate, potassium carbonate, etc.), alkaline earth metal carbonate (e.g., magnesium carbonate, calcium carbonate, etc.), alkali metal bicarbonate (e.g., sodium bicarbonate, potassium bicarbonate, etc.), alkali metal acetate (e.g., sodium acetate, potassium acetate, etc.), alkaline earth metal phosphate (e.g., magnesium phosphate, calcium phosphate, etc.), alkali metal hydrogen phosphate (e.g., disodium hydrogen phosphate, dipotassium hydrogen phosphate, etc.), or the like, and an organic base such as trialkylamine (e.g., trimethylamine, triethylamine, etc.), picoline, N-methylpyrrolidine, N-methylmorpholine, 1,5-diazabicyclo[4,3,0]non-5-ene, 1,4-diazabicyclo[2,2,2]octane, 1,5-diazabicyclo[5,4,0]-undecene-5 or the like. The hydrolysis using a base is often carried out in water or a hydrophilic organic solvent or a mixed solvent thereof.

The reduction may include, for example, reduction with an alkali metal borohydride (e.g., sodium borohydride, etc.), catalytic reduction and the like.

The deacylation reaction using Lewis acid is carried out substantially in the same manner as described in Process 6.

Process 5

The object compound (In) or a salt thereof can be prepared by reacting the compound (Ic) or its reactive derivatives at the amino group or a salt thereof with an acylating agent.

Suitable reactive derivatives at the amino group of the compound (Ic) may include conventional ones such as Schiff's base type imino or its tautomeric enamine type derivatives formed by the reaction of the compound (Ic) with a carbonyl compound (e.g. aldehyde, ketone, etc.), isocyanate;

silyl derivatives formed by the reaction of the compound (Ic) with a silyl compound [e.g., bis(trimethylsilyl)acetamide, trimethylsilylacetamide, etc.];

derivatives formed by the reaction of the compound (Ic) with phosphorus trichloride or phosgene, or the like.

Suitable salts of the compound (Ic) can be referred to the ones as exemplified for the compound (I).

The acylating agent to be used for the present reaction may include one of the formulae:

$$R^8-OH \qquad (XVI)$$

wherein $R^8$ is acyl, or its reactive derivatives or a salt thereof.

Suitable acyl can be referred to those exemplified hereinbefore.

Suitable reactive derivatives of the compound (XVI) may include an acid halide, an acid anhydride, an activated amide, an activated ester, and the like. The suitable example may be an acid chloride; an acid azide;

a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid or trichloroacetic acid, etc.) or aromatic carboxylic acid (e.g., benzoic acid, etc.);

a symmetrical acid anhydride;

an activated amide with imidazole, 4-substituted imidazole, dimethylpyrazole, triazole or tetrazole;

an activated ester [e.g., cyanomethyl ester, methoxymethyl ester, dimethyliminomethyl [(CH$_3$)$_2$N$^+$=CH-] ester, vinyl ester, propargyl ester, p-nitrophenyl ester, 2,4-dinitrophenyl ester, trichlorophenyl ester, pentachlorophenyl ester, mesyl-phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or an ester with N,N-dimethylhydroxylamine, 1-hydroxy-2-(1H)pyridone, N-hydroxysuccinimide, N-hydroxyphthalimide or 1-hydroxy-6-chloro-1H-benzotriazole, and the like.

These reactive derivatives can optionally be selected from them according to the kind of the compound (XVI) to be used.

The salt of the compound (XVI) may be salt with an inorganic base such as an alkali metal salts (e.g., sodium or potassium salt) or an alkaline earth metal salt (e.g., calcium or magnesium salt), a salt with an organic base such as trimethylamine, triethylamine, dicyclohexylamine or the like.

The present reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. Among these solvents, hydrophilic solvents may be used in a mixture with water.

When the acylating agent is used in a free acid form or its salt form in the reaction, the reaction is preferably carried out in the presence of a conventional condensing agent such as carbodiimide compound (e.g., N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), N,N'-carbonylbis(2-mesylimidazole), pentamethtyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, N-ethylbenzisoxazolium salt, N-ethyl-5-phenyl-isoxazolium-3'-sulfonate, 1-(p-chlorobenzenesulfonyloxy)-6-chloro-1H-benzotriazole, Vilsmeier reagent [e.g., (chloromethylene)dimethylammonium chloride, a compound formed by the reaction of dimethylformamide with phosphorus oxychloride, etc.] or the like.

The reaction may also be carried out in the presence of an inorganic or an organic base such as an alkali metal bicarbonate, alkali metal carbonate, tri(lower)alkylamine, pyridine, di(lower)alkylpyridine, N-(lower)alkylmorphorine, N,N-di(lower)alkylbenzylamine, N,N-di(lower)alkylaniline, or the like. When the base or the condensing agent is in liquid, it can be used also as a solvent. The reaction temperature is not critical, and the reaction is usually carried out under cooling or at ambient temperature.

Process 6

The object compound (Ie) or a salt thereof can be prepared by subjecting the compound (If) or a salt thereof to elimination reaction of the carboxy protective group.

Suitable salt of the compound (If) can be referred to the acid addition salt exemplified for the compound (I).

In the present elimination reaction, all conventional methods used in the elimination reaction of the carboxy protective group, for example, hydrolysis, reduction, elimination using Lewis acid, etc. are applicable. When the carboxy protective group is an ester, it can be eliminated by hydrolysis or elimination using Lewis acid. The hydrolysis is preferably carried out in the presence of a base or an acid. Suitable base may include an inorganic base and an organic base as aforementioned.

Suitable acid may include an organic acid (e.g. formic acid, acetic acid, propionic acid, etc.) and an inorganic acid (e.g., hydrochloric acid, hydrobromic acid, sulfuric acid, etc.).

The present hydrolysis is usually carried out in an organic solvent, water or a mixed solvent thereof.

The reaction temperature is not critical, and it may suitably be selected in accordance with the kind of the protective group of the carboxy and the elimination method.

The elimination using Lewis acid is preferable to eliminate substituted or unsubstituted ar(lower)-alkyl ester and carried out by reacting the compound (If) or a salt thereof with Lewis acid such as boron trihalide (e.g., boron trichloride, boron trifluoride, etc.), titanium tetrahalide (e.g., titanium tetrachloride, titanium tetrabromide, etc.), tin tetrahalide (e.g., tin tetrachloride, tin tetrabromide etc.), aluminum halide (e.g., aluminum chloride, aluminum bromide, etc.), trihaloacetic acid (e.g., trichloroacetic acid, trifluoroacetic acid, etc.) or the like. This elimination reaction is preferably carried out in the presence of cation trapping agents (e.g., anisole, phenol, etc.) and is usually carried out in a solvent such as nitroalkane (e.g., nitromethane, nitroethane, etc.), alkylene halide (e.g., methylene chloride, ethylene chloride, etc.), diethyl ether, carbon disulfide or any other solvent which does not adversely affect the reaction. These solvents may be used as a mixture thereof. The reaction temperature is not critical, and the reaction is usually carried out under cooling, at ambient temperature or under warming.

The reductive elimination can be applied preferably for elimination of the protective group such as halo(lower)alkyl (e.g., 2-iodoethyl, 2,2,2-trichloroethyl, etc.), ester, ar(lower)alkyl (e.g., benzyl, etc.) ester or the like. The reduction method applicable for the elimination reaction may include, for example, reduction by using a combination of a metal (e.g., zinc, zinc amalgam, etc.) or a salt of chrome compound (e.g., chromous chloride, chromous acetate, etc.) and an organic or inorganic acid (e.g., acetic acid, propionic acid, hydrochloric acid, etc.); and conventional catalytic reduction in the presence of a conventional metallic catalyst (e.g., palladium carbon, Raney nickel, etc.).

The present elimination reaction of the carboxy protective group includes, within its scope, the cases that protected amino group in the compound (If) is transformed into free amino group according to reaction conditions and kinds of the protective groups in the course of the reaction and/or in post-treatment of the reaction.

Process 7

The object compound (Ig) or a salt thereof can be prepared by subjecting the compound (Ih) or a salt thereof to the elimination reaction of the amino-protective group.

Suitable salts of the compound (Ih) may include a metal salt, ammonium salt, an organic amine salt and the like exemplified for the compound (I).

The present elimination reaction is carried out in accordance with a conventional method such as hydrolysis; reduction; elimination using a Lewis acid; a method by reacting the compound (Ih), wherein the protective group is an acyl group, with an iminohalogenating agent and then with an iminoetherifying agent, and, if necessary, subjecting the resulting compound to hydrolysis; or the like.

The hydrolysis may include a method using an acid or base or hydrazine and the like. These methods may be selected depending on the kind of the protective groups to be eliminated.

Among these methods, hydrolysis using an acid is one of the common and preferable methods for elimination of an acyl group.

Suitable acid may include an organic or an inorganic acid, for example, formic acid, trifluoroacetic acid, benzenesulfonic acid, p-toluenesulfonic acid, hydrochloric acid and the like, and preferable acids are those which can easily be removed from the reaction mixture by a conventional manner such as distillation under reduced pressure, for example, formic acid, trifluoroacetic acid, hydrochloric acid, etc. The acid suitable for the reaction can be selected according to the kind of protective groups to be eliminated. When the elimination reaction is conducted with an acid, it can be carried out in the presence or absence of a solvent. Suitable solvents may include an organic solvent, water or a mixed solvent thereof. When trifluoroacetic acid is used, the elimination reaction may preferably be carried out in the presence of anisole.

The hydrolysis using hydrazine is commonly applied for eliminating the protective groups, for example, succinyl or phthaloyl.

The hydrolysis using a base is preferably applied for elimination of an acyl group. Suitable base may include, for example, an inorganic base such as alkali metal hydroxide (e.g., sodium hydroxide, potassium hydroxide, etc.), alkaline earth metal hydroxide (e.g., magnesium hydroxide, calcium hydroxide, etc.), alkali metal carbonate (e.g., sodium carbonate, potassium carbonate, etc.), alkaline earth metal carbonate (e.g., magnesium carbonate, calcium carbonate, etc.), alkali metal bicarbonate (e.g., sodium bicarbonate, potassium bicarbonate, etc.), alkali metal acetate (e.g., sodium acetate, potassium acetate, etc.), alkaline earth metal phosphate (e.g., magnesium phosphate, calcium phosphate, etc.), alkali metal hydrogen phosphate (e.g., disodium hydrogen phosphate, dipotassium hydrogen phosphate, etc.), or the like, and an organic base such as trialkylamine (e.g., trimethylamine, triethylamine, etc.), picoline, N-methylpyrrolidine, N-methylmorpholine, 1,5-diazabicyclo[4,3,0]non-5-ene, 1,4-diazabicyclo[2,2,2]octane, 1,5-diazabicyclo[5,4,0]undecene-5 or the like. The hydrolysis using a base is often carried out in water or a hydrophilic organic solvent or a mixed solvent thereof.

Among the protective group, the acyl group can generally be eliminated by hydrolysis as mentioned above or by the other conventional hydrolysis. In case that the acyl group is halo(lower)alkoxycarbonyl or 8-quinolyloxycarbonyl, they are eliminated by treating with a heavy metal such as copper, zinc or the like.

The elimination reaction using a Lewis acid can be referred to that described in Process 6.

The reductive elimination is generally applied for eliminating the protective group, for example, halo(lower or higher)alkoxycarbonyl (e.g. trichloroethoxycarbonyl, etc.), substituted or unsubstituted ar(lower)alkoxycarbonyl (e.g. benzyloxycarbonyl, etc.), etc. Suitable reduction may include, for example, reduction with an alkali metal borohydride (e.g., sodium borohydride, potassium borohydride, etc.), reduction using a combination of a metal (e.g., zinc, zinc amalgam, etc.) and an organic or inorganic acid (e.g., acetic acid, propionic acid, hydrochloric acid, etc.), catalytic reduction, and the like.

Suitable iminohalogenating agents used in a method as mentioned above may include phosphorus halide (e.g., phosphorus trichloride, phosphorus pentachloride, phosphorus tribromide, phosphorus pentabromide, etc.), phosphorus oxychloride, thionyl chloride, phosgene and the like. The reaction temperature is not critical, and the reaction is usually carried out at ambient temperature or under cooling. Suitable iminoetherifying agents reacted with thus obtained reaction product may include an alcohol, metal alkoxide and the like. Suitable alcohol may include alkanol (e.g., methanol, ethanol, propanol, isopropanol, butanol, tert-butanol, etc.) which may be substituted with alkoxy (e.g., methoxy, ethoxy, propoxy, isopropoxy, butoxy, etc.). Suitable metal alkoxide may include alkali metal alkoxide (e.g., sodium alkoxide, potassium alkoxide, etc.), alkaline earth metal alkoxide (e.g., calcium alkoxide, barium alkoxide, etc.) and the like.

The reaction temperature is not critical, and the reaction is usually carried out under cooling at ambient temperature or under warming.

Process 8

The compound (Ii) or a salt thereof can be prepared by reducing the compound (Ij) or a salt thereof.

Suitable salts of the compound (Ij) are referred to the ones exemplified for the compound (I).

The present reduction can be carried out by a conventional method which is applied to the transformation of an oxo group into a hydroxy group. Among them, the preferred method is the reduction method as described in Process 7.

Process 9

The object compound (Ij) or a salt thereof can be prepared by subjecting the compound (Ik) or a salt thereof to elimination reaction of the protective group of the hydroxy.

Suitable salt of the compound (Ik) can be referred to the ones as exemplified for the compound (I).

The present elimination reaction is carried out in accordance with a conventional method such as hydrolysis, reduction, elimination using a Lewis acid or the like. The hydrolysis may include a method using an acid or base and the like. These methods may be selected depending on kind of the protective groups to be eliminated. Among them, the preferred method is the hydrolysis using an acid and suitable acid may include, for example, formic acid, trifluoroacetic acid, benzenesulfonic acid, p-toluenesulfonic acid, hydrochloric acid, and the like. The acid suitable for the reaction can be selected according to the protective group to be eliminated and other factors. The hydrolysis using an acid may be carried out in the presence of a solvent, such as a hydrophilic organic solvent, water or a mixed solvent thereof. The reaction temperature is not critical and the reaction is usually carried out under cooling to warming.

The present invention includes, within its scope, the cases that the protected carboxy group is transformed into the free carboxy group and/or the protected amino group is transformed into the free amino group according to the reaction conditions and kinds of the protective groups in the course of the reaction and/or in post-treating of the reaction.

Process 10

The compound (II) or a salt thereof can be prepared by subjecting the compound (Im) or a salt thereof to the elimination reaction of the carboxy protective group.

Suitable salts of the compound (Im) are referred to the ones exemplified for the compound (I).

The present elimination reaction can be carried out in a similar manner to that of aforementioned Process 6.

The processes for preparing the starting compounds (III) and (IV) are explained in details as follows.

Suitable salts of the compounds (IVa), (VI), (VII), (IX), (XI), (XII), (XIII) and (XV) can be referred to the ones as exemplified for the compound (I).

Process A (1): (IX)+(VIII)→(VII)

The compound (VII) or a salt thereof can be prepared by reacting the compound (IX) or a salt thereof with the compound (VIII).

The present reaction may be carried out in the presence of an organic or inorganic base as mentioned in Process 2.

The present reaction is usually carried out in a solvent such as water, tetrahydrofuran, alcohol (e.g., methanol, ethanol, etc.) or a mixed solvent thereof, or any other solvents which do not adversely affect the reaction.

The reaction temperature is not critical and the reaction is preferably carried out under cooling to warming or heating.

(2): (VII)→(VI) 

The compound (VI) can be prepared by subjecting the compound (VII) or a salt thereof to the diazotization reaction.

The present diazotization can be carried out by using a conventional diazotizing agent such as nitrous acid, [which may be prepared in situ by reaction of an alkali metal nitrite with an acid (e.g., hydrochloric acid, etc)], nitrosylchloride, lower alkyl nitrite (e.g., t-butyl nitrite, etc.) or the like.

The present reaction may be carried out in the presence of an organic or inorganic acid such as hydrochloric acid, acetic acid or the like.

The present reaction may be carried out in a solvent such as benzene, toluene, alcohol (e.g., methanol, ethanol, etc.) or any other solvents which do not adversely affect the reaction.

The reaction temperature is not critical and the reaction is preferably carried out under cooling or at ambient temperature.

Process B: (XI)+(V)→(X) 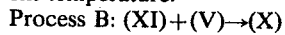

The compound (X) can be prepared by reacting the compound (XI) or a salt thereof with the compound (V).

The present introduction reaction can be carried out in a similar manner to that of aforementioned Process 2.

Process C (1): (XIII)→(XII) 

The compound (XII) or a salt thereof can be prepared by subjecting the compound (XIII) or a salt thereof to the elimination reaction of the aralkyl group.

The present elimination reaction may be carried out by a method using sodium metal as well as conventional methods such as elimination using Lewis acid as mentioned in Process 4, hydrolysis using an organic or inorganic acid (e.g., acetic acid, hydrobromic acid, iodic acid, etc.) or the like. The present reaction is usually carried out in a solvent such as pyridine or any other solvents which do not adversely affect the reaction. The reaction temperature is not critical and the reaction is preferably carried out under cooling to warming.

(2): (X)→(III) 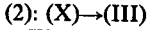

The compound (III) or a salt thereof can be prepared by subjecting the compound (X) to the elimination reaction of the mercapto-protective group.

The present elimination reaction may be carried out in accordance with a conventional method such as hydrolysis using an organic or inorganic acid (e.g., acetic acid, hydrobromic acid, etc.), elimination using Lewis acid as mentioned in Process 6 or the like.

The present reaction may be carried out in a solvent such as water or any other solvents which do not adversely affect the reaction.

The reaction temperature is not critical and the reaction is preferably carried out under cooling to heating.

Process D (1): (XII)+(VIII)→(XIII), 2): (III)+(XIV)→(X) 

The compounds (XIII) or a salt thereof and (X) can be prepared by reacting the compounds (XII) or a salt thereof and (III) or a salt thereof with the compounds (VIII) and (XIV), respectively.

The present introduction reaction can be carried out in a similar manner to that of aforementioned Process A 1).

Process E: (XV)+(XII)→(IVa)

The compound (IVa) or a salt thereof can be prepared by reacting the compound (XV) or a salt thereof with the compound (XII) or its reactive derivative at the mercapto group or a salt thereof.

The present reaction can be carried out in a similar manner to that of aforementioned Process 1.

The present invention includes, within its scope, the cases that protected amino and/or protected carboxy and/or protected hydroxy group(s) are transformed into the corresponding free amino and/or carboxy and-/or hydroxy group(s) according to the reaction conditions and kinds of the protective groups in the course of the aforementioned reactions and/or in post-treatment of the reactions in Processes 1 to 10 and A to E.

In the aforementioned reactions and/or the post-treating of the reactions in Processes 1 to 10 and A to E of the present invention, the aforementioned geometrical isomer and/or tautomeric isomer may occasionally be transformed into the other geometrical isomer and/or tautomeric isomer and such cases are to be also included in the scope of the present invention.

In case that the object compound (I) has a free carboxy group and/or a free amino group, it may be transformed into its pharmaceutically acceptable salt as aforementioned by a conventional method.

The object compound (I) of the present invention exhibits high antimicrobial activity and inhibits the growth of a number of microorganisms including pathogenic Gram-positive and Gram-negative bacteria.

For therapeutic administration, the cephalosporin compounds according to the present invention are used in the form of pharmaceutical preparation which contain said compounds in admixture with a pharmaceutically acceptable carriers such as an organic or inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives.

While the dosage of the compounds may vary from and also depend upon the age and condition of the patient, an average single dose of about 50 mg., 100 mg., 250 mg., and 500 mg. of the compounds according to the present invention has proved to be effective for treating of infectious diseases caused by a number of pathogenic bacteria. In general amounts, daily dose between 1 mg/body and about 1000 mg/body or even more may be administered.

Now, in order to show the utility of the object compounds (I), test data on anti-microbial activity of a representative compound of the present invention are shown below.

Test method

One loopful of an overnight culture of each test strain in Trypticase-soy broth ($10^8$ viable cells per ml.) was streaked on heart infusion agar (HI-agar) containing graded concentrations of antibiotics, and the minimal inhibitory concentration (MIC) was expressed in terms of μg/ml after incubation at 37° C. for 20 hours.

Test compound (1) 7-[2-Methoxyimino-2-(2-aminothiazol-4-yl)-acetamido]-3-[1-(2-propynyl)-1H-tetrazol-5-yl]thiomethyl-3-cephem-4-carboxylic acid (syn isomer).

(2) 7-[2-Methoxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer).

(3) 7-[2-Ethoxyimino-2-(2-aminothiazol-4-yl)-acetamido]-3-[1-(2-propynyl)-1H-tetrazol-5-yl]thiomethyl-3-cephem-4-carboxylic acid (syn isomer).

(4) 7-[2-(1-Cyclopenten-1-yl)oxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer).

| Test Microorganism | Test result M.I.C. (μg/ml) | | | |
|---|---|---|---|---|
| | Compound (1) | Compound (2) | Compound (3) | Compound (4) |
| Bacillus subtilis ATCC 6633 | 0.780 | 1.560 | 0.780 | 0.390 |
| Escherichia coli 31 | 0.025 | 0.025 | 0.025 | 0.050 |
| Pseudomonas aeruginosa NCTC-10490 | 6.250 | 3.130 | 3.130 | 3.130 |

The following Preparations and Examples are given for the purpose of illustrating the present invention.

Preparation 1

(1) A mixture of thiosemicarbazide (300 g), benzylchloride (416.7 g) in ethanol (1.5 l) was refluxed with stirring for an hour. The reaction mixture was cooled and evaporated under reduced pressure to give a crude oily product of 3-benzylisothiosemicarbazide hydrochloride.

Thus obtained crude product was used in the next step reaction without isolation.

(2) To a solution of the crude product of 3-benzylisothiosemicarbazide hydrochloride from (1) above in water (5 l) were added conc. hydrochloric acid (0.29 l) and benzene (2 l). The resulting mixture was cooled to 5° to 6° C. and thereto was dropwise added a solution of sodium nitrite (249 g) in water (1 l) over a period of an hour keeping the temperature below 15° C. The resulting mixture was stirred for 1.5 to 2 hours at about 10° C. The precipitates were collected by filtration, washed successively with benzene (1 l) and n-hexane (1 l) and then dried to given 5-benzylthio-1H-tetrazole (412.8 g), mp 98° to 100° C.

Preparation 2

A solution of 5-benzylthio-1H-tetrazole (278 g) in pyridine (2.7 l) was stirred at 60° to 70° C. and thereto was added sodium metal (100 g) over a period of 40 to 60 minutes. The resulting mixture was refluxed with stirring for 2.5 hours and then thereto was added methanol (200 ml). The mixture was stirred for 10 to 20 minutes. The reaction mixture was evaporated and the residue was dissolved in a mixture of water (0.8 l) and ethyl acetate (1 l). The solution was treated with activated charcoal (20 g) and the aqueous layer was separated and saturated with sodium chloride. The solution was adjusted to pH 2 with conc. hydrochloric acid and extracted with ethyl acetate (250 to 300 ml×7 to 10). The extract was dried over magnesium sulfate and then evaporated to give crystals of 1H-tetrazole-5-thiol (95.0 g), mp 178° to 180° C. (dec.).

Preparation 3

To a mixture of 1H-tetrazole-5-thiol (27.5 g) and triethylamine (59.9 g) in tetrahydrofuran (550 ml) was added benzhydryl bromide (66.6 g) and then the mixture was refluxed with stirring for 6.5 hours. After the addition of water and ethyl acetate to the reaction mixture, the pH was adjusted to 9.0 with 2 N aqueous solution of sodium hydroxide. The aqueous layer was separated and washed with ethyl acetate. After the addition of ethyl acetate to the washed aqueous layer, the mixture was adjusted to pH 2.0 with 10% hydrochloric acid. The ethyl acetate layer was separated, washed with a saturated aqueous solution of sodium chloride, dried over magnesium sulfate and then evaporated. The residue was pulverized in a mixture of isopropyl ether and n-hexane, collected by filtration, washed with a mixture of isopropyl ether and n-hexane and then dried to give 5-benzhydrylthio-1H-tetrazole (29.62 g), mp 132° to 134° C.

N.M.R. (DMSO-$d_6$, $\delta$): 6.32 (1H, s), 7.21–7.73 (10H, m)

Preparation 4

To a solution of 5-benzhydrylthio-1H-tetrazole (29 g) in tetrahydrofuran (145 ml) were added triethylamine (12.0 g) and 2-propynyl bromide (19.3 g) at room temperature. The resulting mixture was stirred for 2.5 hours at 40° to 45° C. The reaction mixture was filtered and the filtrate was evaporated. The residue was shaken with a mixture of ethyl acetate and water. The ethyl acetate layer was separated, washed with a saturated aqueous solution of sodium chloride, dried over magnesium sulfate and then evaporated. The residual oil (27.7 g) was subjected to column chromatography on silica gel, and eluted with a mixture of n-hexane, chloroform and ethyl acetate (5.5:4.5:0.5), to give 5-benzhydrylthio-2-(2-propynyl)-2H-tetrazole (14.2 g), mp 85° to 86° C.

I.R. (Nujol): 3260, 2150 $cm^{-1}$

N.M.R. (DMSO-$d_6$, $\delta$): 3.66 (1H, t, J=2.5 Hz), 5.61 (2H, d, J=2.5 Hz), 6.20 (1H, s), 7.17–7.66 (10H, m)

The continued elution gave 5-benzhydrylthio-1-(2-propynyl)-1H-tetrazole (8.97 g), mp 92° C.

I.R. (Nujol): 3300, 2150 $cm^{-1}$

N.M.R. (DMSO-$d_6$, $\delta$): 3.66 (1H, t, J=2.5 Hz), 5.34 (2H, d, J=2.5 Hz), 6.23 (1H, s), 7.20–7.66 (10H, m)

Preparation 5

A mixture of 5-benzhydrylthio-1-(2-propynyl)-1H-tetrazole (0.35 g), anisole (0.6 g) and trifluoroacetic acid (3.4 ml) was stirred for 30 minutes at 20° C. and then allowed to stand for 45 minutes. The reaction mixture was filtered and the filter cake was washed with isopropyl ether. The filtrate and the washing were combined and evaporated under reduced pressure. After the addition of the residue to a saturated aqueous solution of sodium bicarbonate precooled to 10° C., the resulting mixture was adjusted to pH 8.5 with 2 N aqueous solution of sodium hydroxide and washed with ethyl acetate. The washed aqueous layer was adjusted to pH 2.5 with 10% hydrochloric acid under ice-cooling and then extracted with ethyl acetate. The extract was washed with a saturated aqueous solution of sodium chloride, dried over magnesium sulfate and evaporated to give 1-(2-propynyl)-1H-tetrazole-5-thiol (95 mg), which is decomposed from 60° to 71° C.

I.R. (Nujol): 3240, 2125 $cm^{-1}$

N.M.R. (DMSO-$d_6$, $\delta$): 3.47 (1H, t, J=2 Hz), 5.08 (2H, d, J=2 Hz)

Preparation 6

A mixture of 5-benzhydrylthio-2-(2-propynyl)-2H-tetrazole (1.05 g), anisole (1.79 g) and trifluoroacetic acid (9.7 ml) was stirred at 22° C. for 1.5 hours, at 35° C. for an hour, at 50° C. for 1.7 hours and then at room temperature for a further 14 hours. The reaction mixture was filtered and the filtrate was evaporated under reduced pressure. To the residue was added a saturated aqueous solution of sodium bicarbonate (10 ml) and the mixture was adjusted to pH 8.5 with 2 N aqueous solution of sodium hydroxide. The aqueous layer was separated, washed with ethyl acetate (20 ml×2) and thereto was added ethyl acetate. The resulting mixture was adjusted to pH 2.5 with 10% hydrochloric acid. The ethyl acetate layer was separated, washed with a saturated aqueous solution of sodium chloride, dried over magnesium sulfate and then evaporated to give an oil of 2-(2-propynyl)-2H-tetrazole-5-thiol (0.3 g).

I.R. (Nujol): 3270, 2140 $cm^{-1}$

N.M.R. (DMSO-$d_6$, $\delta$): 3.71 (1H, t, J=2.5 Hz), 5.78 (2H, d, J=2.5 Hz)

Preparation 7

The following compounds were prepared according to the similar manner to that of Preparation 2.

(1) 1-(2-Propynyl)-1H-tetrazole-5-thiol

I.R. (Nujol): 3240, 2125 $cm^{-1}$ (2) 2-(2-Propynyl)-2H-tetrazole-5-thiol

I.R. (Nujol): 3270, 2140 $cm^{-1}$

Preparation 8

A mixture of benzyhydryl 7-(2-phenylacetamido)-3-chloromethyl-3-cephem-4-carboxylate-1-oxide (70.0 g), 1H-tetrazole-5-thiol (15.6 g) and N,N-dimethylformamide (700 ml) was stirred to give a homogeneous solution and thereto was added triethylamine (32.1 g), keeping the temperature at 20° to 30° C. The resulting solution was stirred for 40 minutes at room temperature. After the reaction mixture was added to ice water (2.8 l), the mixture was adjusted to pH 2.0 with 10% hydrochloric acid and then filtered. The filter cake was washed with water and dried over phosphorus pentoxide under reduced pressure to give benzhydryl 7-(2-phenylacetamido)-3-(1H-tetrazole-5-yl)thiomethyl-3-cephem-4-carboxylate-1-oxide (78.8 g).

I.R. (Nujol): 3300, 1790, 1700, 1645 $cm^{-1}$

N.M.R. (DMSO-$d_6$, $\delta$): 3.66 (2H, m), 3.97 (2H, s), 4.35 (2H, q, J=14.0 Hz), 4.97 (1H, d, J=4.0 Hz), 5.92 (1H, dd, J=4.0 and 8.0 Hz), 6.93 (1H, s), 7.05–7.83 (15H, m), 8.33 (1H, d, J=8.0 Hz)

Preparation 9

(1) A mixture of benzhydrylbromide (298.3 g) and thiosemicarbazide (100 g) in dry ethanol (1 l) was refluxed for 3 hours, and the ethanol was evaporated off under reduced pressure to give a crude oily product of 3-benzhydrylisothiosemicarbazide hydrobromide.

Thus obtained crude product was used in the next step reaction without isolation.

(2) To a mixture of the crude product of 3-benzhydrylisothiosemicarbazide hydrobromide from (1) above, water (2.3 l), conc. hydrochloric acid (126 g) and toluene (900 ml) was dropwise added a solution of sodium nitrite (83.5 g) in water (200 ml) and the resulting mixture was stirred for 1.5 hours at 10° to 15° C. The reaction mixture was extracted with ethyl acetate. The organic layer was added to water (1 l) and adjusted to pH 9.5 with 4 N aqueous solution of sodium hydroxide. The separated aqueous layer was then adjusted to pH 2.5 with 10% hydrochloric acid and extracted with ethyl acetate. The ethyl acetate layer was washed with water, dried and evaporated to give a residue, which was washed with a mixture of n-hexane and isopropyl ether (2:1) and air-dried to give 5-benzhydrylthio-1H-tetrazole (127.22 g), mp 132° to 134° C.

NMR (DMSO-$d_6$, $\delta$): 6.32 (1H, s), 7.21–7.73 (10H, m)

EXAMPLE 1

To a suspension of 7-aminocephalosporanic acid (0.35 g) and 1-(2-propynyl)-1H-tetrazole-5-thiol (0.20 g) in acetonitril (1.8 ml) was added boron trifluoride etherate (0.55 g) at room temperature and the resulting mixture was stirred for 1.5 hours at 47° C. To the reaction mixture was added water (1.8 ml) and the mixture was adjusted to pH 3.5 with conc. aqueous ammonia under ice-cooling. The precipitates were collected by filtration, washed successively with water and acetone and then dried to give 7-amino-3-[1-(2-propynyl)-1H-tetrazole-5-yl]thiomethyl-3-cephem-4-carboxylic acid (0.36 g).

I.R. (Nujol): 3250, 3160, 2130 cm$^{-1}$

N.M.R. (DMSO-d$_6$, δ): 3.67 (3H, m), 4.38 (2H, q, J=14.0 Hz), 4.81 (1H, d, J=5.0 Hz), 4.98 (1H, d, J=5.0 Hz), 5.31 (2H, d, J=2.0 Hz)

EXAMPLE 2

To a suspension of 7-aminocephalosporanic acid (0.70 g) and 2-(2-propynyl)-2H-tetrazole-5-thiol (0.40 g) in acetonitril (3.5 ml) was added boron trifluoride etherate (1.1 g) at room temperature and the resulting mixture was stirred for an hour at 48° to 50° C. To the reaction mixture was added water (4 ml) and the mixture was adjusted to pH 3.3 with 25% aqueous ammonia at 10° C. The precipitates were collected by filtration, washed successively with water and acetone and then dried to give 7-amino-3-[2-(2-propynyl)-2H-tetrazol-5-yl]-thiomethyl-3-cephem-4-carboxylic acid (0.345 g).

I.R. (Nujol): 3260, 3150, 1800 cm$^{-1}$

N.M.R. (DMSO-d$_6$, δ): 3.40–3.80 (3H, m), 4.28 (2H, ABq, J=13 Hz), 4.71 (1H, d, J=5 Hz), 4.88 (1H, d, J=5 Hz), 5.63 (2H, d, J=2.5 Hz)

EXAMPLE 3

The following compounds were prepared according to the similar manners to those of Examples 1 and 2.

(1) Benzhydryl 7-amino-3-[1-(2-propynyl)-1H-tetrazol-5-yl]thiomethyl-3-cephem-4-carboxylate.

I.R. (Nujol): 3270, 2140, 1770, 1720, 1620 cm$^{-1}$ (2) Benzhydryl 7-amino-3-[2-(2-propynyl)-2H-tetrazol-5-yl]thiomethyl-3-cephem-4-carboxylate I.R. (Film): 3400, 3270, 2950, 2850, 2140, 1770, 1710, 1615 cm$^{-1}$ (3) Benzhydryl 7-(2-phenylacetamido)-3-[1-(2-propynyl)-1H-tetrazol-5-yl]thiomethyl-3-cephem-4-carboxylate-1-oxide.

I.R. (Nujol): 3250, 2130, 1780, 1720, 1665 cm$^{-1}$ (4) Benzhydryl 7-(2-phenylacetamido)-3-[2-(2-propynyl)-2H-tetrazol-5-yl]thiomethyl-3-cephem-4-carboxylate-1-oxide.

I.R. (Nujol): 3320, 2140, 1775, 1710, 1640 cm$^{-1}$ (5) Benzhydryl 7-(2-phenylacetamido)-3-[1-(2-propynyl)-1H-tetrazol-5-yl]thiomethyl-3-cephem-4-carboxylate.

I.R. (Nujol): 3260, 2130, 1770, 1710, 1660 cm$^{-1}$ (6) Benzhydryl 7-(2-phenylacetamido)-3-[2-(2-propynyl)-2H-tetrazol-5-yl]thiomethyl-3-cephem-4-carboxylate.

I.R. (Nujol): 3280, 2140, 1770, 1710, 1660 cm$^{-1}$ (7) Benzhydryl 7-[2-methoxyimino-2-(2-formamidothiazol-4-yl)acetamido]-3-[1-(2-propynyl)-1H-tetrazol-5-yl]-thiomethyl-3-cephem-4-carboxylate (syn isomer).

I.R. (Nujol): 3150, 2140, 1780, 1680, 1645 cm$^{-1}$ (8) 7-[2-Methoxyimino-2-(2-formamidothiazol-4-yl)-acetamido]-3-[1-(2-propynyl)-1H-tetrazol-5-yl]-thiomethyl-3-cephem-4-carboxylic acid (syn isomer).

I.R. (Nujol): 3250, 2150, 1780, 1680 cm$^{-1}$ (9) Benzhydryl 7-[2-methoxyimino-2-(2-formamidothiazol-4-yl)acetamido]-3-[2-(2-propynyl)-2H-tetrazol-5-yl]-thiomethyl-3-cephem-4-carboxylate (syn isomer).

I.R. (Nujol): 3250, 2140, 1780, 1720, 1670 cm$^{-1}$

(10) 7-[2-Methoxyimino-2-(2-aminothiazol-4-yl)acetamido]-3-[1-(2-propynyl)-1H-tetrazol-5-yl]thiomethyl-3-cephem-4-carboxylic acid (syn isomer).

I.R. (Nujol): 3280, 2100, 1770, 1660, 1630 cm$^{-1}$

(11) Benzhydryl 7-[2-methoxyimino-2-(2-aminothiazol-4-yl)yl)acetamido]-3-[2-(2-propynyl)-2H-tetrazol-5-yl]-thiomethyl-3-cephem-4-carboxylate (syn isomer).

I.R. (Nujol): 3270, 2150, 1775, 1725, 1670, 1680 cm$^{-1}$

(12) 7-[2-Methoxyimino-2-(2-aminothiazol-4-yl)acetamido]-3-[2-(2-propynyl)-2H-tetrazol-5-yl]thiomethyl-3-cephem-4-carboxylic acid (syn isomer).

I.R. (Nujol): 3300, 2100, 1770, 1660, 1630 cm$^{-1}$

(13) 7-[2-Cyclopentyloxyimino-2-[2-(2,2,2-trifluoroacetamido)thiazol-4-yl]acetamido]-3-[1-(2-propynyl)-1H-tetrazol-5-yl]thiomethyl-3-cephem-4-carboxylic acid (syn isomer).

I.R. (Nujol): 3260, 2130, 1785, 1720, 1680 cm$^{-1}$

(14) 7-[2-Cyclopentyloxyimino-2-(2-aminothiazol-4-yl)-acetamido]-3-[1-(2-propynyl)-1H-tetrazol-5-yl]-thiomethyl-3-cephem-4-carboxylic acid (syn isomer).

I.R. (Nujol): 3260, 2110, 1780, 1665 cm$^{-1}$

(15) Benzhydryl 7-[2-methoxyimino-2-(5-amino-1,2,4-thiadiazol-3-yl)acetamido]-3-[1-(2-propynyl)-1H-tetrazol-5-yl]thiomethyl-3-cephem-4-carboxylate (syn isomer).

I.R. (Nujol): 3250, 2130, 1770, 1720, 1660, 1620 cm$^{-1}$

(16) 7-[2-Methoxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer).

I.R. (Nujol): 3300, 1770, 1670, 1620 cm$^{-1}$

(17) 7-[2-Methoxyimino-2-(thiazol-4-yl)acetamido]-3-[1-(2-propynyl)-1H-tetrazol-5-yl]thiomethyl-3-cephem-4-carboxylic acid (syn isomer).

I.R. (Nujol): 3310, 2150, 1785, 1725, 1680 cm$^{-1}$

(18) 7-[2-(1H-tetrazol-1-yl)acetamido]-3-[1-(2-propynyl)-1H-tetrazol-5-yl]thiomethyl-3-cephem-4-carboxylic acid.

I.R. (Nujol): 3260, 2110, 1770, 1695 cm$^{-1}$

(19) Benzhydryl 7-[2-allyloxyimino-2-(2-formamidothiazol-4-yl)acetamido]-3-[1-(2-propynyl)-1H-tetrazol-5-yl]-thiomethyl-3-cephem-4-carboxylate (syn isomer).

I.R. (Nujol): 3250, 2150, 1780, 1680 cm$^{-1}$

(20) 7-[2-Allyloxyimino-2-(2-formamidothiazol-4-yl)-acetamido]-3-[1-(2-propynyl)-1H-tetrazol-5-yl]-thiomethyl-3-cephem-4-carboxylic acid (syn isomer).

I.R. (Nujol): 3250, 2140, 1770, 1670 cm$^{-1}$

(21) 7-[2-Allyloxyimino-2-(2-aminothiazol-4-yl)-acetamido]-3-[1-(2-propynyl)-1H-tetrazol-5-yl]-thiomethyl-3-cephem-4-carboxylic acid (syn isomer).

I.R. (Nujol): 3260, 2110, 1750, 1670, 1630 cm$^{-1}$

(22) 7-[2-(2-Cyclopenten-1-yl)oxyimino-2-(2-formamidothiazol-4-yl)acetamido]-3-[1-(2-propynyl)-1H-tetrazol-5-yl]thiomethyl-3-cephem-4-carboxylic acid (syn isomer).

I.R. (Nujol): 3240, 2125, 1775, 1680 cm$^{-1}$

(23) 7-[2-(2-Cyclopenten-1-yl)oxyimino-2-(2-aminothiazol-4-yl)acetamido]-3-[1-(2-propynyl)-1H-tetrazol-5-yl]thiomethyl-3-cephem-4-carboxylic acid (syn isomer).

I.R. (Nujol): 3270, 2120, 1775, 1670 cm$^{-1}$

(24) 7-[2-Isopropoxyimino-2-(2-formamidothiazol-4-yl)-acetamido]-3-[1-(2-propynyl)-1H-tetrazol-5-yl]-thiomethyl-3-cephem-4-carboxylic acid (syn isomer).

N.M.R. (DMSO-d$_6$, δ): 1.20 (6H, d, J=6 Hz), 3.53–3.75 (3H, m), 4.35 (2H, m), 5.13 (1 H, d, J=5 Hz), 5.90 (2H, d, J=2 Hz), 5.78 (1H, dd, J=5 and 8 Hz), 7.34 (1H, s), 8.48 (1H, s), 9.57 (1H, d, J=8 Hz)

(25) 7-[2-Isopropoxyimino-2-(2-aminothiazol-4-yl)-acetamido]-3-[1-(2-propynyl)-1H-tetrazol-5-yl]-thiomethyl-3-cephem-4-carboxylic acid (syn isomer).

I.R. (Nujol): 3320, 2150, 1775, 1670 cm$^{-1}$

(26) 7-[2-(2-Propynyl)oxyimino-2-(2-formamidothiazol-4-yl)acetamido]-3-[1-(2-propynyl)-1H-tetrazol-5-yl]-thiomethyl-3-cephem-4-carboxylic acid (syn isomer).

I.R. (Nujol): 3240, 2120, 1770, 1665 cm$^{-1}$

(27) 7-[2-(2-Propynyl)oxyimino-2-(2-aminothiazol-4-yl)-acetamido]-3-[1-(2-propynyl)-1H-tetrazol-5-yl]-thiomethyl-3-cephem-4-carboxylic acid (syn isomer).

I.R. (Nujol): 3280, 2110, 1770, 1670 cm$^{-1}$

(28) 7-[2-(2-Formamidothiazol-4-yl)glyoxylamido]-3-[1-(2-propynyl)-1H-tetrazol-5-yl]thiomethyl-3-cephem-4-carboxylic acid.

I.R. (Nujol): 3260, 3120, 2130, 1765, 1715, 1670 cm$^{-1}$

(29) 7-[2-(2-Aminothiazol-4-yl)glyoxylamido]-3-[1-(2-propynyl)-1H-tetrazol-5-yl]thiomethyl-3-cephem-4-carboxylic acid.

I.R. (Nujol): 3250, 2125, 1765, 1665, 1630 cm$^{-1}$

(30) 7-[2-(2-Aminothiazol-4-yl)-D,L-glycolamido]-3-[1-(2-propynyl)-1H-tetrazol-5-yl]thiomethyl-3-cephem-4-carboxylic acid.

I.R. (Nujol): 3260, 2140, 1770, 1680, 1630 cm$^{-1}$

(31) 7-[2-Benzyloxyimino-2-[2-(2,2,2-trifluoroacetamido)-thiazol-4-yl]acetamido]-3-[1-(2-propynyl)-1H-tetrazol-5-yl]thiomethyl-3-cephem-4-carboxylic acid (syn isomer).

I.R. (Nujol): 3280, 3230, 2140, 1785, 1725, 1655 cm$^{-1}$

(32) 7-[2-Benzyloxyimino-2-(2-aminothiazol-4-yl)-acetamido]-3-[1-(2-propynyl)-1H-tetrazol-5-yl]-thiomethyl-3-cephem-4-carboxylic acid (syn isomer).

I.R. (Nujol): 3270, 2110, 1770, 1665 cm$^{-1}$

(33) 7-[D-2-Formyloxy-2-phenylacetamido]-3-[1-(2-propynyl)-1H-tetrazol-5-yl]thiomethyl-3-cephem-4-carboxylic acid.

I.R. (Nujol): 3260, 2130, 1775, 1715 cm$^{-1}$

(34) 7-(2-Phenyl-D-glycolamido)-3-[1-(2-propynyl)-1H-tetrazol-5-yl]thiomethyl-3-cephem-4-carboxylic acid.

I.R. (Nujol): 3300, 3260, 2130, 1775, 1680 cm$^{-1}$

(35) 7-[2-tert-Butoxycarbonylmethoxyimino-2-(2-formamidothiazol-4-yl)acetamido]-3-[1-(2-propynyl)-1H-tetrazol-5-yl]thiomethyl-3-cephem-4-carboxylic acid (syn isomer).

I.R. (Nujol): 3240, 2130, 1780, 1720, 1675 cm$^{-1}$

(36) 7-[2-tert-Butoxycarbonylmethoxyimino-2-(2-aminothiazol-4-yl)acetamido]-3-[1-(2-propynyl)-1H-tetrazol-5-yl]thiomethyl-3-cephem-4-carboxylic acid hydrochloride (syn isomer).

I.R. (Nujol): 3350, 3230, 2125, 1770, 1715, 1675, 1625 cm$^{-1}$

(37) 7-[2-Carboxymethoxyimino-2-(2-aminothiazol-4-yl)acetamido]-3-[1-(2-propynyl)-1H-tetrazol-5-yl]thiomethyl-3-cephem-4-carboxylic acid hydrochloride (syn isomer).

I.R. (Nujol): 3260, 2120, 1765, 1660, 1625 cm$^{-1}$

(38) 7-[2-Ethoxyimino-2-(2-aminothiazol-4-yl)acetamido]-3-[1-(2-propynyl)-1H-tetrazol-5-yl]thiomethyl-3-cephem-4-carboxylic acid (syn isomer).

IR (Nujol): 3250, 2100, 1770, 1670, 1625 cm$^{-1}$

(39) 7-[2-Ethoxyimino-2-(2-formamidothiazol-4-yl)-acetamido]-3-[1-(2-propynyl)-1H-tetrazol-5-yl]-thiomethyl-3-cephem-4-carboxylic acid (syn isomer).

IR (Nujol): 3250, 3150, 2140, 1770, 1680, 1650 cm$^{-1}$

(40) 7-[2-Cyclopentyloxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer), mp. 145° to 150° C. (dec.).

IR (Nujol): 3300, 3200, 2120, 1775, 1680, 1620, 1520 cm$^{-1}$

(41) 7-[2-(2-Cyclopenten-1-yl)oxyimino-2-(5-amino-1,2,4-thiadiazol-3-yl)acetamido-3-[1-(2-propynyl)-1H-tetrazol-5-yl]thiomethyl-3-cephem-4-carboxylic acid (syn isomer), mp. 145° to 150° C. (dec.).

IR (Nujol): 3300, 3200, 2120, 1770, 1675, 1620, 1520 cm$^{-1}$

(42) 7-[2-tert-Butoxycarbonylmethoxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer), mp. 120° to 125° C. (dec.).

IR (Nujol): 3300, 1770, 1720, 1680, 1620, 1520 cm$^{-1}$

(43) 7-[2-Carboxymethoxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer), mp. 160° to 165° C. (dec.).

IR (Nujol): 3300, 3250, 1770, 1720, 1680, 1620, 1520 cm$^{-1}$

(44) 7-(D-2-tert-Butoxycarbonylamino-2-phenylacetamido)-3-[1-(2-propynyl)-1H-tetrazol-5-yl]-thiomethyl-3-cephem-4-carboxylic acid.

IR (Nujol): 3260, 2130, 1775, 1700, 1685 1660 cm$^{-1}$

(45) 7-(D-2-Phenylglycylamino)-3-[1-(2-propynyl)-1H-tetrazol-5-yl]thiomethyl-3-cephem-4-carboxylic acid trifluoroacetate.

IR (Nujol): 3250, 2130, 1775, 1660 cm$^{-1}$

(46) 7-(2-Allylthioacetamido)-3-[1-(2-propynyl)-1H-tetrazol-5-yl]thiomethyl-3-cephem-4-carboxylic acid.

IR (KBr): 3250, 2940, 2110, 1770, 1710 cm$^{-1}$

EXAMPLE 4

A mixture of benzhydryl 7-(2-phenylacetamido)-3-(1H-tetrazol-5-yl)thiomethyl-3-cephem-4-carboxylate-1-oxide (78.0 g) in N,N-dimethylformamide (780 ml) was stirred to give a homogeneous solution and thereto were added 2-propynyl bromide (30.2 g) and triethylamine (38.5 g). The resulting solution was stirred for 22.3 hours at room temperature. The reaction mixture was added to ice-water (1.5 l) and the mixture was extracted with ethyl acetate (x 2). The extract was washed with water (x 4), dried over magnesium sulfate, treated with activated charcoal and then evaporated. The residue was pulverized in isopropyl ether, collected by filtration, washed with isopropyl ether and then dried. The obtained product (60.61 g) was subjected to column chromatography on silica gel (1.5 kg), using benzene and ethyl acetate (2:1) as an eluent. Fractions containing 2-(2-propynyl)-2H-tetrazolyl isomer, which were firstly eluted, were collected and then evaporated. The residue was pulverized in a mixture of isopropyl ether and n-hexane to give benzhydryl 7-(2-phenylacetamido)-3-[2-(2-propynyl)-2H-tetrazol-5-yl]thiomethyl-3-cephem-4-carboxylate-1-oxide (16.34 g).

I.R. (Nujol): 3320, 2140, 1775, 1710, 1640 cm$^{-1}$

N.M.R. (DMSO-d$_6$, δ): 3.30 (1H, s), 3.65 (2H, m), 3.90 (2H, m), 4.29 (2H, q, J=14.0 Hz), 4.90 (1H, d, J=4.0 Hz), 5.61 (2H, d, J=2.0 Hz), 5.91 (1H, dd, J=4.0 and 8.0 Hz), 6.97 (1H, s), 7.10–7.74 (15H, m), 8.34 (1H, d, J=8.0 Hz)

Further, subsequent fractions containing 1-(2-propynyl)-1H-tetrazolyl isomer were collected and evaporated and then the residue was pulverized in a mixture of isopropyl ether and n-hexane to give benzhydryl 7-(2-phenylacetamido)-3-[1-(2-propynyl)-1H-tetrazol-5-yl]thiomethyl-3-cephem-4-carboxylate-1-oxide (9.3 g).

I.R. (Nujol): 3250, 2130, 1780, 1720, 1665 cm$^{-1}$

N.M.R. (DMSO-d$_6$, δ): 3.34 (1H, s), 3.64 (2H, m), 3.95 (2H, m), 4.40 (2H, q, J=13.0 Hz), 4.92 (1H, d, J=4.0 Hz), 5.28 (2H, d, J=2.0 Hz), 5.93 (1H, dd, J=4.0 and 8.0 Hz), 6.96 (1H, s), 7.08–7.80 (15H, m), 8.35 (1H, d, J=8.0 Hz)

EXAMPLE 5

The following compounds were prepared according to the similar manner to that of Example 4.

(1) Benzhydryl 7-amino-3-[1-(2-propynyl)-1H-tetrazol-5-yl]thiomethyl-3-cephem-4-carboxylate.
I.R. (Nujol): 3270, 2140, 1770, 1720, 1620 cm$^{-1}$
(2) 7-Amino-3-[1-(2-propynyl)-1H-tetrazol-5-yl]-thiomethyl-3-cephem-4-carboxylic acid.
I.R. (Nujol): 3250, 3160, 2130 cm$^{-1}$
(3) Benzhydryl 7-amino-3-[2-(2-propynyl)-2H-tetrazol-5-yl]thiomethyl-3-cephem-4-carboxylate.
I.R. (Film): 3400, 3270, 2950, 2850, 2140, 1770, 1710, 1615 cm$^{-1}$
(4) 7-Amino-3-[2-(2-propynyl)-2H-tetrazol-5-yl]-thiomethyl-3-cephem-4-carboxylic acid.
I.R. (Nujol): 3260, 3150, 1800 cm$^{-1}$
(5) Benzhydryl-7-(2-phenylacetamido)-3-[1-(2-propynyl)-1H-tetrazol-5-yl]thiomethyl-3-cephem-4-carboxylate.
I.R. (Nujol): 3260, 2130, 1770, 1710, 1660 cm$^{-1}$
(6) Benzhydryl 7-(2-phenylacetamido)-3-[2-(2-propynyl)-2H-tetrazol-5-yl]thiomethyl-3-cephem-4-carboxylate.
I.R. (Nujol): 3280, 2140, 1770, 1710, 1660 cm$^{-1}$
(7) Benzhydryl 7-[2-methoxyimino-2-(2-formamidothiazol-4-yl)acetamido]-3-[1-(2-propynyl)-1H-tetrazol-5-yl]-thiomethyl-3-cephem-4-carboxylate (syn isomer).
I.R. (Nujol): 3150, 2140, 1780, 1680, 1645 cm$^{-1}$
(8) 7-[2-Methoxyimino-2-(2-formamidothiazol-4-yl)acetamido]-3-[1-(2-propynyl)-1H-tetrazol-5-yl]-thiomethyl-3-cephem-4-carboxylic acid (syn isomer).
I.R. (Nujol): 3250, 2150, 1780, 1680 cm$^{-1}$
(9) Benzhydryl 7-[2-methoxyimino-2-(2-formamidothiazol-4-yl)acetamido]-3-[2-(2-propynyl)-2H-tetrazol-5-yl]-thiomethyl-3-cephem-4-carboxylate (syn isomer).
I.R. (Nujol): 3250, 2140, 1780, 1720, 1670 cm$^{-1}$
(10) 7-[2-Methoxyimino-2-(2-aminothiazol-4-yl)acetamido]-3-[1-(2-propynyl)-1H-tetrazol-5-yl]thiomethyl-3-cephem-4-carboxylic acid (syn isomer).
I.R. (Nujol): 3280, 2100, 1770, 1660, 1630 cm$^{-1}$
(11) Benzhydryl 7-[2-methoxyimino-2-(2-aminothiazol-4-yl)acetamido]-3-[2-(2-propynyl)-2H-tetrazol-5-yl]-thiomethyl-3-cephem-4-carboxylate (syn isomer).
I.R. (Nujol): 3270, 2150, 1775, 1725, 1670, 1680 cm$^{-1}$
(12) 7-[2-Methoxyimino-2-(2-aminothiazol-4-yl)acetamido]-3-[2-(2-propynyl)-2H-tetrazol-5-yl]thiomethyl-3-cephem-4-carboxylic acid (syn isomer).
I.R. (Nujol): 3300, 2100, 1770, 1660, 1630 cm$^{-1}$
(13) 7-[2-Cyclopentyloxyimino-2-[2-(2,2,2-trifluoroacetamido)thiazol-4-yl]acetamido]-3-[1-(2-propynyl)-1H-tetrazol-5-yl]thiomethyl-3-cephem-4-carboxylic acid (syn isomer).
I.R. (Nujol): 3260, 2130, 1785, 1720, 1680 cm$^{-1}$
(14) 7-[2-Cyclopentyloxyimino-2-(2-aminothiazol-4-yl)-acetamido]-3-[1-(2-propynyl)-1H-tetrazol-5-yl]-thiomethyl-3-cephem-4-carboxylic acid (syn isomer).
I.R. (Nujol): 3260, 2110, 1780, 1665 cm$^{-1}$
(15) Benzhydryl 7-[2-methoxyimino-2-(5-amino-1,2,4-thiadiazol-3-yl)acetamido]-3-[1-(2-propynyl)-1H-tetrazol-5-yl]thiomethyl-3-cephem-4-carboxylate (syn isomer).
I.R. (Nujol): 3250, 2130, 1770, 1720, 1660, 1620 cm$^{-1}$
(16) 7-[2-Methoxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer).
I.R. (Nujol): 3300, 1770, 1670, 1620 cm$^{-1}$
(17) 7-[2-Methoxyimino-2-(thiazol-4-yl)acetamido]-3-[1-(2-propynyl)-1H-tetrazol-5-yl]thiomethyl-3-cephem-4-carboxylic acid (syn isomer).
I.R. (Nujol): 3310, 2150, 1785, 1725, 1680 cm$^{-1}$
(18) 7-[2-(1H-tetrazol-1-yl)acetamido]-3-[1-(2-propynyl)-1H-tetrazol-5-yl]thiomethyl-3-cephem-4-carboxylic acid.
I.R. (Nujol): 3260, 2110, 1770, 1695 cm$^{-1}$
(19) Benzhydryl 7-[2-allyloxyimino-2-(2-formamidothiazol-4-yl)acetamido]-3-[1-(2-propynyl)-1H-tetrazol-5-yl]-thiomethyl-3-cephem-4-carboxylate (syn isomer).
I.R. (Nujol): 3250, 2150, 1780, 1680 cm$^{-1}$
(20) 7-[2-Allyloxyimino-2-(2-formamidothiazol-4-yl)-acetamido]-3-[1-(2-propynyl)-1H-tetrazol-5-yl]-thiomethyl-3-cephem-4-carboxylic acid (syn isomer).
I.R. (Nujol): 3250, 2140, 1770, 1670 cm$^{-1}$
(21) 7-[2-Allyloxyimino-2-(2-aminothiazol-4-yl)-acetamido]-3-[1-(2-propynyl)-1H-tetrazol-5-yl]thiomethyl-3-cephem-4-carboxylic acid (syn isomer).
I.R. (Nujol): 3260, 2110, 1750, 1670, 1630 cm$^{-1}$
(22) 7-[2-(2-Cyclopenten-1-yl)oxyimino-2-(2-formamidothiazol-4-yl)acetamido]-3-[1-(2-propynyl)-1H-tetrazol-5-yl]thiomethyl-3-cephem-4-carboxylic acid (syn isomer).
I.R. (Nujol): 3240, 2125, 1775, 1680 cm$^{-1}$
(23) 7-[2-(2-Cyclopenten-1-yl)oxyimino-2-(2-aminothiazol-4-yl)acetamido]-3-[1-(2-propynyl)-1H-tetrazol-5-yl]thiomethyl-3-cephem-4-carboxylic acid (syn isomer).
I.R. (Nujol): 3270, 2120, 1775, 1670 cm$^{-1}$
(24) 7-[2-Isopropoxyimino-2-(2-formamidothiazol-4-yl)-acetamido]-3-[1-(2-propynyl)-1H-tetrazol-5-yl]-thiomethyl-3-cephem-4-carboxylic acid (syn isomer).
N.M.R. (DMSO-d$_6$, δ): 1.20 (6H, d, J=6 Hz), 3.53-3.75 (3H, m), 4.35 (2H, m), 5.13 (1H, d, J=5 Hz), 5.90 (2H, d, J=2 Hz), 5.78 (1H, dd, J=5 and 8 Hz), 7.34 (1H, s), 8.48 (1H, s), 9.57 (1H, d, J=8 Hz)
(25) 7-[2-Isopropoxyimino-2-(2-aminothiazol-4-yl)-acetamido]-3-[1-(2-propynyl)-1H-tetrazol-5-yl]-thiomethyl-3-cephem-4-carboxylic acid (syn isomer).
I.R. (Nujol): 3320, 2150, 1775, 1670 cm$^{-1}$
(26) 7-[2-(2-Propynyl)oxyimino-2-(2-formamidothiazol-4-yl)acetamido]-3-[1-(2-propynyl)-1H-tetrazol-5-yl]-thiomethyl-3-cephem-4-carboxylic acid (syn isomer).
I.R. (Nujol): 3240, 2120, 1770, 1665 cm$^{-1}$
(27) 7-[2-(2-Propynyl)oxyimino-2-(2-aminothiazol-4-yl)acetamido]-3-[1-(2-propynyl)-1H-tetrazol-5-yl]-thiomethyl-3-cephem-4-carboxylic acid (syn isomer).
I.R. (Nujol): 3280, 2110, 1770, 1670 cm$^{-1}$
(28) 7-[2-(2-Formamidothiazol-4-yl)glyoxylamido]-3-[1-(2-propynyl)-1H-tetrazol-5-yl]thiomethyl-3-cephem-4-carboxylic acid.
I.R. (Nujol): 3260, 3120, 2130, 1765, 1715, 1670 cm$^{-1}$
(29) 7-[2-(2-Amoinothiazol-4-yl)glyoxylamido]-3-[1-(2-propynyl)-1H-tetrazol-5-yl]thiomethyl-3-cephem-4-carboxylic acid.
I.R. (Nujol): 3250, 2125, 1765, 1665, 1630 cm$^{-1}$
(30) 7-[2-(2-Aminothiazol-4-yl)-D,L-glycolamido]-3-[1-(2-propynyl)-1H-tetrazol-5-yl]thiomethyl-3-cephem-4-carboxylic acid.
I.R. (Nujol): 3260, 2140, 1770, 1680, 1630 cm$^{-1}$
(31) 7-[2-Benzyloxyimino-2-[2-(2,2,2-trifluoroacetamido)-thiazol-4-yl]acetamido]-3-[1-(2-propynyl)-1H-tetrazol-5-yl]thiomethyl-3-cephem-4-carboxylic acid (syn isomer).
I.R. (Nujol): 3280, 3230, 2140, 1785, 1725, 1655 cm$^{1}$
(32) 7-[2-Benzyloxyimino-2-(2-aminothiazol-4-yl)-acetamido]-3-[1-(2-propynyl)-1H-tetrazol-5-yl]-thiomethyl-3-cephem-4-carboxylic acid (syn isomer).
I.R. (Nujol): 3270, 2110, 1770, 1665 cm$^{-1}$
(33) 7-[D-2-Formyloxy-2-phenylacetamido]-3-[1-(2-propynyl)-1H-tetrazol-5-yl]thiomethyl-3-cephem-4-carboxylic acid.
I.R. (Nujol): 3260, 2130, 1775, 1715 cm$^{-1}$
(34) 7-(2-Phenyl-D-glycolamido)-3-[1-(2-propynyl)-1H-tetrazol-5-yl]thiomethyl-3-cephem-4-carboxylic acid.

I.R. (Nujol): 3300, 3260, 2130, 1775, 1680 cm$^{-1}$

(35) 7-[2-tert-Butoxycaarbonylmethoxyimino-2-(2-formamidothiazol-4-yl)acetamido]-3-[1-(2-propynyl)-1H-tetrazol-5-yl]thiomethyl-3-cephem-4-carboxylic acid (syn isomer).

I.R. (Nujol): 3240, 2130, 1780, 1720, 1675 cm$^{-1}$

(36) 7-[2-tert-Butoxycarbonylmethoxyimino-2-(2-aminothiazol-4-yl)acetamido]-3-[1-(2-propynyl)-1H-tetrazol-5-yl]thiomethyl-3-cephem-4-carboxylic acid hydrochloride (syn isomer).

I.R. (Nujol): 3350, 3230, 2125, 1770, 1715, 1675, 1625 cm$^{-1}$

(37) 7-[2-Carboxymethoxyimino-2-(2-aminothiazol-4-yl)acetamido]-3-[1-(2-propynyl)-1H-tetrazol-5-yl]thiomethyl-3-cephem-4-carboxylic acid hydrochloride (syn isomer).

I.R. (Nujol): 3260, 2120, 1765, 1660, 1625 cm$^{-1}$

(38) 7-[2-Ethoxyimino-2-(2-aminothiazol-4-yl)acetamido]-3-[1-(2-propynyl)-1H-tetrazol-5-yl]thiomethyl-3-cephem-4-carboxylic acid (syn isomer).

IR (Nujol): 3250, 2100, 1770, 1670, 1625 cm$^{-1}$

(39) 7-[2-Ethoxyimino-2-(2-formamidothiazol-4-yl)-acetamido]-3-[1-(2-propynyl)-1H-tetrazol-5-yl]-thiomethyl-3-cephem-4-carboxylic acid (syn isomer).

IR (Nujol): 3250, 3150, 2140, 1770, 1680, 1650 cm$^{-1}$

(40) 7-[2-Cyclopentyloxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer), mp. 145° to 150° C. (dec.).

IR (Nujol): 3300, 3200, 2120, 1775, 1680, 1620, 1520 cm$^{-1}$

(41) 7-[2-(2-Cyclopenten-1-yl)oxyimino-2-(5-amino-1,2,4-thiadiazol-3-yl)acetamido-3-[1-(2-propynyl)-1H-tetrazol-5-yl]thiomethyl-3-cephem-4-carboxylic acid (syn isomer), mp. 145° to 150° C. (dec.).

IR (Nujol): 3300, 3200, 2120, 1775, 1675, 1620, 1520 cm$^{-1}$

(42) 7-[2-tert-Butoxycarbonylmethoxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer), mp. 120° to 125° C. (dec.).

IR (Nujol): 3300, 1770, 1720, 1680, 1620, 1520 cm$^{-1}$

(43) 7-[2-Carboxymethoxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer), mp. 160° to 165° C. (dec.).

IR (Nujol): 3300, 3250, 1770, 1720, 1680, 1620, 1520 cm$^{-1}$

(44) 7-(D-2-tert-Butoxycarbonylamino-2-phenylacetamido)-3-[1-(2-propynyl)-1H-tetrazol-5-yl]thiomethyl-3-cephem-4-carboxylic acid.

IR (Nujol): 3260, 2130, 1775, 1700, 1685 1660 cm$^{-1}$

(45) 7-(D-2-Phenylglycylamino)-3-[1-(2-propynyl)-1H-tetrazol-5-yl]thiomethyl-3-cephem-4-carboxylic acid trifluoroacetate.

IR (Nujol): 3250, 2130, 1775, 1660 cm$^{-1}$

(46) 7-(2-Allylthioacetamido)-3-[1-(2-propynyl)-1H-tetrazol-5-yl]thiomethyl-3-cephem-4-carboxylic acid.

IR (KBr): 3250, 2940, 2110, 1770, 1710 cm$^{-1}$

EXAMPLE 6

A mixture of benzhydryl 7-(2-phenylacetamido)-3-[1-(2-propynyl)-1H-tetrazol-5-yl]thiomethyl-3-cephem-4-carboxylate-1-oxide (9.3 g) and dry N,N-dimethylformamide (93 ml) was cooled to −30° C. and thereto was added phosphorus trichloride (3.9 g). The resulting solution was stirred for 40 minutes at −30° C. The reaction mixture was allowed to warm to ambient temperature, added to water (150 ml) and then extracted with ethyl acetate (x3). The extracts were combined, washed successively with a saturated aqueous solution of sodium bicarbonate (x2) and water (x3), dried over magnesium sulfate, treated with activated charcoal and then evaporated. The residue was pulverized in a mixture of isopropyl ether and n-hexane, collected by filtration, washed with n-hexane and then dried to give benzhydryl 7-(2-phenylacetamido)-3-[1-(2-propynyl)-1H-tetrazol-5-yl]-thiomethyl-3-cephem-4-carboxylate (8.07 g).

I.R. (Nujol): 3260, 2130, 1770, 1710, 1660 cm$^{-1}$

EXAMPLE 7

A mixture of benzhydryl 7-(2-phenylacetamido)-3-[2-(2-propynyl)-2H-tetrazol-5-yl]thiomethyl-3-cephem-4-carboxylate-1-oxide (16.0 g) and dry N,N-dimethylformamide (160 ml) was cooled to −30° C. and thereto was added phosphorus trichloride (6.7 g). The resulting solution was stirred for 50 minutes at −30° C. The reaction mixture was allowed to warm to ambient temperature, added to water (200 ml) and then extracted with ethyl acetate (x3). The extracts were combined, washed successively with a saturated aqueous solution of sodium bicarbonate (x3) and water (x3), dried over magnesium sulfate, treated with activated charcoal and then evaporated. The residue was pulverized in a mixture of isopropyl ether and n-hexane, collected by filtration, washed with n-hexane and then dried to give benzhydryl 7-(2-phenylacetamido)-3-[2-(2-propynyl)-2H-tetrazol-5-yl]thiomethyl-3-cephem-4-carboxylate (14.33 g).

I.R. (Nujol): 3280, 2140, 1770, 1710, 1660 cm$^{-1}$

EXAMPLE 8

The following compounds were prepared according to the similar manners to those of Examples 6 and 7.

(1) Benzhydryl 7-amino-3-[1-(2-propynyl)-1H-tetrazol-5-yl]thiomethyl-3-cephem-4-carboxylate.

I.R. (Nujol): 3270, 2140, 1770, 1720, 1620 cm$^{-1}$ (2) 7-Amino-3-[1-(2-propynyl)-1H-tetrazol-5-yl]-thiomethyl-3-cephem-4-carboxylic acid.

I.R. (Nujol): 3250, 3160, 2130 cm$^{-1}$ (3) Benzhydryl 7-amino-3-[2-(2-propynyl)-2H-tetrazol-5-yl]thiomethyl-3-cephem-4-carboxylate.

I.R. (Film): 3400, 3270, 2950, 2850, 2140, 1770, 1710, 1615 cm$^{-1}$ (4) 7-Amino-3-[2-(2-propynyl)-2H-tetrazol-5-yl]thiomethyl-3-cephem-4-carboxylic acid.

I.R. (Nujol): 3260, 3150, 1800 cm$^{-1}$ (5) Benzhydryl 7-[2-methoxyimino-2-(2-formamidothiazol-4-yl)acetamido]-3-[1-(2-propynyl)-1H-tetrazol-5-yl]-thiomethyl-3-cephem-4-carboxylate (syn isomer).

I.R. (Nujol): 3150, 2140, 1780, 1680, 1645 cm$^{-1}$ (6) 7-[2-Methoxyimino-2-(2-formamidothiazol-4-yl)-acetamido]-3-[1-(2-propynyl)-1H-tetrazol-5-yl]-thiomethyl-3-cephem-4-carboxylic acid (syn isomer).

I.R. (Nujol): 3250, 2150, 1780, 1680 cm$^{-1}$ (7) Benzhydryl 7-[2-methoxyimino-2-(2-formamidothiazol-4-yl)acetamido]-3-[2-(2-propynyl)-2H-tetrazol-5-yl]-thiomethyl-3-cephem-4-carboxylate (syn isomer).

I.R. (Nujol): 3250, 2140, 1780, 1720, 1670 cm$^{-1}$ (8) 7-[2-Methoxyimino-2-(2-aminothiazol-4-yl)acetamido]-3-[1-(2-propynyl)-1H-tetrazol-5-yl]-thiomethyl-3-cephem-4-carboxylic acid (syn isomer).

I.R. (Nujol): 3280, 2100, 1770, 1660, 1630 cm$^{-1}$ (9) Benzhydryl 7-[2-methoxyimino-2-(2-aminothiazol-4-yl)acetamido]-3-[2-(2-propynyl)-2H-tetrazol-5-yl]-thiomethyl-3-cephem-4-carboxylate (syn isomer).

I.R. (Nujol): 3270, 2150, 1775, 1725, 1670, 1680 cm$^{-1}$

(10) 7-[2-Methoxyimino-2-(2-aminothiazol-4-yl)acetamido]-3-[2-(2-propynyl)-2H-tetrazol-5-yl]thiomethyl-3-cephem-4-carboxylic acid (syn isomer).

I.R. (Nujol): 3300, 2100, 1770, 1660, 1630 cm$^{-1}$

(11) 7-[2-Cyclopentyloxyimino-2-[2-(2,2,2-trifluoroacetamido)thioazol-4-yl]acetamido]-3-[1-(2-propynyl)-1H-tetrazol-5-yl]thiomethyl-3-cephem-4-carboxylic acid (syn isomer).

I.R. (Nujol): 3260, 2130, 1785, 1720, 1680 cm$^{-1}$

(12) 7-[2-Cyclopentyloxyimino-2-(2-aminothiazol-4-yl)-acetaido]-3-[1-(2-propynyl)-1H-tetrazol-5-yl]-thiomethyl-3-cephem-4-carboxylic acid (syn isomer).

I.R. (Nujol): 3260, 2110, 1780, 1665 cm$^{-1}$

(13) Benzhydryl 7-[2-methoxyimino-2-(5-amino-1,2,4-thiadiazol-3-yl)acetamido]-3-[1-(2-propynyl)-1H-tetrazol-5-yl]thiomethyl-3-cephem-4-carboxylate (syn isomer).

I.R. (Nujol): 3250, 2130, 1770, 1720, 1660, 1620 cm$^{-1}$

(14) 7-[2-Methoxyimino-2-(5-amino-1,2,4-thiadiazol-3-yl)acetamido]-3-[1-(2-propynyl)-1H-tetrazol-5-yl]-thiomethyl-3-cephem-4-carboxylic acid (syn isomer).

I.R. (Nujol): 3300, 1770, 1670, 1620 cm$^{-1}$

(15) 7-[2-Methoxyimino-2-(thiazol-4-yl)acetamido]-3-[1-(2-propynyl)-1H-tetrazol-5-yl]thiomethyl-3-cephem-4-carboxylic acid (syn isomer).

I.R. (Nujol): 3310, 2150, 1785, 1725, 1680 cm$^{-1}$

(16) 7-[2-(1H-tetrazol-1-yl)acetamido]-3-[1-(2-propynyl)-1H-tetrazol-5-yl]thiomethyl-3-cephem-4-carboxylic acid.

I.R. (Nujol): 3260, 2110, 1770, 1695 cm$^{-1}$

(17) Benzhydryl 7-[2-allyloxyimino-2-(2-formamidothiazol-4-yl)acetamido]-3-[1-(2-propynyl)-1H-tetrazol-5-yl]-thiomethyl-3-cephem-4-carboxylate (syn isomer).

I.R. (Nujol): 3250, 2150, 1780, 1680 cm$^{-1}$

(18) 7-[2-Allyloxyimino-2-(2-formamidothiazol-4-yl)-acetamido]-3-[1-(2-propynyl)-1H-tetrazol-5-yl]-thiomethyl-3-cephem-4-carboxylic acid (syn isomer).

I.R. (Nujol): 3250, 2140, 1770, 1670 cm$^{-1}$

(19) 7-[2-Allyloxyimino-2-(2-aminothiazol-4-yl)-acetamido]-3-[1-(2-propynyl)-1H-tetrazol-5-yl]-thiomethyl-3-cephem-4-carboxylic acid (syn isomer).

I.R. (Nujol): 3260, 2110, 1750, 1670, 1630 cm$^{-1}$

(20) 7-[2-(2-Cyclopenten-1-yl)oxyimino-2-(2-formamidothiazol-4-yl)acetamido]-3-[1-(2-propynyl)-1H-tetrazol-5-yl]thiomethyl-3-cephem-4-carboxylic acid (syn isomer).

I.R. (Nujol): 3240, 2125, 1775, 1680 cm$^{-1}$

(21) 7-[2-(2-Cyclopenten-1-yl)oxyimino-2-(2-aminothiazol-4-yl)acetamido]-3-[1-(2-propynyl)-1H-tetrazol-5-yl]-thiomethyl-3-cephem-4-carboxylic acid (syn isomer).

I.R. (Nujol): 3270, 2120, 1775, 1670 cm$^{-1}$

(22) 7-[2-Isopropoxyimino-2-(2-formamidothiazol-4-yl)-acetamido]-3-[1-(2-propynyl)-1H-tetrazol-5-yl]-thiomethyl-3-cephem-4-carboxylic acid (syn isomer).

N.M.R. (DMSO-d$_6$, δ): 1.20 (6H, d, J=6 Hz), 3.53–3.75 (3H, m), 4.35 (2H, m), 5.13 (1H, d, J=5 Hz), 5.90 (2H, d, J=2 Hz), 5.78 (1H, dd, J=5 and 8 Hz), 7.34 (1H, s), 8.48 (1H, s), 9.57 (1H, d, J=8 Hz)

(23) 7-[2-Isopropoxyimino-2-(2-aminothiazol-4-yl)-acetamido]-3-[1-(2-propynyl)-1H-tetrazol-5-yl]-thiomethyl-3-cephem-4-carboxylic acid (syn isomer).

I.R. (Nujol): 3320, 2150, 1775, 1670 cm$^{-1}$

(24) 7-[2-(2-Propynyl)oxyimino-2-(2-formamidothiazol-4-yl)acetamido]-3-[1-(2-propynyl)-1H-tetrazol-5-yl]-thiomethyl-3-cephem-4-carboxylic acid (syn isomer).

I.R. (Nujol): 3240, 2120, 1770, 1665 cm$^{-1}$

(25) 7-[2-(2-Propynyl)oxyimino-2-(2-aminothiazol-4-yl)-acetamido]-3-[1-(2-propynyl)-1H-tetrazol-5-yl]thiomethyl-3-cephem-4-carboxylic acid (syn isomer).

I.R. (Nujol): 3280, 2110, 1770, 1670 cm$^{-1}$

(26) 7-[2-(2-Formamidothiazol-4-yl]glyoxylamido]-3-[1-(2-propynyl)-1H-tetrazol-5-yl]thiomethyl-3-cephem-4-carboxylic acid.

I.R. (Nujol): 3260, 3120, 2130, 1765, 1715, 1670 cm$^{-1}$

(27) 7-[2-(2-Aminothiazol-4-yl)glyoxylamido]-3-[1-(2-propynyl)-1H-tetrazol-5-yl]thiomethyl-3-cephem-4-carboxylic acid.

I.R. (Nujol): 3250, 2125, 1765, 1665, 1630 cm$^{-1}$

(28) 7-[2-(2-Aminothiazol-4-yl)-D,L-glycolamido]-3-[1-(2-propynyl)-1H-tetrazol-5-yl]thiomethyl-3-cephem-4-carboxylic acid.

I.R. (Nujol): 3260, 2140, 1770, 1680, 1630 cm$^{-1}$

(29) 7-[2-Benzyloxyimino-2-[2-(2,2,2-trifluoroacetamido)-thiazol-4-yl]acetamido]-3-[1-(2-propynyl)-1H-tetrazol-5-yl]thiomethyl-3-cephem-4-carboxylic acid (syn isomer).

I.R. (Nujol): 3280, 3230, 2140, 1785, 1725, 1655 cm$^{-1}$

(30) 7-[2-Benzyloxyimino-2-(2-aminothiazol-4-yl)-acetamido]-3-[1-(2-propynyl)-1H-tetrazol-5-yl]-thiomethyl-3-cephem-4-carboxylic acid (syn isomer).

I.R. (Nujol): 3270, 2110, 1770, 1665 cm$^{-1}$

(31) 7-[D-2-Formyloxy-2-phenylacetamido]-3-[1-(2-propynyl)-1H-tetrazol-5-yl]thiomethyl-3-cephem-4-carboxylic acid.

I.R. (Nujol): 3260, 2130, 1775, 1715 cm$^{-1}$

(32) 7-(2-Phenyl-D-glycolamido)-3-[1-(2-propynyl)-1H-tetrazol-5-yl]thiomethyl-3-cephem-4-carboxilic acid.

I.R. (Nujol): 3300, 3260, 2130, 1775, 1680 cm$^{-1}$

(33) 7-[2-tert-Butoxycarbonylmethoxyimino-2-(2-formamidothiazol-4-yl)acetamido]-3-[1-(2-propynyl)-1H-tetrazol-5-yl]thiomethyl-3-cephem-4-carboxylic acid (syn isomer).

I.R. (Nujol): 3240, 2130, 1780, 1720, 1675 cm$^{-1}$

(34) 7-[2-tert-Butoxycarbonylmethoxyimino-2-(2-aminothiazol-4-yl)acetamido]-3-[1-(2-propynyl)-1H-tetrazol-5-yl]thiomethyl-3-cephem-4-carboxylic acid hydrochloride (syn isomer).

I.R. (Nujol): 3350, 3230, 2125, 1770, 1715, 1675, 1625 cm$^{-1}$

(35) 7-[2-Carboxymethoxyimino-2-(2-aminothiazol-4-yl)acetamido]-3-[1-(2-propynyl)-1-H-tetrazol-5-yl]thiomethyl-3-cephem-4-carboxylic acid hydrochloride (syn isomer).

I.R. (Nujol): 3260, 2120, 1765, 1660, 1625 cm$^{-1}$

(36) 7-[2-Ethoxyimino-2-(2-aminothiazol-4-yl)acetamido]-3-[1-(2-propynyl)-1H-tetrazol-5-yl]thiomethyl-3-cephem-4-carboxylic acid (syn isomer).

IR (Nujol): 3250, 2100, 1770, 1670, 1625 cm$^{-1}$

(37) 7-[2-Ethoxyimino-2-(2-formamidothiazol-4-yl)-acetamido]-3-[1-(2-propynyl)-1H-tetrazol-5-yl]-thiomethyl-3-cephem-4-carboxylic acid (syn isomer).

IR (Nujol): 3250, 3150, 2140, 1770, 1680, 1650 cm$^{-1}$

(38) 7-[2-Cyclopentyloxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer), mp. 145° to 150° C. (dec.).

IR (Nujol): 3300, 3200, 2120, 1775, 1680, 1620, 1520 cm$^{-1}$

(39) 7-[2-(2-Cyclopenten-1-yl)oxyimino-2-(5-amino-1,2,4-thiadiazol-3-yl)acetamido-3-[1-(2-propynyl)-1H-tetrazol-5-yl]thiomethyl-3-cephem-4-carboxylic acid (syn isomer), mp. 145° to 150° C. (dec.).

IR (Nujol): 3300, 3200, 2120, 1770, 1675, 1620 1520 cm$^{-1}$

(40) 7-[2-tert-Butoxycarbonylmethoxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer), mp. 120° to 125° C. (dec.).

IR (Nujol): 3300, 1770, 1720, 1680, 1620, 1520 cm$^{-1}$

(41) 7-[2-Carboxymethoxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer), mp. 160° to 165° C. (dec.).

IR (Nujol): 3300, 3250, 1770, 1720, 1680, 1620, 1520 cm$^{-1}$

(42) 7-(D-2-tert-Butoxycarbonylamino-2-phenylacetamido)-3-[1-(2-propynyl)-1H-tetrazol-5-yl]-thiomethyl-3-cephem-4-carboxylic acid.

IR (Nujol): 3260, 2130, 1775, 1700, 1685 1660 cm$^{-1}$

(43) 7-(D-2-Phenylglycylamino)-3-[1-(2-propynyl)-1H-tetrazol-5-yl]thiomethyl-3-cephem-4-carboxylic acid trifluoroacetate.

IR (Nujol): 3250, 2130, 1775, 1660 cm$^{-1}$

(44) 7-(2-Allylthioacetamido)-3-[1-(2-propynyl)-1H-tetrazol-5-yl]thiomethyl-3-cephem-4-carboxylic acid.

IR (KBr): 3250, 2940, 2110, 1770, 1710 cm$^{-1}$

EXAMPLE 9

A mixture of phosphorus pentachloride (5.3 g) in methylene chloride (80 ml) was cooled to 5° C. and thereto was added pyridine (2.0 g). The mixture was stirred for 30 minutes at room temperature and then cooled to 5° C. and thereto was added benzhydryl 7-(2-phenylacetamido)-3-[1-(2-propynyl)-1H-tetrazol-5-yl]thiomethyl-3-cephem-4-carboxylate (8.0 g) to give a homogeneous solution. The obtained solution was stirred for 30 minutes at 5° C. and added to methanol (40.2 g) precooled to −30° C. The resulting mixture was stirred for 30 minutes without external cooling. The reaction mixture was evaporated and to the residue were added ethyl acetate and water. The mixture was adjusted to pH 7.0 with a saturated aqueous solution of sodium carbonate. The ethyl acetate layer was separated, washed with water (x3), dried over magnesium sulfate, treated with activated charcoal and evaporated under reduced pressine to give benzhydryl 7-amino-3-[1-(2-propynyl)-1H-tetrazol-5-yl]thiomethyl-3-cephem-4-carboxylate (6.17 g).

I.R. (Nujol): 3270, 2140, 1770, 1720, 1620 cm$^{-1}$

N.M.R. (DMSO-d$_6$, δ): 3.45–3.90 (3H, m), 4.30 (2H, q, J=14.0 Hz), 4.85 (1H, d, J=5.0 Hz), 5.02 (1H, d, J=5.0 Hz), 5.28 (2H, d, J=2.0 Hz), 6.90 (1H, s), 7.10–7.68 (10H, m)

EXAMPLE 10

A mixture of phosphorus pentachloride (8.5 g) in methylene chloride (130 ml) was cooled to 5° C. and thereto was added pyridine (3.2 g). The mixture was stirred for 30 minutes at room temperature, cooled to 5° C. and thereto was added benzhydryl 7-(2-phenylacetamido)-3-[2-(2-propynyl)-2H-tetrazol-5-yl]thiomethyl-3-cephem-4-carboxylate (13.0 g) to give a homogeneous solution. The obtained solution was stirred for 30 minutes at 5° C. and added to methanol (65.4 g) precooled to −30° C. The resulting mixture was stirred for 30 minutes without external cooling. The reaction mixture was evaporated and to the residue were added ethyl acetate and water. The mixture was adjusted to pH 7.0 with a saturated aqueous solution of sodium carbonate. The ethyl acetate layer was separated, washed with water (x3), dried over magnesium sulfate, treated with activated charcoal and evaporated under reduced pressure to give benzhydryl 7-amino-3-[2-(2-propynyl)-2H-tetrazol-5-yl]thiomethyl-3-cephem-4-carboxylate (7.31 g).

I.R. (Film): 3400, 3270, 2950, 2850, 2140, 1770, 1710, 1615 cm$^{-1}$

N.M.R. (DMSO-d$_6$, δ): 3.40–3.83 (3H, m), 4.19 (2H, q, J=13.2 Hz), 4.84 (1H, d, J=4.0 Hz), 5.02 (1H, d, J=4.0 Hz), 5.62 (2H, d, J=2.0 Hz), 6.92 (1H, s), 7.07–7.72 (10H, m)

EXAMPLE 11

The following compounds were prepared according to the similar manners to those of Examples 9 and 10.

(1) 7-Amino-3-[1-(2-propynyl)-1H-tetrazol-5-yl]-thiomethyl-3-cephem-4-carboxylic acid.

I.R. (Nujol): 3250, 3160, 2130 cm$^{-1}$ (2) 7-Amino-3-[2-(2-propynyl)-2H-tetrazol-5-yl]-thiomethyl-3-cephem-4-carboxylic acid.

I.R. (Nujol): 3260, 3150, 1800 cm$^{-1}$

EXAMPLE 12

A mixture of benzhydryl 7-amino-3-[1-(2-propynyl)-1H-tetrazol-5-yl]thiomethyl-3-cephem-4-carboxylate (2.0 g), trimethylsilylacetamide (2.5 g) in dry ethyl acetate (40.0 ml) was stirred at room temperature to give a homogeneous solution (solution A). On the other hand, Vilsmeir Reagent was prepared from dry N,N-dimethylformamide (0.41 g), dry ethyl acetate (1.64 ml) and phosphoryl chloride (0.85 g) in a conventional manner. Thereto were added dry tetrahydrofuran (16.0 ml) and 2-methoxyimino-2-(2-formamidothiazol-4-yl)acetic acid (syn isomer) (1.1 g) and the resulting mixture was stirred at 0° to 30° C. to give an activated solution. The activated solution was added to Solution A precooled to −10° C. and the resulting solution was stirred for 30 minutes at −10° to −5° C. After the addition of water to the reaction mixture, the organic layer was separated, washed successively with a saturated aqueous solution of sodium bicarbonate and a saturated aqueous solution of sodium chloride, dried over magnesium sulfate, treated with activated charcoal and then evaporated. The residue was pulverized in isopropyl ether, collected by filtration, washed with isopropyl ether and dried to give benzhydryl 7-[2-methoxyimino-2-(2-formamido-thiazol-4-yl)acetamido]-3-[1-(2-propynyl)-1H-tetrazol-5-yl]thiomethyl-3-cephem-4-caboxylate (syn isomer) (2.51 g).

I.R. (Nujol): 3150, 2140, 1780, 1680, 1645 cm$^{-1}$

N.M.R. (DMSO-d$_6$, δ): 3.52–3.88 (3H, m), 3.94 (3H, s), 4.37 (2H, q, J=14.0 Hz), 5.64 (1H, d, J=5.0 Hz), 5.32 (2H, d, J=3.0 Hz), 5.97 (1H, dd, J=5.0 and 8.0 Hz), 6.96 (1H, s), 7.28–7.73 (11H, m), 8.56 (1H, s), 9.73 (1H, d, J=8.0 Hz), 12.60 (1H, broad s).

EXAMPLE 13

A mixture of benzhydryl 7-amino-3-[2-(2-propynyl)-2H-tetrazol-5-yl]thiomethyl-3-cephem-4-carboxylate (2.0 g), trimethylsilylacetamide (2.5 g) in dry ethyl acetate (40 ml) was stirred at room temperature to give a homogeneous solution (Solution A). On the other hand, Vilsmeir Reagent was prepared from dry N,N-dimethylformamide (0.41 g), dry ethyl acetate (1.64 ml) and phosphoryl chloride (0.85 g) in a conventional manner. Thereto were added dry tetrahydrofuran (20 ml) and 2-methoxyimino-2-(2-formamidothiazol-4-yl)acetic acid (syn isomer) (1.1 g) and the resulting mixture was stirred at 0° to 3° C. to give an activated solution. The activated solution was added to Solution A precooled to −10° C. and the resulting solution was stirred for 30 minutes at 0° to 5° C. After the addition of water to the reaction mixture, the organic layer was separated, washed successively with a saturated aqueous solution of sodium bicarbonate (x3) and a saturated aqueous solution of sodium chloride (x2), dried over magnesium sulfate, treated with activated charcoal and then evaporated. The residue was pulverized in isopropyl ether, collected by filtration, washed with isopropyl ether and dried to give benzhydryl 7-[2-methoxyimino-2-(2-formamidothiazol-4-yl)acetamido]-3-[2-(2-propynyl)-2H-tetrazol-5-yl]thiomethyl-3-cephem-4-carboxylate (syn isomer) (2.85 g).

I.R. (Nujol): 3250, 2140, 1780, 1720, 1670 cm$^{-1}$
N.M.R. DMSO-d$_6$, δ): 3.61–3.84 (3H, m), 3.93 (3H, s), 4.27 (2H, q, J=14.0 Hz), 5.23 (1H, d, J=5.0 Hz), 5.62 (2H, d, J=2.0 Hz), 5.83 (1H, dd, J=5.0 and 8.0 Hz), 6.94 (1H, m), 7.14–7.74 (11H, m), 8.52 (1H, s), 9.70 (1H, d, J=8.0 Hz).

EXAMPLE 14

A mixture of 7-amino-3-[1-(2-propynyl)-1H-tetrazol-5-yl]thiomethyl-3-cephem-4-carboxylic acid (1.70 g), trimethylsilylacetamide (6.3 g) in dry ethyl acetate (34 ml) was stirred for 30 minutes at 40° C. to give a homogeneous solution (Solution A). On the other hand, Vilsmeir Reagent was prepared from dry N,N-dimethylformamide (0.42 g), dry ethyl acetate (1.6 ml) and phosphoryl chloride (0.89 g) in a conventional manner. Thereto were added dry ethyl acetate (14 ml) and 2-cyclopentyloxyimino-2-[2-(2,2,2-trifluoroacetamido)-thiazol-4-yl]acetic acid (syn isomer) (1.69 g) and the resulting mixture was stirred to give an activated solution. The activated solution was added to Solution A precooled to −10° C. to −15° C. and the resulting solution was stirred for 40 minutes at −10° to −15° C. After the addition of water (30 ml) and ethyl acetate (20 ml) to the reaction mixture, the organic layer was separated, and then extracted with a saturated aqueous solution of sodium bicarbonate. To the extract was added ethyl acetate (50 ml) and the mixture was adjusted to pH 2.0 with 10% hydrochloric acid. The organic layer was separated, washed with a saturated aqueous solution of sodium chloride, dried and then evaporated. The residue was pulverized in isopropyl ether to give 7-[2-cyclopentyloxyimino-2-[2-(2,2,2-trifluoroacetamido)-thiazol-4-yl]acetamido]-3-[1-(2-propynyl)-1H-tetrazol-5-yl]thiomethyl-3-cephem-4-carboxylic acid (syn isomer) (2.72 g).

I.R. (Nujol): 3260, 2130, 1785, 1720, 1680 cm$^{-1}$
N.M.R. (DMSO-d$_6$): 1.33–2.07 (8H, m), 3.60 (1H, m), 3.67 (2H, m), 4.38 (2H, ABq, J=13 Hz), 4.72 (1H, m), 5.16 (1H, d, J=5 Hz), 5.32 (2H, d, J=2 Hz), 5.84 (1H, dd, J=5 and 8 Hz), 7.50 (1H, s), 9.65 (1H, d, J=8 Hz).

EXAMPLE 15

Vilsmeier reagent was prepared from N,N-dimethylformamide (0.4 g) and phosphoryl chloride (0.8 g) in a conventional manner. 2-Ethoxyimino-2-(2-formamidothiazol-4-yl)acetic acid (syn isomer) (1.1 g) was added to the stirred suspension of Vilsmeier reagent in dry tetrahydrofuran (15 ml) under ice cooling and stirred for 30 minutes at same temperature [Solution A]. Trimethylsilylacetamide (4.5 g) was added to the stirred suspension of 7-amino-3-[1-(2-propynyl)-1H-tetrazol-5-yl]thiomethyl-3-cephem-4-carboxylic acid (1.5 g) in dry ethyl acetate (30 ml). To the solution obtained was dropwise added the Solution A at −10° C. and the resulting solution was stirred at same temperature for 0.5 hours. Water (40 ml) was added to the resulting solution, and the separated organic layer was added to water, and the mixture was adjusted to pH 7.5 with a saturated aqueous solution of sodium bicarbonate. The separated aqueous layer was adjusted to pH 2.0 with 10% hydrochloric acid and extracted with ethyl acetate. The extract was washed with a saturated aqueous solution of sodium chloride, dried over magnesium sulfate and then evaporated to give 7-[2-ethoxyimino-2-(2-formamidothiazol-4-yl)acetamido]-3-[1-(2-propynyl)-1H-tetrazol-5-yl]thiomethyl-3-cephem-4-carboxylic acid (syn isomer) (1.72 g).

I.R. (Nujol): 3250, 3150, 2140, 1770, 1680, 1650 cm$^{-1}$
N.M.R. (DMSO-d$_6$, δ): 1.26 (3H, t, J=7.0 Hz), 3.55–3.87 (3H, m), 4.17 (2H, q, J=7.0 Hz), 4.41 (2H, q, J=14.0 Hz), 5.16 (1H, d, J=5.0 Hz), 5.33 (2H, d, J=2.0 Hz), 5.85 (1H, dd, J=5.0 and 8.0 Hz), 7.41 (1H, s), 8.53 (1H, s), 9.64 (1H, d, J=8.0 Hz), 12.68 (1H, broad s).

EXAMPLE 16

To a solution of phosphorus pentachloride (2.50 g) in methylene chloride (60 ml) was added 2-tert-butoxycarbonylmethoxyimino-2-(5-amino-1,2,4-thiadiazol-3-yl)acetic acid (syn isomer)(3.02 g) at −15° C. and the mixture was stirred for 45 minutes at −10° to −13° C. On the other hand, a mixture of 7-amino-3-[1-(2-propynyl)-1H-tetrazol-5-yl]thiomethyl-3-cephem-4-carboxylic acid (3.52 g) and trimethylsilylacetamide (10 g) in methylene chloride (50 ml) was warmed to make a clear solution and then cooled to −10° C. The solution was added to the above activated mixture at a time and the mixture was stirred for 15 minutes at −5° to 10° C. The reaction mixture was poured into an aqueous solution (120 ml) of sodium bicarbonate (6.7 g) and stirred for 30 minutes at room temperature. The aqueous layer was separated and ethyl acetate was added thereto. The resulting mixture was adjusted to pH 3 with 6 N hydrochloric acid. The ethyl acetate layer was separated, dried over magnesium sulfate and then evaporated. The residue was pulverized with isopropyl ether and then dried to give 7-[2-tert-butoxycarbonylmethoxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer)(3.8 g), mp. 120° to 125° C. (dec.).

IR (Nujol): 3300, 1770, 1720, 1680, 1620, 1520 cm$^{-1}$
NMR (DMSO-d$_6$, δ): 1.37 (9H, s), 3.57 (1H, t, J=3 Hz), 3.60 (2H, broad s), 4.30 (2H, broad s), 4.57 (2H, s), 5.07 (1H, d, J=4 Hz), 5.25 (2H, d, J=3 Hz), 5.77 (1H, 2 d, J=4 and 8 Hz), 8.08 (2H, s), 9.45 (1H, d, J=8 Hz).

EXAMPLE 17

The following compounds were prepared according to the similar manners to those of Examples 12 to 16

(1) Benzhydryl 7-(2-phenylacetamido)-3-[1-(2-propynyl)-1H-tetrazol-5-yl]thiomethyl-3-cephem-4-carboxylate-1-oxide.

I.R. (Nujol): 3250, 2130, 1780, 1720, 1665 cm$^{-1}$ (2) Benzhydryl 7-(2-phenylacetamido)-3-[2-(2-propynyl)-2H-tetrazol-5-yl]thiomethyl-3-cephem-4-carboxylate-1-oxide.

I.R. (Nujol): 3320, 2140, 1775, 1710, 1640 cm$^{-1}$ (3) Benzhydryl 7-(2-phenylacetamido)-3-[1-(2-propynyl)-1H-tetrazol-5-yl]thiomethyl-3-cephem-4-caboxylate I.R. (Nujol): 3260, 2130, 1770, 1710, 1660 cm$^{-1}$ (4) Benzhydryl 7-(2-phenylacetamido)-3-[2-(2-propynyl)-2H-tetrazol-5-yl]thiomethyl-3-cephem-4-carboxylate.

I.R. (Nujol): 3280, 2140, 1770, 1710, 1660 cm$^{-1}$ (5) 7-[2-Methoxyimino-2-(2-formamidothiazol-4-yl)-acetamido]-3-[1-(2-propynyl)-1H-tetrazol-5-yl]-thiomethyl-3-cephem-4-carboxylic acid (syn isomer).

I.R. (Nujol): 3250, 2150, 1780, 1680 cm$^{-1}$ (6) 7-[2-Methoxyimino-2-(2-aminothiazol-4-yl)acetamido]-3-[1-(2-propynyl)-1H-tetrazol-5-yl]thiomethyl-3-cephem-4-carboxylic acid (syn isomer).

I.R. (Nujol): 3280, 2100, 1770, 1660, 1630 cm$^{-1}$ (7) Benzhydryl 7-[2-methoxyimino-2-(2-aminothiazol-4-yl)acetamido]-3-[2-(2-propynyl)-2H-tetrazol-5-yl]-thiomethyl-3-cephem-4-carboxylate (syn isomer).

I.R. (Nujol): 3270, 2150, 1775, 1725, 1670, 1680 cm$^{-1}$ (8) 7-[2-Methoxyimino-2-(2-aminothiazol-4-yl)acetamido]-3-[2-(2-propynyl)-2H-tetrazol-5-yl]thiomethyl-3-cephem-4-carboxylic acid (syn isomer).

I.R. (Nujol): 3300, 2100, 1770, 1660, 1630 cm$^{-1}$ (9) 7-[2-Cyclopentyloxyimino-2-(2-aminothiazol-4-yl)-acetamido]-3-[1-(2-propynyl)-1H-tetrazol-5-yl]-thiomethyl-3-cephem-4-carboxylic acid (syn isomer).

I.R. (Nujol): 3260, 2110, 1780, 1665 cm$^{-1}$

(10) Benzhydryl 7-[2-Methoxyimino-2-(5-amino-1,2,4-thiadiazol-3-yl)acetamido]-3-[1-(2-propynyl)-1H-tetrazol-5-yl]thiomethyl-3-cephem-4-carboxylate (syn isomer).

I.R. (Nujol): 3250, 2130, 1770, 1720, 1660, 1620 cm$^{-1}$

N.M.R. (DMSO-d$_6$, δ): 3.43–3.90 (3H, m), 3.93 (3H, s), 4.33 (2H, q, J=15.0 Hz), 5.22 (1H, d, J=5.0 Hz), 5.31 (2H, d, J=2.0 Hz), 5.96 (1H, dd, J=5.0 and 8.0 Hz), 6.95 (1H, s), 7.10–7.73 (10H, m), 9.67 (1H, d, J=8.0 Hz).

(11) 7-[2-Methoxyimino-2-(5-amino-1,2,4-thiadiazol-3-yl)acetamido]-3-[1-(2-propynyl)-1H-tetrazol-5-yl]-thiomethyl-3-cephem-4-carboxylic acid (syn isomer).

I.R. (Nujol): 3300, 1770, 1670, 1620 cm$^{-1}$

(12) 7-[2-Methoxyimino-2-(thiazol-4-yl)acetamido]-3-[1-(2-propynyl)-1H-tetrazol-5-yl]thiomethyl-3-cephem-4-carboxylic acid (syn isomer).

I.R. (Nujol): 3310, 2150, 1785, 1725, 1680 cm$^{-1}$

N.M.R. (DMSO-d$_6$, δ): 3.63–3.87 (3H, m), 3.97 (3H, s), 4.44 (2H, ABq, J=13 Hz), 5.23 (1H, d, J=5 Hz), 5.41 (2H, d, J=2.5 Hz), 5.87 (1H, dd, J=5 and 8 Hz), 8.08 (1H, d, J=1.5 Hz), 9.34 (1H, d, J=1.5 Hz), 9.85 (1H, d, J=8 Hz)

(13) 7-[2-(1H-Tetrazol-1-yl)acetamido]-3-[1-(2-propynyl)-1H-tetrazol-5-yl]thiomethyl-3-cephem-4-carboxylic acid.

I.R. (Nujol): 3260, 2110, 1770, 1695 cm$^{-1}$

N.M.R. (DMSO-d$_6$, δ): 3.66 (1H, d, J=2.5 Hz), 3.71 (2H, ABq, J=15 Hz), 4.40 (2H, ABq, J=13 Hz), 5.10 (1H, d, J=5 Hz), 5.33 (2H, d, J=2.5 Hz), 5.37 (2H, s), 5.73 (1H, dd, J=5 and 8 Hz), 9.34 (1H, s), 9.51 (1H, d, J=8 Hz)

(14) Benzhydryl 7-[2-allyloxyimino-2-(2-formamidothiazol-4-yl)acetamido]-3-[1-(2-propynyl)-1H-tetrazol-5-yl]-thiomethyl-3-cephem-4-carboxylate (syn isomer).

I.R. (Nujol): 3250, 2150, 1780, 1680 cm$^{-1}$

N.M.R. (DMSO-d$_6$, δ): 3.43–3.94 (3H, m), 4.35 (2H, m), 4.66 (2H, m), 5.03–5.56 (3H, m), 5.28 (2H, d, J=2.0 Hz), 5.60–6.39 (2H, m), 6.93 (1H, s), 7.13–7.70 (11H, m), 8.55 (1H, s), 12.70 (1H, broad s)

(15) 7-[2-Allyloxyimino-2-(2-formamidothiazol-4-yl)-acetamido]-3-[1-(2-propynyl)-1H-tetrazol-5-yl]-thiomethyl-3-cephem-4-carboxylic acid (syn isomer).

I.R. (Nujol): 3250, 2140, 1770, 1670 cm$^{-1}$

(16) 7-[2-Allyloxyimino-2-(2-aminothiazol-4-yl)acetamido]-3-[1-(2-propynyl)-1H-tetrazol-5-yl]thiomethyl-3-cephem-4-carboxylic acid (syn isomer).

I.R. (Nujol): 3260, 2110, 1750, 1670, 1630 cm$^{-1}$

(17) 7-[2-(2-Cyclopenten-1-yl)oxyimino-2-(2-formamidothiazol-4-yl)acetamido]-3-[1-(2-propynyl)-1H-tetrazol-5-yl]thiomethyl-3-cephem-4-carboxylic acid (syn isomer).

I.R. (Nujol): 3240, 2125, 1775, 1680 cm$^{-1}$

N.M.R. (DMSO-d$_6$, δ): 1.73–2.60 (4H, m), 3.57–3.83 (3H, m), 4.38 (2H, ABq, J=14 Hz), 5.12 (1H, d, J=5 Hz), 5.17–5.50 (3H, m), 5.66–6.23 (3H, m), 7.39 (1H, s), 8.50 (1H, s), 9.57 (1H, d, J=8 Hz)

(18) 7-[2-(2-Cyclopenten-1-yl)oxyimino-2-(2-aminothiazol-4-yl)acetamido]-3-[1-(2-propynyl)-1H-tetrazol-5-yl]thiomethyl-3-cephem-4-carboxylic acid (syn isomer).

I.R. (Nujol): 3270, 2120, 1775, 1670 cm$^{-1}$

(19) 7-[2-Isopropoxyimino-2-(2-formamidothiazol-4-yl)-acetamido]-3-[1-(2-propynyl)-1H-tetrazol-5-yl]-thiomethyl-3-cephem-4-carboxylic acid (syn isomer).

N.M.R. (DMSO-d$_6$, δ): 1.20 (6H, d, J=6 Hz), 3.53–3.75 (3H, m), 4.35 (2H, m), 5.13 (1H, d, J=5 Hz), 5.90 (2H, d, J=2 Hz), 5.78 (1H, dd, J=5 and 8 Hz), 7.34 (1H, s), 8.48 (1H, s), 9.57 (1H, d, J=8 Hz)

(20) 7-[2-Isopropoxyimino-2-(2-aminothiazol-4-yl)-acetamido]-3-[1-(2-propynyl)-1H-tetrazol-5-yl]-thiomethyl-3-cephem-4-carboxylic acid (syn isomer).

I.R. (Nujol): 3320, 2150, 1775, 1670 cm$^{-1}$

(21) 7-[2-(2-Propynyl)oxyimino-2-(2-formamidothiazol-4-yl)acetamido]-3-[1-(2-propynyl)-1H-tetrazol-5-yl]-thiomethyl-3-cephem-4-carboxylic acid (syn isomer).

I.R. (Nujol): 3240, 2120, 1770, 1665 cm$^{-1}$

N.M.R. (DMSO-d$_6$, δ): 3.45 (1H, t, J=2 Hz), 3.57–3.80 (2H, m), 4.36 (2H, ABq, J=14 Hz), 4.72 (2H, d, J=2 Hz), 5.10 (1H, d, J=5 Hz), 5.28 (2H, d, J=2 Hz), 5.77 (1H, dd, J=5 and 8 Hz), 7.41 (1H, s), 8.47 (1H, s), 9.70 (1H, d, J=8 Hz)

(22) 7-[2-(2-Propynyl)oxyimino-2-(2-aminothiazol-4-yl)-acetamido]-3-[1-(2-propynyl)-1H-tetrazol-5-yl]-thiomethyl-3-cephem-4-carboxylic acid (syn isomer).

I.R. (Nujol): 3280, 2110, 1770, 1670 cm$^{-1}$

(23) 7-[2-(2-Formamidothiazol-4-yl)glyoxylamido]-3-[1-(2-propynyl)-1H-tetrazol-5-yl]thiomethyl-3-cephem-4-carboxylic acid.

I.R. (Nujol): 3260, 3120, 2130, 1765, 1715, 1670 cm$^{-1}$

N.M.R. (DMSO-d$_6$, δ): 3.63–3.87 (3H, m), 4.45 (2H, ABq, J=14 Hz), 5.20 (1H, d, J=5 Hz), 5.37 (2H, d, J=2 Hz), 5.87 (1H, dd, J=5 and 8 Hz), 8.46 (1H, s), 8.61 (1H, s), 9.87 (1H, d, J=8 Hz)

(24) 7-[2-(2-Aminothiazol-4-yl)glyoxylamido]-3-[1-(2-propynyl)-1H-tetrazol-5-yl]thiomethyl-3-cephem-4-carboxylic acid.

I.R. (Nujol): 3250, 2125, 1765, 1665, 1630 cm$^{-1}$

(25) 7-[2-(2-Aminothiazol-4-yl)-D,L-glycolamido]-3-[1-(2-propynyl)-1H-tetrazol-5-yl]thiomethyl-3-cephem-4-carboxylic acid.

I.R. (Nujol): 3260, 2140, 1770, 1680, 1630 cm$^{-1}$

(26) 7-[2-Benzyloxyimino-2-[2-(2,2,2-trifluoroacetamido)-thiazol-4-yl]acetamido]-3-[1-(2-propynyl)-1H-tetrazol-5-yl]thiomethyl-3-cephem-4-carboxylic acid (syn isomer).

I.R. (Nujol): 3280, 3230, 2140, 1785, 1725, 1655 cm$^{-1}$

N.M.R. (DMSO-d$_6$, δ): 3.50–3.77 (3H, m), 4.37 (2H, ABq, J=13 Hz), 5.13 (1H, d, J=5 Hz), 5.21 (2H, m), 5.32 (2H, d, J=2 Hz), 5.84 (1H, dd, J=5 and 8 Hz), 7.37 (5H, m), 7.53 (1H, s), 9.80 (1H, d, J=8 Hz)

(27) 7-[2-Benzyloxyimino-2-(2-aminothiazol-4-yl)-acetamido]-3-[1-(2-propynyl)-1H-tetrazol-5-yl]-thiomethyl-3-cephem-4-carboxylic acid (syn isomer).

I.R. (Nujol): 3270, 2110, 1770, 1665 cm$^{-1}$

(28) 7-[D-2-Formyloxy-2-phenylacetamido]-3-[1-(2-propynyl)-1H-tetrazol-5-yl]thiomethyl-3-cephem-4-carboxylic acid.

I.R. (Nujol): 3260, 2130, 1775, 1715 cm$^{-1}$

N.M.R. (DMSO-d$_6$, δ): 3.33–3.64 (3H, m), 4.23 (2H, ABq, J=14 Hz), 4.89 (1H, d, J=5 Hz), 5.32 (2H, d,

J=2 Hz), 5.70 (1H, dd, J=5 and 8 Hz), 6.12 (1H, s), 7.27–7.66 (5H, m), 8.37 (1H, s), 9.36 (1H, d, J=8 Hz)

(29) 7-(2-Phenyl-D-glycolamido)-3-[1-(2-propynyl)-1H-tetrazol-5-yl]thiomethyl-3-cephem-4-carboxylic acid.

I.R. (Nujol): 3300, 3260, 2130, 1775, 1680 cm$^{-1}$

(30) 7-[2-tert-Butoxycarbonylmethoxyimino-2-(2-formamidothiazol-4-yl)acetamido]-3-[1-(2-propynyl)-1H-tetrazol-5-yl]thiomethyl-3-cephem-4-carboxylic acid (syn isomer).

I.R. (Nujol): 3240, 2130, 1780, 1720, 1675 cm$^{-1}$
N.M.R. (DMSO-d$_6$, δ): 1.49 (9H, s), 3.63–3.87 (3H, m), 4.41 (2H, ABq, J=14 Hz), 4.64 (2H, s), 5.16 (1H, d, J=5 Hz), 5.33 (2H, d, J=2 Hz), 5.85 (1H, dd, J=5 and 8 Hz), 7.45 (1H, s), 8.53 (1H, s), 9.60 (1H, d, J=8 Hz)

(31) 7-[2-tert-Butoxycarbonylmethoxyimino-2-(2-aminothiazol-4-yl)acetamido]-3-[1-(2-propynyl)-1H-tetrazol-5-yl]thiomethyl-3-cephem-4-carboxylic acid hydrochloride (syn isomer).

I.R. (Nujol): 3350, 3230, 2125, 1770, 1715, 1675, 1625 cm$^{-1}$

(32) 7-[2-Carboxymethoxyimino-2-(2-aminothiazol-4-yl)acetamido]-3-[1-(2-propynyl)-1H-tetrazol-5-yl]thiomethyl-3-cephem-4-carboxylic acid hydrochloride (syn isomer).

I.R. (Nujol): 3260, 2120, 1765, 1660, 1625 cm$^{-1}$

(33) 7-[2-Ethoxyimino-2-(2-aminothiazol-4-yl)acetamido]-3-[1-(2-propynyl)-1H-tetrazol-5-yl]thiomethyl-3-cephem-4-carboxylic acid (syn isomer).

I.R. (Nujol): 3250, 2100, 1770, 1670, 1625 cm$^{-1}$

(34) 7-[2-Cyclopentyloxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer), mp. 145° to 150° C. (dec.).

I.R. (Nujol): 3300, 3200, 2120, 1775, 1680, 1620, 1520 cm$^{-1}$
N.M.R. (DMSO-d$_6$, δ): 1.4–2.0 (8H, m), 3.63 (1H, t, J=3 Hz), 3.67 (2H, bs), 4.28,4.47 (2H, ABq, J=14 Hz), 4.60–4.83 (1H, m), 5.12 (1H, d, J=4 Hz), 5.32 (2H, d, J=3 Hz), 5.80 (1H, 2d, J=4 and 8 Hz), 8.10 (2H, s), 9.47 (1H, d, J=8 Hz)

(35) 7-[2-(2-Cyclopenten-1-yl)oxyimino-2-(5-amino-1,2,4-thiadiazol-3-yl)acetamido-3-[1-(2-propynyl)-1H-tetrazol-5-yl]thiomethyl-3-cephem-4-carboxylic acid (syn isomer), mp. 145° to 150° C. (dec.).

I.R. (Nujol): 3300, 3200, 2120, 1770, 1675, 1620, 1520 cm$^{-1}$
NMR (DMSO-d$_6$, δ): 1.8–2.5 (4H, m), 3.62 (1H, t, J=3 Hz), 3.67 (2H, bs), 4.27, 4.45 (2H, ABq, J=14 Hz), 5.08 (1H, d, J=4 Hz), 5.27–5.50 (1H, m), 5.32 (2H, d, J=3 Hz), 5.80 (1H, 2d, J=4 and 8 Hz), 5.83–6.17 (2H, m), 8.10 (2H, s), 9.48 (1H, d, J=8 Hz)

(36) 7-[2-Carboxymethoxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer), mp. 160° to 165° C. (dec.).

IR (Nujol): 3300, 3250, 1770, 1720, 1680, 1620, 1520 cm$^{-1}$

(37) 7-(D-2-tert-Butoxycarbonylamino-2-phenylacetamido)-3-[1-(2-propynyl)-1H-tetrazol-5-yl]thiomethyl-3-cephem-4-carboxylic acid.

IR (Nujol): 3260, 2130, 1775, 1700, 1685, 1660 cm$^{-1}$
NMR (DMSO-d$_6$, δ): 1.33 (9H, s), 3.60 (3H, m), 4.38 (2H, m), 4.90–5.81 (5H, m), 7.34 (5H, m), 9.12 (1H, d, J=8 Hz)

(38) 7-(D-2-Phenylglycylamino)-3-[1-(2-propynyl)-1H-tetrazol-5-yl]thiomethyl-3-cephem-4-carboxylic acid trifluoroacetate.

IR (Nujol): 3250, 2130, 1775, 1660 cm$^{-1}$

(39) 7-(2-Allylthioacetamido)-3-[1-(2-propynyl)-1H-tetrazol-5-yl]thiomethyl-3-cephem-4-carboxylic acid.

IR (KBr): 3250, 2940, 2110, 1770, 1710 cm$^{-1}$
NMR (DMSO-d$_6$, δ): 3.03–3.37 (4H, m), 3.60–3.83 (3H, m), 4.39 (2H, ABq, J=14 Hz), 4.98–6.17 (7H, m), 8.93 (1H, d, J=8 Hz).

EXAMPLE 18

To a mixture of benzhydryl 7-[2-methoxyimino-2-(2-formamidothiazol-4-yl)acetamido]-3-[1-(2-propynyl)-1H-tetrazol-5-yl]thiomethyl-3-cephem-4-carboxylate (syn isomer) (2.8 g) in methylene chloride (24 ml) were added anisole (2.8 g) and trifluoroacetic acid (7.5 g) with stirring under ice-cooling and then the resulting mixture was stirred for one hour and 15 minutes at room temperature. After the evaporation of the reaction mixture, to the residue were added water and ethyl acetate. The mixture was adjusted to pH 7.0 with a saturated aqueous solution of sodium carbonate. The aqueous layer was separated and washed with ethyl acetate (x2) and thereto were added ethyl acetate and tetrahydrofuran. The mixture was adjusted to pH 2.0 with 10% hydrochloric acid. The organic layer was separated, washed with water, dried over magnesium sulfate, treated with activated charcoal and evaporated. The residue was pulverized in isopropyl ether, collected by filtration, washed with isopropyl ether and dried to give 7-[2-methoxyimino-2-(2-formamidothiazol-4-yl)acetamido[-3-[1-(2-propynyl)-1H-tetrazol-5-yl]thiomethyl-3-cephem-4-carboxylic acid (syn isomer) (1.48 g).

I.R. (Nujol): 3250, 2150, 1780, 1680 cm$^{-1}$
N.M.R. (DMSO-d$_6$, δ): 3.48–3.81 (3.81 (3H, m), 3.89 (3H, s), 4.37 (2H, q, J=13.0 Hz), 5.11 (1H, d, J=5.0 Hz), 5.30 (2H, d, J=2.0 Hz), 5.79 (1H, dd, J=5.0 and 8.0 Hz), 7.37 (1H, s), 8.47 (1H, s), 9.60 (1H, d, J=8.0 Hz).

EXAMPLE 19

To a mixture of benzhydryl 7-[2-methoxyimino-2-(2-aminothiazol-4-yl)acetamido]-3-[2-(2-propynyl)-2H-tetrazol-5-yl]thiomethyl-3-cephem-4-carboxylate (syn isomer)(1.9 g) in methylene chloride (19.0 ml) were added anisole (2.3 g) and trifluoroacetic acid (6.2 g) with stirring under ice-cooling and then the resulting mixture was stirred for an hour at room temperature. After the evaporation of the reaction mixture, to the residue were added water and ethyl acetate. The organic layer was separated and adjusted to pH 7.0 with an aqueous solution of sodium bicarbonate. The aqueous layer was separated, washed with ethyl acetate (x2) and then concentrated. The concentrate was adjusted to pH 3.0 with 10% hydrochloric acid. The precipitates were collected by filtration, washed with water and then dried over phosphorus pentoxide to give 7-[2-methoxyimino-2-(2-aminothiazol-4-yl)acetamido]-3-[2-(2-propynyl)-2H-tetrazol-5-yl]thiomethyl-3-cephem-4-carboxylic acid (syn isomer) (0.95 g).

I.R. (Nujol): 3300, 2100, 1770, 1660, 1630 cm$^{-1}$
N.M.R. (DMSO-d$_6$, δ): 3.47–3.84 (3H, m), 3.86 (3H, s), 4.32 (2H, q, J=14.0 Hz), 5.13 (1H, d, J=4.0 Hz), 5.53–5.97 (3H, m), 6.76 (1H, s), 9.59 (1H, d, J=8.0 Hz).

EXAMPLE 20

The following compounds were prepared according to the similar manners to those of Examples 18 and 19.

(1) 7-Amino-3-[1-(2-propynyl)-1H-tetrazol-5-yl]thiomethyl-3-cephem-4-carboxylic acid.
I.R. (Nujol): 3250, 3160, 2130 cm$^{-1}$ (2) 7-Amino-3-[2-(2-propynyl)-2H-tetrazol-5-yl]-thiomethyl-3-cephem-4-carboxylic acid.
I.R. (Nujol): 3260, 3150, 1800 cm$^{-1}$ (3) 7-[2-Methoxyimino-2-(2-aminothiazol-4-yl)acetamido]-3-[1-(2-propynyl)-1H-tetrazol-5-yl]thiomethyl-3-cephem-4-carboxylic acid (syn isomer).
I.R. (Nujol): 3280, 2100, 1770, 1660, 1630 cm$^{-1}$ (4) 7-[2-Cyclopentyloxyimino-2-[2-(2,2,2-trifluoroacetamido)thiazol-4-yl]acetamido]-3-[1-(2-propynyl)-1H-tetrazol-5-yl]thiomethyl-3-cephem-4-carboxylic acid (syn isomer).
I.R. (Nujol): 3260, 2130, 1785, 1720, 1680 cm$^{-1}$ (5) 7-[2-Cyclopentyloxyimino-2-(2-aminothiazol-4-yl)-acetamido]-3-[1-(2-propynyl)-1H-tetrazol-5-yl]-thiomethyl-3-cephem-4-carboxylic acid (syn isomer).
I.R. (Nujol): 3260, 2110, 1780, 1665 cm$^{-1}$ (6) 7-[2-Methoxyimino-2-(5-amino-1,2,4-thiadiazol-3-yl)acetamido]-3-[1-(2-propynyl)-1H-tetrazol-5-yl]-thiomethyl-3-cephem-4-carboxylic acid (syn isomer).
I.R. (Nujol): 3300, 1770, 1670, 1620 cm$^{-1}$
N.M.R. (DMSO-d$_6$, δ): 3.63 (3H, m), 3.91 (3H, s), 4.37 (2H, q, J=12.0 Hz), 5.11 (1H, d, J=5.0 Hz), 5.32 (2H, d, J=2.0 Hz), 5.62 (1H, dd, J=5.0 and 8.0 Hz), 9.57 (1H, d, J=8.0 Hz)

(7) 7-[2-Methoxyimino-2-(thiazol-4-yl)acetamido]-3-[1-(2-propynyl)-1H-tetrazol-5-yl]thiomethyl-3-cephem-4-carboxylic acid (syn isomer).
I.R. (Nujol): 3310, 2150, 1785, 1725, 1680 cm$^{-1}$ (8) 7-[2-(1H-Tetrazol-1-yl)acetamido]-3-[1-(2-propynyl)-1H-tetrazol-5-yl]thiomethyl-3-cephem-4-carboxylic acid.
I.R. (Nujol): 3260, 2110, 1770, 1695 cm$^{-1}$ (9) 7-[2-Allyloxyimino-2-(2-formamidothiazol-4-yl)-acetamido]-3-[1-(2-propynyl)-1H-tetrazol-5-yl]-thiomethyl-3-cephem-4-carboxylic acid (syn isomer).
I.R. (Nujol): 3250, 2140, 1770, 1670 cm$^{-1}$
N.M.R. (DMSO-d$_6$, δ): 3.52–3.92 (3H, m), 4.43 (2H, q, J=14.0 Hz), 4.69 (2H, m), 5.08–5.60 (3H, m), 5.37 (2H, d, J=2.0 Hz), 5.68–6.46 (2H, m), 7.47 (1H, s), 8.60 (1H, s), 12.75 (1H, broad s)

(10) 7-[2-Allyloxyimino-2-(2-aminothiazol-4-yl)-acetamido]-3-[1-(2-propynyl)-1H-tetrazol-5-yl]-thiomethyl-3-cephem-4-carboxylic acid (syn isomer).
I.R. (Nujol): 3260, 2110, 1750, 1670, 1630 cm$^{-1}$

(11) 7-[2-(2-Cyclopenten-1-yl)oxyimino-2-(2-formamidothiazol-4-yl)acetamido]-3-[1-(2-propynyl)-1H-tetrazol-5-yl]thiomethyl-3-cephem-4-carboxylic acid (syn isomer).
I.R. (Nujol): 3240, 2125, 1775, 1680 cm$^{-1}$

(12) 7-[2-(2-Cyclopenten-1-yl)oxyimino-2-(2-aminothiazol-4-yl)acetamido]-3-[1-(2-propynyl)-1H-tetrazol-5-yl]-thiomethyl-3-cephem-4-carboxylic acid (syn isomer).
I.R. (Nujol): 3270, 2120, 1775, 1670 cm$^{-1}$

(13) 7-[2-Isopropoxyimino-2-(2-formamidothiazol-4-yl)-acetamido]-3-[1-(2-propynyl)-1H-tetrazol-5-yl]thiomethyl-3-cephem-4-carboxylic acid (syn isomer).
N.M.R. (DMSO-d$_6$, δ): 1.20 (6H, d, J=6 Hz), 3.53–3.75 (3H, m), 4.35 (2H, m), 5.13 (1H, d, J=5 Hz), 5.90 (2H, d, J=2 Hz), 5.78 (1H, dd, J=5 and 8 Hz), 7.34 (1H, s), 8.48 (1H, s), 9.57 (1H, d, J=8 Hz)

(14) 7-[2-Isopropoxyimino-2-(2-aminothiazol-4-yl)-acetamido]-3-[1-(2-propynyl)-1H-tetrazol-5-yl]-thiomethyl-3-cephem-4-carboxylic acid (syn isomer).
I.R. (Nujol): 3320, 2150, 1775, 1670 cm$^{-1}$

(15) 7-[2-(2-Propynyl)oxyimino-2-(2-formamidothiazol-4-yl)acetamido]-3-[1-(2-propynyl)-1H-tetrazol-5-yl]-thiomethyl-3-cephem-4-carboxylic acid (syn isomer).
I.R. (Nujol): 3240, 2120, 1770, 1665 cm$^{-1}$

(16) 7-[2-(2-Propynyl)oxyimino-2-(2-aminothiazol-4-yl)-acetamido]-3-[1-(2-propynyl)-1H-tetrazol-5-yl]-thiomethyl-3-cephem-4-carboxylic acid (syn isomer).
I.R. (Nujol): 3280, 2110, 1770, 1670 cm$^{-1}$

(17) 7-[2-(2-Formamidothiazol-4-yl)glyoxylamido]-3-[1-(2-propynyl)-1H-tetrazol-5-yl]thiomethyl-3-cephem-4-carboxylic acid.
I.R. (Nujol): 3260, 3120, 2130, 1765, 1715, 1670 cm$^{-1}$

(18) 7-[2-(2-Aminothiazol-4-yl)glyoxylamido]-3-]1-(2-propynyl)-1H-tetrazol-5-yl]thiomethyl-3-cephem-4-carboxylic acid.
I.R. (Nujol): 3250, 2125, 1765, 1665, 1630 cm$^{-1}$

(19) 7-[2-(2-Aminothiazol-4-yl)-D,L-glycolamido]-3-[1-(2-propynyl)-1H-tetrazol-5-yl]thiomethyl-3-cephem-4-carboxylic acid.
I.R. (Nujol): 3260, 2140, 1770, 1680, 1630 cm$^{-1}$

(20) 7-[2-Benzyloxyimino-2-[2-(2,2,2-trifluoroacetamido)-thiazol-4-yl]acetamido]-3-[1-(2-propynyl)-1H-tetrazol-5-yl]thiomethyl-3-cephem-4-carboxylic acid (syn isomer).
I.R. (Nujol): 3280, 3230, 2140, 1785, 1725, 1655 cm$^{-1}$

(21) 7-[2-Benzyloxyimino-2-(2-aminothiazol-4-yl)-acetamido]-3-[1-(2-propynyl-1H-tetrazol-5-yl]-thiomethyl-3-cephem-4-carboxylic acid (syn isomer).
I.R. (Nujol): 3270, 2110, 1770, 1665 cm$^{-1}$

(22) 7-[D-2-Formyloxy-2-phenylacetamido]-3-[1-(2-propynyl)-1H-tetrazol-5-yl]thiomethyl-3-cephem-4-carboxylic acid.
I.R. (Nujol): 3260, 2130, 1775, 1715 cm$^{-1}$

(23) 7-(2-Phenyl-D-glycolamido)-3-[1-(2-propynyl)-1H-tetrazol-5-yl]thiomethyl-3-cephem-4-carboxylic acid.
I.R. (Nujol): 3300, 3260, 2130, 1775, 1680 cm$^{-1}$

(24) 7-[2-tert-Butoxycarbonylmethoxyimino-2-(2-formamidothiazol-4-yl)acetamido]-3-[1-(2-propynyl)-1H-tetrazol-5-yl]thiomethyl-3-cephem-4-carboxylic acid (syn isomer).
I.R. (Nujol): 3240, 2130, 1780, 1720, 1675 cm$^{-1}$

(25) 7-[2-tert-Butoxycarbonylmethoxyimino-2-(2-aminothiazol-3-yl)acetamido]-3-[1-(2-propynyl)-1H-tetrazol-5-yl]thiomethyl-3-cephem-4-carboxylic acid hydrochloride (syn isomer).
I.R. (Nujol): 3350, 3230, 2125, 1770, 1715, 1675, 1625 cm$^{-1}$

(26) 7-[2-Carboxymethoxyimino-2-(2-aminothiazol-4-yl)acetamido]-3-[1-(2-propynyl)-1H-tetrazol-5-yl]thiomethyl-3-cephem-4-carboxylic acid hydrochloride (syn isomer).
I.R. (Nujol): 3260, 2120, 1765, 1660, 1625 cm$^{-1}$

(27) 7-[2-Ethoxyimino-2-(2-aminothiazol-4-yl)acetamido]-3-[1-(2-propynyl)-1H-tetrazol-5-yl]thiomethyl-3-cephem-4-carboxylic acid (syn isomer).
IR (Nujol): 3250, 2100, 1770, 1670, 1625 cm$^{-1}$

(28) 7-[2-Ethoxyimino-2-(2-formamidothiazol-4-yl)acetamido]-3-[1-(2-propynyl)-1H-tetrazol-5-yl]thiomethyl-3-cephem-4-carboxylic acid (syn isomer).
IR (Nujol): 3250, 3150, 2140, 1770, 1680, 1650 cm$^{-1}$

(29) 7-[2-(Cyclopentyloxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer), mp. 145° to 150° C. (dec.).

IR (Nujol): 3300, 3200, 2120, 1775, 1680, 1620, 1520 cm$^{-1}$

(30) 7-[2-(2-Cyclopenten-1-yl)oxyimino-2-(5-amino-1,2,4-thiadiazol-3-yl)acetamido-3-[1-(2-propynyl)-1H-tetrazol-5-yl]thiomethyl-3-cephem-4-carboxylic acid (syn isomer), mp. 145° to 150° C. (dec.).

IR (Nujol): 3300, 3200, 2120, 1770, 1675, 1620, 1520 cm$^{-1}$

(31) 7-[2-tert-Butoxycarbonylmethoxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer), mp. 120° to 125° C. (dec.).

IR (Nujol): 3300, 1770, 1720, 1680, 1620, 1520 cm$^{-1}$

(32) 7-[2-Carboxymethoxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer), mp. 160° to 165° C. (dec.).

IR (Nujol): 3300, 3250, 1770, 1720, 1680, 1620, 1520 cm$^{-1}$

(33) 7-(D-2-tert-Butoxycarbonylamino-2-phenylacetamido)-3-[1-(2-propynyl)-1H-tetrazol-5-yl]thiomethyl-3-cephem-4-carboxylic acid.

IR (Nujol): 3260, 2130, 1775, 1700, 1685 1660 cm$^{-1}$

(34) 7-(D-2-Phenylglycylamino)-3-[1-(2-propynyl)-1H-tetrazol-5-yl]thiomethyl-3-cephem-4-carboxylic acid trifluoroacetate.

IR (Nujol): 3250, 2130, 1775, 1660 cm$^{-1}$

(35) 7-(2-Allylthioacetamido)-3-[1-(2-propynyl)-1H-tetrazol-5-yl]thiomethyl-3-cephem-4-carboxylic acid.

IR (KBr): 3250, 2940, 2110, 1770, 1710 cm$^{-1}$

EXAMPLE 21

To a mixture of 7-[2-methoxyimino-2-(2-formamidothiazol-4-yl)acetamido]-3-[1-(2-propynyl)-1H-tetrazol-5-yl]thiomethyl-3-cephem-4-carboxylic acid (syn isomer) (1.4 g) in methanol (10.0 ml) were added conc. hydrochloric acid (0.52 g) and tetrahydrofuran (5.0 g) and the mixture was stirred for 2 hours and 10 minutes at room temperature. After the evaporation of the reaction mixture, to the residue were added water and ethyl acetate and then the resulting mixture was adjusted to pH 7.0 with a saturated aqueous solution of sodium carbonate. The aqueous layer was separated, washed with ethyl acetate (x2) and then concentrated. The concentrate was adjusted to pH 3.0 with 10% hydrochloric acid and the precipitates were collected by filtration, washed with water and dried over phosphorus pentoxide under reduced pressure to give 7-[2-methoxyimino-2-(2-aminothiazol-4-yl)acetamido]-3-[1-(2-propynyl)-1H-tetrazol-5-yl]thiomethyl-3-cephem-4-carboxylic acid (syn isomer) (0.65 g).

I.R. (Nujol): 3280, 2100, 1770, 1660, 1630 cm$^{-1}$
N.M.R. (DMSO-d$_6$, δ): 3.53–3.83 (3H, m), 3.87 (3H, s), 4.39 (2H, q, J=14.0 Hz), 5.13 (1H, d, J=5.0 Hz), 5.32 (2H, d, J=2.0 Hz), 5.77 (1H, dd, J=5.0 and 8.0 Hz), 6.78 (1H, s), 8.59 (1H, d, J=8.0 Hz)

EXAMPLE 22

To a mixture of benzhydryl 7-[2-methoxyimino-2-(2-formamidothiazol-4-yl)acetamido]-3-[2-(2-propynyl)-2H-tetrazol-5-yl]thiomethyl-3-cephem-4-carboxylate (syn isomer)(2.7 g) in methanol (19.0 ml) were added conc. hydrochloric acid (0.75 g) and tetrahydrofuran (10 ml) and the mixture was stirred for 3 hours at room temperature. After the evaporation of the reaction mixture, to the residue were added water and ethyl acetate and then the resulting mixture was adjusted to pH 7.0 with a saturated aqueous solution of sodium carbonate. After the addition of tetrahydrofuran to the resulting mixture, the organic layer was separated, washed with a saturated aqueous solution of sodium chloride (x2), dried over magnesium sulfate and then evaporated. The residue was pulverized in isopropyl ether, collected by filtration, washed with isopropyl ether and then dried to give benzhydryl 7-[2-methoxyimino-2-(2-aminothiazol-4-yl)-acetamido]-3-[2-(2-propynyl)-2H-tetrazol-5-yl]-thiomethyl-3-cephem-4-carboxylate (syn isomer)(2.0 g).

I.R. (Nujol): 3270, 2150, 1775, 1725, 1670, 1680 cm$^{-1}$
N.M.R. (DMSO-d$_6$): 3.56–3.80 (3H, m), 3.83 (3H, s), 4.25 (2H, q, J=13.0 Hz), 5.20 (1H, d, J=4.0 Hz), 5.62 (2H, d, J=2.0 Hz), 5.90 (1H, dd, J=4.0 and 8.0 Hz), 6.76 (1H, s), 6.94 (1H, s), 7.06–7.73 (10H, m), 9.62 (1H, d, J=8.0 Hz)

EXAMPLE 23

A mixture of 2-[2-cyclopentyloxyimino-2-[2-(2,2,2-trifluoroacetamido)thiazol-4-yl]acetamido]-3-[1-(2-propynyl)-1H-tetrazol-5-yl]thiomethyl-3-cephem-4-carboxylic acid (syn isomer)(2.4 g), sodium acetate trihydrate (4.76 g) and water (50 ml) was stirred for 13 hours at room temperature and thereto was added tetrahydrofuran (15 ml). The mixture was stirred at 25° to 30° C. for 10 hours and at 15° C. overnight. The reaction mixture was adjusted to pH 7.0 with a saturated aqueous solution of sodium bicarbonate and washed with ethyl acetate (15 ml). The washed aqueous layer was adjusted to pH 2.8 with 10% hydrochloric acid at 5° to 10° C. The precipitates were collected by filtration, washed with water and then dried to give 7-[2-cyclopentyloxyimino-2-(2-aminothiazol-4-yl)acetamido]-3-[1-(2-propynyl)-1H-tetrazol-5-yl]thiomethyl-3-cephem-4-carboxylic acid (0.72 g).

I.R. (Nujol): 3260, 2110, 1780, 1665 cm$^{-1}$
N.M.R. (DMSO-d$_6$, δ): 1.30–2.07 (8H, m), 3.50–3.84 (3H, m), 4.42 (2H, ABq, J=14 Hz), 4.53–4.82 (1H, m), 5.15 (1H, d, J=5 Hz), 5.32 (2H, d, J=2.5 Hz), 5.79 (1H, dd, J=5 and 8 Hz), 6.68 (1H, s), 9.48 (1H, d, J=8 Hz).

EXAMPLE 24

A mixture of 7-[2-ethoxyimino-2-(2-formamidothiazol-4-yl)acetamido[-3-[1-(2-propynyl)-1H-tetrazol-5-yl]thiomethyl-3-cephem-4-carboxylic acid (syn isomer) (1.6 g) and conc. hydrochloric acid (0.6 g) in methanol (16 ml) was stirred for 3 hours at room temperature. The reaction mixture was evaporated. The residue was added to mixture of water and ethyl acetate and adjusted to pH 7.5 with a saturated aqueous solution of sodium bicarbonate. The separated aqueous layer was adjusted to pH 3.0 with 10% hydrochloric acid. The precipitates were collected by filtration, washed with water and dried over phosphorus pentoxide in vacuo to give 7-[2-ethoxyimino-2-(2-aminothiazol-4-yl)acetamido]-3-[1-(2-propynyl)-1H-tetrazol-5-yl]thiomethyl-3-cephem-4-carboxylic acid (syn isomer)(1.24 g).

IR (Nujol): 3250, 2100, 1770, 1670, 1625 cm$^{-1}$
NMR (DMSO-d$_6$, δ): 1.23 (3H, t, J=7.0 Hz), 3.69 (3H, m), 4.14 (2H, q, J=7.0 Hz), 4.39 (2H, q, J=14.0 Hz), 5.14 (1H, d, J=5.0 Hz), 5.33 (2H, d, J=2.0 Hz), 5.80 (1H, dd, J=5.0 and 8.0 Hz), 6.75 (1H, s), 9.56 (1H, d, J=8.0 Hz).

EXAMPLE 25

The following compounds were prepared according to the similar manners to those of Examples 21 to 24.

(1) 7-[2-Methoxyimino-2-(2-aminothiazol-4-yl)acetamido]-3-[2-(2-propynyl)-2H-tetrazol-5-yl]thiomethyl-3-cephem-4-carboxylic acid (syn isomer).

I.R. (Nujol): 3300, 2100, 1770, 1660, 1630 cm$^{-1}$ (2) Benzhydryl 7-[2-methoxyimino-2-(5-amino-1,2,4-thiadiazol-3-yl)acetamido]-3-[1-(2-propynyl)-1H-tetrazol-5-yl]thiomethyl-3-cephem-4-carboxylate (syn isomer).

I.R. (Nujol): 3250, 2130, 1770, 1720, 1660, 1620 cm$^{-1}$ (3) 7-[2-Methoxyimino-2-(5-amino-1,2,4-thiadiazol-3-yl)-acetamido]-3-[1-(2-propynyl)-1H-tetrazol-5-yl]-thiomethyl-3-cephem-4-carboxylic acid (syn isomer).

I.R. (Nujol): 3300, 1770, 1670, 1620 cm$^{-1}$ (4) 7-[2-Allyloxyimino-2-(2-aminothiazol-4-yl)acetamido]-3-[1-(2-propynyl)-1H-tetrazol-5-yl]thiomethyl-3-cephem-4-carboxylic acid (syn isomer).

I.R. (Nujol): 3260, 2110, 1750, 1670, 1630 cm$^{-1}$

N.M.R. (DMSO-d$_6$, δ): 3.44–3.93 (3H, m), 4.39 (2H, q, J=14.0 Hz), 4.62 (2H, m), 5.03–5.52 (5H, m), 5.63–6.50 (2H, m), 6.73 (1H, s), 9.60 (1H, d, J=8.0 Hz)

(5) 7-[2-(2-Cyclopenten-1-yl)oxyimino-2-(2-aminothiazol-4-yl)acetamido]-3-[1-(2-propynyl)-1H-tetrazol-5-yl]-thiomethyl-3-cephem-4-carboxylic acid (syn isomer).

I.R. (Nujol): 3270, 2120, 1775, 1670 cm$^{-1}$

N.M.R. (DMSO-d$_6$, δ): 1.77–2.63 (4H, m), 3.53–3.87 (3H, m), 4.40 (2H, ABq, J=14 Hz), 5.11 (1H, d, J=5 Hz), 5.20–5.48 (3H, m), 5.67–6.28 (3H, m), 6.71 (1H, s), 6.97–7.50 (2H, broad s), 9.49 (1H, d, J=8 Hz).

(6) 7-[2-Isopropoxyimino-2-(2-aminothiazol-4-yl)-acetamido]-3-[1-(2-propynyl)-1H-tetrazol-5-yl]-thiomethyl-3-cephem-4-carboxylic acid (syn isomer).

I.R. (Nujol): 3320, 2150, 1775, 1670 cm$^{-1}$

N.M.R. (DMSO-d$_6$, δ): 1.22 (6H, d, J=7 Hz), 3.62–3.85 (3H, m), 4.03–4.67 (3H, m), 5.14 (1H, d, J=5 Hz), 5.32 (2H, d, J=2 Hz), 5.81 (1H, dd, J=5 and 8 Hz), 6.71 (1H, s), 7.00–7.50 (2H, broad s), 9.48 (1H, d, J=8 Hz).

(7) 7-[2-(2-Propynyl)oxyimino-2-(2-aminothiazol-4-yl)-acetamido]-3-[1-(2-propynyl)-1H-tetrazol-5-yl]-thiomethyl-3-cephem-4-carboxylic acid (syn isomer).

I.R. (Nujol): 3280, 2110, 1770, 1670 cm$^{-1}$

N.M.R. (DMSO-d$_6$, δ): 3.45 (1H, t, J=2 Hz), 3.60–3.87 (3H, m), 4.41 (2H, ABq, J=13 Hz), 4.70 (2H, d, J=2 Hz), 5.11 (1H, d, J=5 Hz), 5.34 (2H, d, J=2 Hz), 5.80 (1H, dd, J=5 and 8 Hz), 6.80 (1H, s), 7.03–7.30 (2H, broad s), 9.67 (1H, d, J=8 Hz).

(8) 7-[2-(2-Aminothiazol-4-yl)glyoxylamido]-3-[1-(2-propynyl)-1H-tetrazol-5-yl]thiomethyl-3-cephem-4-carboxylic acid.

I.R. (Nujol): 3250, 2125, 1765, 1665, 1630 cm$^{-1}$

N.M.R. (DMSO-d$_6$, δ): 3.60–3.92 (3H, m), 4.44 (2H, ABq, J=14 Hz), 5.18 (1H, d, J=5 Hz), 5.39 (2H, d, J=2 Hz), 5.78 (1H, dd, J=5 and 8 Hz), 8.05 (1H, s), 9.84 (1H, d, J=8 Hz).

(9) 7-[2-(2-Aminothiazol-4-yl)-D,L-glycolamido]-3-[1-(2-propynyl)-1H-tetrazol-5-yl]thiomethyl-3-cephem-4-carboxylic acid.

I.R. (Nujol): 3260, 2140, 1770, 1680, 1630 cm$^{-1}$

(10) 7-[2-Benzyloxyimino-2-(2-aminothiazol-4-yl)-acetamido]-3-[1-(2-propynyl)-1H-tetrazol-5-yl]-thiomethyl-3-cephem-4-carboxylic acid (syn isomer).

I.R. (Nujol): 3270, 2110, 1770, 1665 cm$^{-1}$

N.M.R. (DMSO-d$_6$, δ): 3.50–3.85 (3H, m), 4.57 (2H, ABq, J=14 Hz), 5.10–5.28 (3H, m), 5.36 (2H, d, J=2 Hz), 5.82 (1H, dd, J=5 and 8 Hz), 6.78 (1H, s), 7.18–7.59 (5H, m), 9.75 (1H, d, J=8 Hz).

(11) 7-[2-tert-Butoxycarbonylmethoxyimino-2-(2-aminothiazol-4-yl)acetamido]-3-[1-(2-propynyl)-1H-tetrazol-5-yl]thiomethyl-3-cephem-4-carboxylic acid hydrochloride (syn isomer).

I.R. (Nujol): 3350, 3230, 2125, 1770, 1715, 1675, 1625 cm$^{-1}$

N.M.R. (DMSO-d$_6$, δ): 1.40 (9H, s), 3.60–3.83 (3H, m), 4.39 (2H, ABq, J=14 Hz), 4.66 (2H, s), 5.17 (1H, d, J=5 Hz), 5.38 (2H, d, J=2 Hz), 5.81 (1H, dd, J=5 and 8 Hz), 7.02 (1H, s), 9.75 (1H, d, J=8 Hz).

(12) 7-[2-Carboxymethoxyimino-2-(2-aminothiazol-4-yl)acetamido]-3-[1-(2-propynyl)-1H-tetrazol-5-yl]thiomethyl-3-cephem-4-carboxylic acid hydrochloride (syn isomer).

I.R. (Nujol): 3260, 2120, 1765, 1660, 1625 cm$^{-1}$

(13) 7-[2-Cyclopentyloxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer), mp. 145° to 150° C. (dec.).

IR (Nujol): 3300, 3200, 2120, 1775, 1680, 1620, 1520 cm$^{-1}$

(14) 7-[2-(2-Cyclopenten-1-yl)oxyimino-2-(5-amino-1,2,4-thiadiazol-3-yl)acetamido-3-[1-(2-propynyl)-1H-tetrazol-5-yl]thiomethyl-3-cephem-4-carboxylic acid (syn isomer), mp. 145° to 150° C. (dec.).

IR (Nujol): 3300, 3200, 2120, 1770, 1675, 1620, 1520 cm$^{-1}$

(15) 7-[2-tert-Butoxycarbonylmethoxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer), mp. 120° to 125° C. (dec.).

IR (Nujol): 3300, 1770, 1720, 1680, 1620, 1520 cm$^{-1}$

(16) 7-[2-Carboxymethoxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer), mp. 160° to 165° C. (dec.).

IR (Nujol): 3300, 3250, 1770, 1720, 1680, 1620, 1520 cm$^{-1}$.

EXAMPLE 26

To a solution of 7-[2-(2-aminothiazol-4-yl)-glyoxylamido]-3-[1-(2-propynyl)-1H-tetrazol-5-yl]-thiomethyl-3-cephem-4-carboxylic acid (1.80 g) in tetrahydrofuran (10 ml) and methanol (30 ml) precooled to 0° to 5° C. was added sodium borohydride (0.13 g) and the resulting mixture was allowed to stand for 40 minutes at the same temperature. After the evaporation of the reaction mixture, the residue was dissolved in a saturated aqueous solution of sodium bicarbonate (25 ml), washed with ethyl acetate, adjusted to pH 2.8 with 10% hydrochloric acid. The precipitates were collected by filtration, washed with water and then dried over phosphorus pentoxide to give 7-[2-(2-aminothiazol-4-yl)-D,L-glycolamido]-3-[1-(2-propynyl)-1H-tetrazol-5-yl]thiomethyl-3-cephem-4-carboxylic acid (1.15 g).

I.R. (Nujol): 3260, 2140, 1770, 1680, 1630 cm$^{-1}$

N.M.R. (DMSO-d$_6$, δ): 3.62–3.83 (3H, m), 4.39 (2H, ABq, J=14 Hz), 4.88 (1H, s), 5.08 (1H, d, J=5 Hz), 5.32 (2H, d, J=2 Hz), 5.57–5.84 (1H, m), 6.43 (1H, s), 6.83–7.33 (2H, broad s), 8.34 (0.5H, d, J=8 Hz), 8.40 (0.5H, d, J=8 Hz).

EXAMPLE 27

The following compound was prepared according to a similar manner to that of Example 26. 7-(2-Phenyl-D-glycolamido)-3-[1-(2-propynyl)-1H-tetrazol-5-yl]thiomethyl-3-cephem-4-carboxylic acid.

I.R. (Nujol): 3300, 3260, 2130, 1775, 1680 cm$^{-1}$

EXAMPLE 28

A mixture of 7-(D-2-formyloxy-2-phenylacetamido)-3-[1-(2-propynyl)-1H-tetrazol-5-yl]thiomethyl-3-cephem-4-carboxylic acid (1.1 g), conc. hydrochloric acid (0.47 g) and methanol (11 ml) was stirred at room temperature for 3 hours. After the evaporation of the reaction mixture, the residue was dissolved in a saturated aqueous solution of sodium bicarbonate (20 ml), washed with ethyl acetate, adjusted to pH 2.7 with 10% hydrochloric acid under ice-cooling. The precipitates were collected by filtration, washed with water and then dried over phosphorus pentoxide to give 7-(2-Phenyl-D-glycolamido)-3-[1-(2-propynyl)-1H-tetrazol-5-yl]thiomethyl-3-cephem-4-carboxylic acid (0.56 g).

I.R. (Nujol): 3300, 3260, 2130, 1775, 1680 cm$^{-1}$

N.M.R. (DMSO-$d_6$, δ): 3.38–3.88 (3H, m), 4.37 (2H, ABq, J=14 Hz), 5.04 (1H, d, J=5 Hz), 5.10 (1H, s), 5.32 (2H, d, J=2 Hz), 5.70 (1H, dd, J=5 and 8 Hz), 7.17–7.67 (5H, m), 8.68 (1H, d, J=8 Hz).

EXAMPLE 29

The following compound was prepared according to a similar manner to that of Example 28.

7-[2-(2-Aminothiazol-4-yl)-D,L-glycolamido]-3-[1-(2-propynyl)-1H-tetrazol-5-yl]thiomethyl-3-cephem-4-carboxylic acid.

I.R. (Nujol): 3260, 2140, 1770, 1680, 1630 cm$^{-1}$.

EXAMPLE 30

A mixture of 7-[2-tert-butoxycarbonylmethoxyimino-2-(2-aminothiazol-4-yl)acetamido]-3-[1-(2-propynyl)-1H-tetrazol-5-yl]thiomethyl-3-cephem-4-carboxylic acid hydrochloride (syn isomer) (1.57 g.), anisole (1.57 ml.) and trifluoroacetic acid (8 ml.) was stirred for 3 hours at 10° to 15° C. After the addition of diisopropyl ether to the reaction mixture with stirring, the precipitates were collected by filtration, washed with diisopropyl ether and then dried to give 7-[2-carboxymethoxyimino-2-(2-aminothiazol-4-yl)acetamido]-3-[1-(2-propynyl)-1H-tetrazol-5-yl]thiomethyl-3-cephem-4-carboxylic acid hydrochloride (syn isomer) (1.38 g.)

I.R. (Nujol): 3260, 2120, 1765, 1660, 1625 cm$^{-1}$

N.M.R. (DMSO-$d_6$, δ): 3.60–3.88 (3H, m), 4.40 (2H, ABq, J=14 Hz), 4.68 (2H, s), 5.16 (1H, d, J=5 Hz), 5.35 (2H, d, J=2 Hz), 5.83 (1H, dd, J=5 Hz, 8 Hz), 6.97 (1H, s), 9.70 (1H, d, J=8 Hz)

EXAMPLE 31

A mixture of 7-[2-tert-butoxycarbonylmethoxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer)(3.5 g), formic acid (35 ml) and conc. hydrochloric acid (1.0 ml) was stirred for an hour at room temperature. The reaction mixture was evaporated and the residue was pulverized with diethyl ether and dried. Thus obtained product (3.2 g) was dissolved in an aqueous solution of sodium bicarbonate and ethyl acetate was added thereto. The mixture was adjusted to pH 1 with 6 N hydrochloric acid and then filtered. The ethyl acetate layer was separated from the filtrate, washed with a saturated aqueous solution of sodium chloride, treated with activated charcoal, dried over magnesium sulfate and then evaporated. The residue was pulverized with diethyl ether and dried to give a crude product (2.0 g). The product was dissolved in an aqueous solution of sodium bicarbonate and the solution was acidified with 6 N hydrochloric acid. The precipitates were collected by filtration, washed with water and then dried to give 7-[2-carboxymethoxyimino-2-(5-amino-1,2,4-thiadiazol-3-yl)acetamido]-3-[1-(2-propynyl)-1H-tetrazol-5-yl]thiomethyl-3-cephem-4-carboxylic acid (syn isomer) (1.0 g), mp. 160° to 165° C. (dec.).

IR (Nujol): 3300, 3250, 1770, 1720, 1680, 1620, 1520 cm$^{-1}$

NMR (DMSO-$d_6$, δ): 3.58 (1H, t, J=3 Hz), 3.63 (2H, broad s), 4.25,4.43 (2H, ABq, J=14 Hz), 4.63 (2H, s), 5.07 (1H, d, J=4 Hz), 5.27 (2H, d, J=3 Hz), 5.80 (1H, 2d, J=4 and 8 Hz), 8.10 (2H, s), 9.50 (1H, d, J=8 Hz).

EXAMPLE 32

A mixture of 7-[D-2-tert-butoxycarbonylamino-2-phenylacetamido)-3-[1-(2-propynyl)-1H-tetrazol-5-yl]-thiomethyl-3-cephem-4-carboxylic acid (0.33 g), trifluoroacetic acid (1 ml) and anisole (0.5 ml) was stirred at room temperature for 30 minutes and isopropyl ether was added. The resulting precipitates were collected by filtration and washed with isopropyl ether to give 7-(D-2-phenylglycylamino)-3-[1-(2-propynyl)-1H-tetrazol-5-yl]thiomethyl-3-cephem-4-carboxylic acid trifluoroacetate (0.33 g).

IR (Nujol): 3250, 2130, 1775, 1660 cm$^{-1}$

NMR (DMSO-$d_6$, δ): 3.50–3.73 (3H, m), 4.37 (2H, ABq, J=14 Hz), 5.05 (1H, d, J=5 Hz), 5.33 (2H, d, J=2 Hz), 5.80 (1H, dd, J=5 and 8 Hz), 6.83–7.00 (1H, m), 7.50 (5H, m), 8.85 (2H, broad s), 9.57 (1H, d, J=8 Hz).

What we claim is:

1. A new cephem compound of the formula:

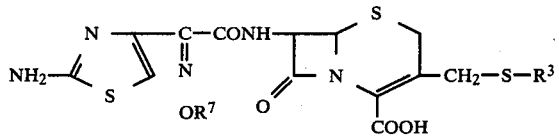

wherein $R^7$ is lower alkyl, lower alkenyl, lower alkynyl, cycloalkyl, cyclo(lower)alkenyl, phenyl(lower)alkyl, or carboxy(lower)alkyl; and $R^3$ is 1-(2-propynyl)-1H-tetrazol-5-yl or 2-(2-propynyl)-2H tetrazol-5-yl.

2. The compound of claim 1, which is 7-[2-methoxyimino-2-(2-aminothiazol-4-yl)acetamido]-3-[1-(2-propynyl)-1H-tetrazol-5-yl]thiomethyl-3-cephem-4-carboxylic acid (syn isomer).

3. The compound of claim 1, which is 7-[2-ethoxyimino-2-(2-aminothiazol-4-yl)acetamido]-3-[1-(2-propynyl)-1H-tetrazol-5-yl]thiomethyl-3-cephem-4-carboxylic acid (syn isomer).

4. The compound of claim 1, which is 7-[2-isopropoxyimino-2-(2-aminothiazol-4-yl)-acetamido]-3-[1-(2-propynyl)-1H-tetrazol-5-yl]-thiomethyl-3-cephem-4-carboxylic acid (syn isomer).

5. The compound of claim 1, which is 7-[2-allyloxyimino-2-(2-aminothiazol-4-yl)-acetamido]-3-[1-(2-propynyl)-1H-tetrazol-5-yl]-thiomethyl-3-cephem-4-carboxylic acid (syn isomer).

6. The compound of claim 1, which is 7-[2-(2-propynyloxyimino)-2-(2-aminothiazol-4-yl)-acetamido]-3-[1-(2-propynyl)-1H-tetrazol-5-yl]-thiomethyl-3-cephem-4-carboxylic acid (syn isomer).

7. The compound of claim 1, which is 7-[2-cyclopenthyloxyimino-2-(2-aminothiazol-4-yl)-acetamido]-3-[1-

(2-propynyl)-1H-tetrazol-5-yl]-thiomethyl-3-cephem-4-carboxylic acid (syn isomer).

8. The compound of claim 1, which is 7-[2-(2-cyclopenten-1-yl)oxyimino-2-(2-aminothiazol-4-yl)acetamido]-3-[1-(2-propynyl)-1H-tetrazol-5-yl]thiomethyl-3-cephem-4-carboxylic acid (syn isomer).

9. The compound of claim 1, which is 7-[2-benzyloxyimino-2-(2-aminothiazol-4-yl)acetamido]-3-[1-(2-propynyl)-1H-tetrazol-5-yl]thiomethyl-3-cephem-4-carboxylic acid (syn isomer).

10. The compound of claim 1, which is 7-[2-carboxymethoxyimino-2-(2-aminothiazol-4-yl)-acetamido]-3-[1-(2-propynyl)-1H-tetrazol-5-yl]-thiomethyl-3-cephem-4-carboxylic acid hydrochloride (syn isomer).

11. The compound of claim 1, which is 7-[2-methoxyimino-2-(2-aminothiazol-4-yl)acetamido]-3-[2-(2-propynyl)-2H-tetrazol-5-yl]thiomethyl-3-cephem-4-carboxylic acid (syn isomer).

12. An antimicrobial pharmaceutical composition comprising an effective amount of a compound of claim 1 or pharmaceutically acceptable salt thereof in association with a pharmaceutically acceptable, substantially non-toxic carrier or excipient.

* * * * *